United States Patent
Bergauer et al.

(10) Patent No.: US 7,732,600 B2
(45) Date of Patent: Jun. 8, 2010

(54) QUINOLINE AND QUINAZOLINE DERIVATIVES HAVING AFFINITY FOR 5HT1-TYPE RECEPTORS

(75) Inventors: Markus Bergauer, Verona (IT); Barbara Bertani, Verona (IT); Matteo Biagetti, Verona (IT); Steven Mark Bromidge, Verona (IT); Alessandro Falchi, Verona (IT); Colin Philip Leslie, Verona (IT); Giancarlo Merlo, Verona (IT); Domenica Antonia Pizzi, Verona (IT); Marilisa Rinaldi, Verona (IT); Luigi Piero Stasi, Verona (IT); Jessica Tibasco, Veroa (IT); Antonio Kuok Keong Vong, Harlow (GB); Simon Edward Ward, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/540,452

(22) Filed: Aug. 13, 2009

(65) Prior Publication Data

US 2009/0312546 A1 Dec. 17, 2009

Related U.S. Application Data

(63) Continuation of application No. 12/166,547, filed on Jul. 2, 2008, now Pat. No. 7,592,346, which is a continuation of application No. 11/687,098, filed on Mar. 16, 2007, now Pat. No. 7,459,456, which is a continuation of application No. 10/565,066, filed as application No. PCT/EP2004/008000 on Jul. 15, 2004, now Pat. No. 7,279,481.

(30) Foreign Application Priority Data

Jul. 18, 2003  (GB) .................................. 0316915.8

(51) Int. Cl.
| C07D 213/38 | (2006.01) |
| C07D 401/12 | (2006.01) |
| C07D 403/12 | (2006.01) |
| C07D 405/12 | (2006.01) |
| C07D 409/12 | (2006.01) |
| C07D 413/12 | (2006.01) |
| C07D 417/12 | (2006.01) |

(52) U.S. Cl. ....................................... 544/283; 544/363
(58) Field of Classification Search ........................ None
See application file for complete search history.

(56) References Cited

U.S. PATENT DOCUMENTS

| 3,937,708 A | 2/1976 | Mentrup et al. ............. 260/268 |
| 3,975,525 A | 8/1976 | Mentrup et al. ............. 424/250 |
| 3,992,537 A | 11/1976 | Mentrup et al. ............. 424/250 |
| 4,891,375 A | 1/1990 | Lowe, III ................... 514/252 |
| 4,933,447 A | 6/1990 | Koono et al. ................ 544/128 |
| 5,430,033 A | 7/1995 | Cliffe et al. ................... 514/254 |
| 5,627,177 A | 5/1997 | Cliffe et al. ................... 514/212 |
| 5,965,560 A | 10/1999 | Glase et al. .................. 514/252 |
| 6,121,267 A | 9/2000 | Glase et al. ............. 514/255.03 |
| 6,214,829 B1 | 4/2001 | Feenstra et al. ......... 514/253.06 |
| 6,759,435 B1 | 7/2004 | Chen .......................... 514/648 |
| 6,825,189 B1 | 11/2004 | Peters et al. ................ 514/218 |
| 6,897,219 B2 | 5/2005 | Peters et al. ........... 514/253.01 |
| 7,279,481 B2 | 10/2007 | Falchi et al. ........... 514/253.06 |
| 7,459,456 B2 | 12/2008 | Biagetti, et al. ........ 514/253.06 |
| 2002/0094986 A1 | 7/2002 | Chappell et al. ............. 514/249 |
| 2004/0048869 A1 | 3/2004 | Chappell et al. ............. 514/249 |
| 2004/0072823 A1 | 4/2004 | Peters et al. ................ 514/218 |
| 2005/0124625 A1 | 6/2005 | Salvati et al. ........... 514/253.01 |
| 2005/0282236 A1 | 12/2005 | Gaeta et al. .................. 435/7.9 |
| 2005/0287617 A1 | 12/2005 | Gaeta et al. ................ 435/7.92 |
| 2006/0264429 A1 | 11/2006 | Bertani et al. ............. 514/230.5 |

FOREIGN PATENT DOCUMENTS

| EP | 308897 A | 3/1989 |
| EP | 673927 A1 | 9/1995 |
| EP | 742207 A1 | 11/1996 |
| EP | 0900792 | 3/1999 |
| EP | 1213031 A2 | 6/2002 |
| GB | 2277517 A | 11/1994 |
| GB | 2312843 A | 11/1997 |
| JP | 58083677 A | 5/1983 |
| JP | 63054363 A | 10/1988 |
| JP | 02169569 A | 6/1990 |

(Continued)

OTHER PUBLICATIONS

Robichaud et al. *Annual Reports in Medicinal Chemistry*, 35: 11-20 (2000).

(Continued)

*Primary Examiner*—Emily Bernhardt
(74) *Attorney, Agent, or Firm*—Duke M. Fitch; Kathryn L. Sieburth; Lorraine B. Ling

(57) ABSTRACT

Disclosed are methods for the preparation of compounds of formula (I):

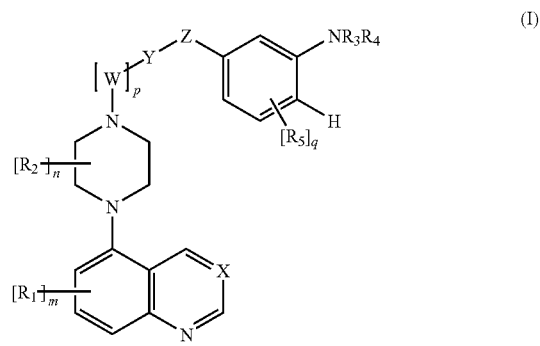

wherein $R_1$, m, X, $R_2$, n, W, p, Y, Z, $R_3$, $R_4$, $R_5$ and q have the meanings as defined in the description.

4 Claims, No Drawings

FOREIGN PATENT DOCUMENTS

| | | |
|---|---|---|
| JP | 2777159 B2 | 7/1998 |
| WO | WO9415919 A1 | 7/1994 |
| WO | WO9415928 A1 | 7/1994 |
| WO | WO 97/36893 | 10/1997 |
| WO | WO9741108 A1 | 11/1997 |
| WO | WO9825617 A1 | 6/1998 |
| WO | WO9921834 A1 | 5/1999 |
| WO | WO 99/31086 | 6/1999 |
| WO | WO0078716 A1 | 12/2000 |
| WO | WO 01/32626 | 5/2001 |
| WO | 02/074764 | 9/2002 |
| WO | WO200294203 A2 | 11/2002 |
| WO | WO2004035556 A1 | 4/2004 |
| WO | WO2004041793 A1 | 5/2004 |
| WO | WO2004046124 A1 | 6/2004 |
| WO | WO2004074218 A2 | 9/2004 |
| WO | WO2005014552 A1 | 2/2005 |
| WO | WO2005 040136 A1 | 5/2005 |
| WO | WO2005087742 A1 | 9/2005 |
| WO | WO2006024517 A1 | 3/2006 |

OTHER PUBLICATIONS

Jones et al. *Pharmacology, Biochemistry, and Behavior*, 71: 555-568 (2002).

QUINOLINE AND QUINAZOLINE DERIVATIVES HAVING AFFINITY FOR 5HT1-TYPE RECEPTORS

This application is a continuation of application Ser. No. 12/166,547, filed Jul. 2, 2008, now U.S. Pat. No. 7,592,346 which is a continuation of application Ser. No. 11/687,098, filed Mar. 16, 2007 now U.S. Pat. No. 7,459,456 which is a continuation of application Ser. No. 10/565,066, filed Jan. 17, 2006, now U.S. Pat. No. 7,279,481, which is a 371 of International Application No. PCT/EP2004/008000, filed 15 Jul. 2004, which claims benefit of Great Britain Application No. GB 0316915.8, filed 18 Jul. 2003.

BACKGROUND OF THE INVENTION

The present invention relates to novel compounds, processes for their preparation, pharmaceutical compositions containing the same and their use as medicaments in the treatment of CNS and other disorders.

SUMMARY OF THE INVENTION

A novel series of compounds has now been found that possess high affinity for 5-$HT_1$ type receptors and/or are 5-HT reuptake inhibitors. The present invention therefore provides, in a first aspect, a compound of formula (I) or a pharmaceutically acceptable salt thereof:

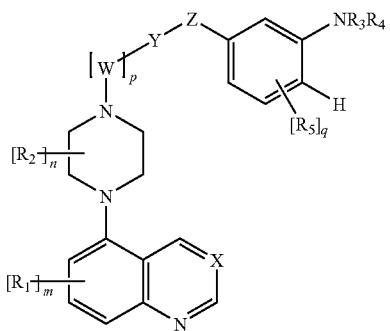

(I)

wherein:
$R_1$ is halogen, cyano, $C_{1-6}$alkyl, $C_{1-6}$alkoxy, halo$C_{1-6}$alkoxy or halo$C_{1-6}$alkyl;
m is 0, 1, 2, 3 or 4;
X is N or CH;
$R_2$ is halogen, cyano, $C_{1-6}$alkyl, $C_{1-6}$alkoxy, halo$C_{1-6}$alkoxy or halo$C_{1-6}$alkyl;
n is 0, 1 or 2;
W is —$CH_2$—, —CH($C_{1-6}$alkyl)- or —C($C_{1-6}$alkyl)($C_{1-6}$alkyl)-;
p is 0, 1, 2 or 3;
Y and Z together form a $C_{3-7}$cycloalkylene group, or Y is —$CH_2$—, —CH($C_{1-6}$alkyl)- or —C($C_{1-6}$alkyl)($C_{1-6}$alkyl) and Z is —$CH_2$—, —CHOH—, —$CHR_6$— or —$CR_6R_7$— (wherein $R_6$ and $R_7$ are independently halogen, cyano, $C_{1-6}$alkyl or $C_{1-6}$alkoxy);
$R_3$ and $R_4$ are independently hydrogen, $C_{1-6}$alkyl, $C_{1-6}$alkylsulfonyl or a group having the formula (II):

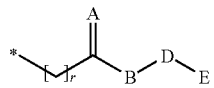

(II)

wherein
r is 0, 1, 2, 3 or 4;
A is oxygen or sulfur;
B is a single bond or —$NR_8$— (wherein $R_8$ is hydrogen, $C_{1-6}$alkyl or aryl, wherein the aryl is optionally substituted by one or more substituents independently selected from halogen, oxo, $C_{1-6}$alkyl, $CF_3$, cyano, hydroxy, $C_{1-6}$alkanoyl, and $C_{1-6}$alkoxy);
D is —$(CH_2)_t$—, —$(CH_2)_tO$— or —$O(CH_2)_t$—, wherein t is 0, 1, 2, 3 or 4; and
E is $C_{1-6}$alkyl, halo$C_{1-6}$alkyl, $C_{3-7}$cycloalkyl (optionally substituted by one or more substituents independently selected from halogen, hydroxy, oxo, $C_{1-6}$alkyl, cyano, $CF_3$, $OCF_3$, $C_{1-6}$alkoxy and $C_{1-6}$alkanoyl), aryl (optionally substituted by one or more substituents independently selected from halogen, oxo, $C_{1-6}$alkyl, $CF_3$, cyano, hydroxy, $C_{1-6}$alkanoyl and $C_{1-6}$alkoxy), or E is —$NR_9R_{10}$, wherein $R_9$ and $R_{10}$ are independently selected from hydrogen, $C_{1-6}$alkyl and aryl (optionally substituted by one or more substituents independently selected from halogen, oxo, $C_{1-6}$alkyl, $CF_3$, cyano, hydroxy, $C_{1-6}$alkanoyl and $C_{1-6}$alkoxy);
or $R_3$ and $R_4$, together with the nitrogen atom to which $R_3$ and $R_4$ are attached, form a 3-7 membered monocyclic heterocyclic group or a 8-11 membered bicyclic heterocyclic group, wherein each group is optionally substituted by one or more substituents selected from halogen, oxo, $C_{1-6}$alkyl, cyano, $CF_3$, $C_{1-6}$alkoxy, $C_{1-6}$alkanoyl, aryl and aryl$C_{1-6}$alkyl (wherein the aryl and the aryl$C_{1-6}$ alkyl are further optionally substituted by one or more halogen, oxo, $C_{1-6}$alkyl, cyano, $CF_3$, $C_{1-6}$alkoxy or $C_{1-6}$alkanoyl); and
$R_5$ is independently halogen, cyano, $C_{1-6}$alkyl or $C_{1-6}$alkoxy; and
q is 0, 1, 2, 3 or 4.

DETAILED DESCRIPTION OF THE INVENTION

The term "halogen" and its abbreviation "halo" refer to fluorine, chlorine, bromine or iodine.

The term "$C_{1-6}$alkyl" refers to an alkyl group having from one to four carbon atoms, in any isomeric form, such as methyl, ethyl, propyl, isopropyl, butyl, isobutyl, sec-butyl and tert-butyl, pentyl, neopentyl, sec-pentyl, n-pentyl, isopentyl, tert-pentyl and hexyl.

The terms "halo$C_{1-6}$alkoxy" or "halo$C_{1-6}$alkyl" are used to describe a $C_{1-6}$alkoxy or a $C_{1-6}$alkyl group, respectively, substituted with one or more halogens. Examples include —$CHCl_2$, —$CF_3$, —$OCF_3$, etc.

The term "$C_{1-6}$alkylsulfonyl" refers to a group ($C_{1-6}$alkyl)-$SO_2$—. Examples include methylsulfonyl, ethylsulfonyl and propylsulfonyl.

The term "$C_{3-7}$cycloalkyl" refers to a cycloalkyl group consisting of from 3 to 7 carbon atoms, such as cyclopropyl, cyclobutyl, cyclopentyl, cyclohexyl and cycloheptyl.

The term "$C_{1-6}$alkoxy" refers to a straight chain or branched chain alkoxy (or "alkyloxy") group having from one to six carbon atoms, such as methoxy, ethoxy, propoxy, isopropoxy, butoxy, isobutoxy, sec-butoxy, tert-butoxy, pentoxy, neopentoxy, sec-pentoxy, n-pentoxy, isopentoxy, tert-pentoxy and hexoxy.

The term "$C_{1-6}$alkanoyl" refers to an alkanoyl group having from 1 to 6 carbon atoms, such as methanoyl (or "formyl"), ethanoyl (or "acetyl"), propanoyl, isopropanoyl, butanoyl, isobutanoyl, sec-butanoyl, pentanoyl, neopentanoyl, sec-pentanoyl, isopentanoyl, tertpentanoyl and hexanoyl.

The term "aryl", whether alone or as part of another group, is intended, unless otherwise stated, to denote, a 3- to 7-membered monocyclic aromatic ring or a 6- to 10-membered bicyclic aromatic ring, wherein one or more of the carbon atoms in the ring(s) is optionally replaced by a heteroatom independently selected from nitrogen, oxygen and sulfur. Examples of monocyclic aryl groups include: phenyl, pyrrolyl, pyrrolinyl, imidazolyl, pyrazolyl, pyrazolinyl, isothiazolyl, thiazolyl, isoxazolyl, furazanyl, furyl, thienyl, pyridyl, pyridazinyl, pyrimidinyl, pyrazinyl, azepinyl and pyranyl. As used herein, the term "bicyclic aromatic ring" includes bicyclic ring systems in which both rings are aromatic, as well as bicyclic ring systems in which one of the rings is partially or fully saturated. Examples of bicyclic aryl groups include: naphthyl, indenyl, indolyl, isoindolyl, indazolyl, benzimidazolyl, benzoxazolyl, benzothienyl, benzuforanyl, dihydrobenzofuranyl, tetrahydrobenzofuranyl, quinolyl, quinoxalinyl, quinazolinyl, isoquinolyl, indazylyl, indanyl, tetrahydronaphthyl, indolinyl, isoindolinyl, tetrahydroisoquinolinyl, tetrahydroquinolyl, benzosazinyl, benzoxazinyl and benzoazepinyl. The term "aryl" as used herein covers all these groups. These groups may be attached to the rest of the molecule at any suitable position. For example, where used herein the term naphthyl, whether alone or as part of another group, is intended, unless otherwise stated, to denote both 1-naphthyl and 2-naphthyl groups.

The term "oxo" refers to the group "=O".

The term "3-7 membered monocyclic heterocyclic group" refers to a 3-7 membered, saturated, partially saturated or non-saturated ring containing 1, 2 or 3 heteroatoms selected from nitrogen, sulfur and oxygen. The term "8-11 membered bicyclic heterocyclic group" refers to an optionally substituted 8-11 membered bicyclic ring containing a total of 1, 2, 3, 4 or 5 heteroatoms selected from nitrogen, sulfur and oxygen, wherein each ring may be saturated, partially saturated or non-saturated. These groups may be attached to the rest of the molecule at any suitable position.

It is understood that, when $R_3$ and $R_4$, together with the nitrogen atom to which $R_3$ and $R_4$ are attached, form an optionally substituted 3-7 membered monocyclic heterocyclic group or an optionally substituted 8-11 membered bicyclic heterocyclic group, the heterocyclic groups are N-linked heterocyclic groups. Examples of N-linked 3-7 membered heterocyclic group include aziridinyl, azetidinyl, pyrrolidinyl, imidazolidinyl, pyrazolidinyl, isothiazolidinyl, thiazolidinyl, pyrrolyl, pyrrolinyl, pyrazolinyl, imidazolyl, pyrazolyl, triazolyl, tetrazolyl, piperidyl, piperazinyl, morpholinyl, thiazinanyl, azepinyl and azepanyl. Examples of N-linked 8-11 membered heterocyclic group include 6H-thieno[2,3-b]pyrrolyl, imidazo[2,1-b][1,3]thiazolyl, imidazo[5,1-b][1,3]thiazolyl, indolyl, isoindolyl, indazolyl, benzimidazolyl, decahydroquinolinyl, octahydro-2H-1,4-benzoxazinyl, octahydro-1H-cyclopenta[b]pyridinyl, indolinyl, isoindolinyl, tetrahydroisoquinolinyl, tetrahydroquinolinyl, benzoxazinyl, 2,3-dihydro-1,4-benzoxazinyl and benzoazepinyl.

All of these heterocyclic groups formed by $R_3$ and $R_4$ may be substituted by one or more, for example 1 to 4, substituents, which may be the same or different, and which are selected from halogen, oxo, $C_{1-6}$alkyl, cyano, $CF_3$, $C_{1-6}$alkoxy, $C_{1-6}$alkanoyl, aryl and aryl$C_{1-6}$alkyl (wherein the aryl and the aryl$C_{1-6}$alkyl are further optionally substituted by halogen, oxo, $C_{1-6}$alkyl, cyano, $CF_3$, $C_{1-6}$alkoxy or $C_{1-6}$alkanoyl). The optional substituent(s) may be attached at any suitable position, including, where available, nitrogen atom(s).

It should be understood that $R_1$ may be attached to any available position in the quinoline or quinazoline group in formula (I). For example, it may be attached to the X if X is CH.

In one embodiment, m is 1 and $R_1$ is attached at the following position:

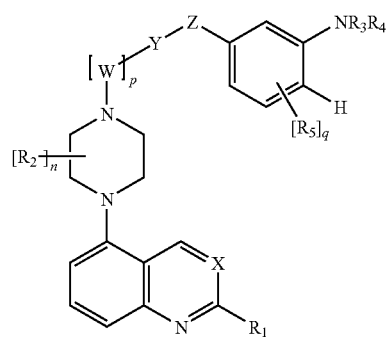

In one embodiment, n is 0. In another embodiment, n is 1 and $R_2$ is $C_{1-6}$alkyl such as methyl.

In one embodiment, p is 0.

In one embodiment, Y and Z form a $C_{3-7}$cycloalkylene, to form compounds such as:

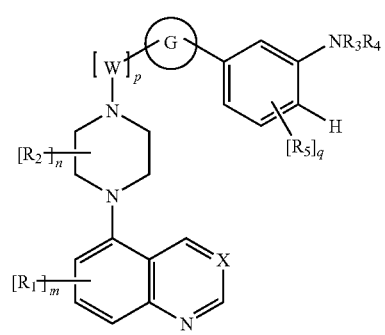

wherein G is a $C_{3-7}$cycloalkylene group, such as for example cyclopropylene.

In another embodiment, Y and Z are independently —$CH_2$—, —$CH(CH_3)$— or —$CH(OH)$—.

Each of $R_3$ and $R_4$ may independently be a group having the formula (II):

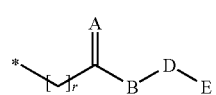

(II)

as defined above.

In one embodiment, formula (II) may be:

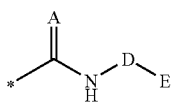
(IIa)

wherein A is oxygen or sulfur, D is —(CH$_2$)$_t$—, —(CH$_2$)$_t$O— or —O(CH$_2$)$_t$—, wherein t is 0, 1, 2, 3 or 4 and E is C$_{1-6}$alkyl, C$_{3-7}$cycloalkyl (optionally substituted by one or more substituents independently selected from halogen, hydroxy, oxo, C$_{1-6}$alkyl, cyano, CF$_3$, OCF$_3$, C$_{1-6}$alkoxy and C$_{1-6}$alkanoyl), or aryl (optionally substituted by one or more substituents independently selected from halogen, C$_{1-6}$alkyl, CF$_3$, cyano, hydroxy, C$_{1-6}$alkanoyl, and C$_{1-6}$alkoxy);

or

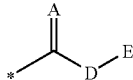
(IIb)

wherein A is oxygen or sulfur, D is —(CH$_2$)$_t$—, —(CH$_2$)$_t$O— or —O(CH$_2$)$_t$—, wherein t is 0, 1, 2, 3 or 4 and E is C$_{1-6}$alkyl, C$_{3-7}$cycloalkyl (optionally substituted by one or more substituents independently selected from halogen, hydroxy, oxo, C$_{1-6}$alkyl, cyano, CF$_3$, OCF$_3$, C$_{1-6}$alkoxy and C$_{1-6}$alkanoyl), or aryl (optionally substituted by one or more substituents independently selected from halogen, C$_{1-6}$alkyl, CF$_3$, cyano, hydroxy, C$_{1-6}$alkanoyl, and C$_{1-6}$alkoxy).

When E is an optionally substituted aryl, it may for example be a 5- to 7-membered monocyclic aromatic ring wherein one or more, for example 1 to 4, of the carbon atoms in the ring is optionally replaced by a heteroatom independently selected from nitrogen, oxygen and sulfur (such as for example phenyl or pyridyl), wherein the ring is optionally substituted by one or more substituents independently selected from oxo, halogen, C$_{1-6}$alkyl, CF$_3$, cyano, hydroxy, C$_{1-6}$alkanoyl, and C$_{1-6}$alkoxy; or E may be for example a 9- to 10-membered bicyclic aromatic ring, wherein one or more, for example 1 to 4, of the carbon atoms in the ring is optionally replaced by a heteroatom independently selected from nitrogen, oxygen and sulfur (such as for example tetrahydrobenzofuranyl, benzoxazolyl, benzisoxazolyl or indolinyl), wherein the ring is optionally substituted by one or more substituents independently selected from oxo, halogen, C$_{1-6}$alkyl, CF$_3$, cyano, hydroxy, C$_{1-6}$alkanoyl, and C$_{1-6}$alkoxy.

Examples of E include:
   C$_{1-6}$alkyl such as methyl, ethyl, propyl, isopropyl, butyl, sec-butyl or tert-butyl;
   C$_{3-7}$cycloalkyl such as cyclopropyl, cyclobutyl, cyclopentyl and cyclohexyl;
   phenyl (optionally substituted by 1, 2 or 3 substituents independently selected from CF$_3$, cyano, C$_{1-6}$alkoxy, C$_{1-6}$alkyl and halogen);

3-7 membered monocyclic aromatic rings such as:

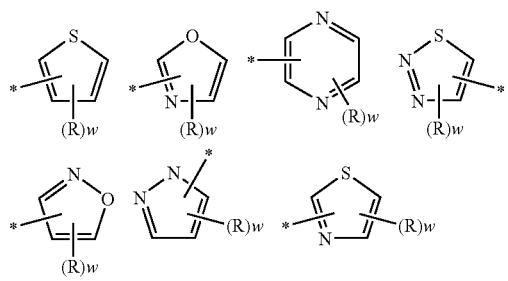

wherein w is 0, 1, 2, 3 or 4 and R is oxo, halogen, C$_{1-6}$alkyl, CF$_3$, cyano, hydroxy, C$_{1-6}$alkanoyl or C$_{1-6}$alkoxy, wherein R may be attached to any available atom, including any available nitrogen atoms; and 6-10 membered bicyclic aromatic rings such as:

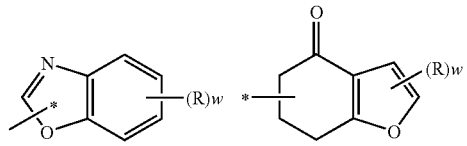

wherein w is 0, 1, 2, 3 or 4 and R is independently oxo, halogen, C$_{1-6}$alkyl, CF$_3$, cyano, hydroxy, C$_{1-6}$alkanoyl or C$_{1-6}$alkoxy, wherein R may be attached to any available atom, including any available nitrogen atoms.

When E is —NR$_9$R$_{10}$ (wherein R$_9$ and R$_{10}$ are independently selected from hydrogen, C$_{1-6}$alkyl and aryl), examples of E include methylamino, ethylamino propylamino, isopropylamino, butylamino, isobutylamino, sec-butylamino, tert-butylamino, pentylamino, neopentylamino, sec-pentylamino, n-pentylamino, isopentylamino, tert-pentylamino, hexylamino; dimethylamino, diethylamino, dipropylamino, diisopropylamino, dibutylamino, diisobutylamino, disec-butylamino, ditert-butylamino, dipentylamino, dineopentylamino, dihexylamino, butylmethylamino, isopropylmethylamino, ethylisopropylamino, ethylmethylamino; a monoarylamino such as anilino; and a monoC$_{1-6}$alkylmonoarylamino such as —N(CH$_3$)phenyl.

When R$_3$ and R$_4$, together with the nitrogen atom to which R$_3$ and R$_4$ are attached, form an optionally substituted 3-7 membered monocyclic heterocyclic group, it may be for example a 4-6 membered monocyclic heterocyclic group optionally substituted by one or more, for example 1, 2, 3 or 4, substituents selected from oxo, halogen, C$_{1-6}$alkyl, cyano, CF$_3$, C$_{1-6}$alkoxy, C$_{1-6}$alkanoyl, aryl and arylC$_{1-6}$alkyl (wherein the aryl and the arylC$_{1-6}$alkyl are further optionally substituted by one or more halogen, oxo, C$_{1-6}$alkyl, cyano, CF$_3$, C$_{1-6}$alkoxy or C$_{1-6}$alkanoyl). Examples include:

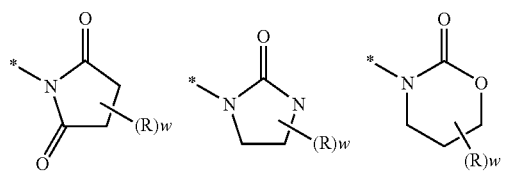

-continued

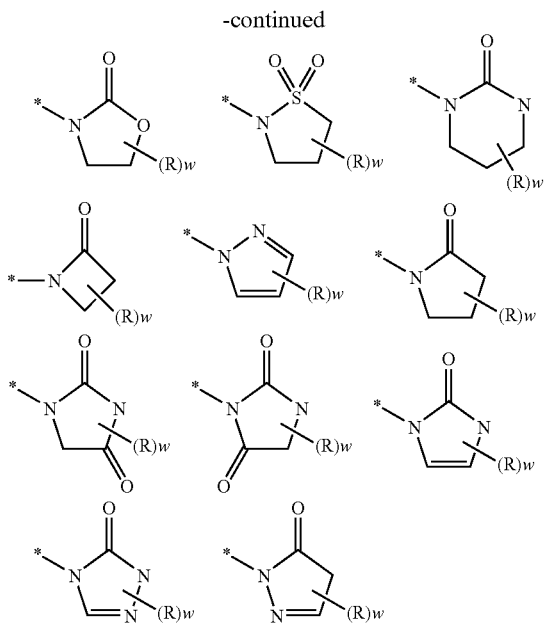

wherein w is 0, 1, 2, 3 or 4 and R is independently halogen, oxo, $C_{1-6}$alkyl, cyano, $CF_3$, $C_{1-6}$alkoxy, $C_{1-6}$alkanoyl, aryl or aryl$C_{1-6}$alkyl wherein the aryl and the aryl$C_{1-6}$alkyl are further optionally substituted by one or more, for example 1 to 3, substituents selected from halogen, oxo, $C_{1-6}$alkyl, cyano, $CF_3$, $C_{1-6}$alkoxy and $C_{1-6}$alkanoyl. Examples of R include halogen such as fluoro or chloro; $C_{1-6}$alkyl such as methyl, ethyl, propyl and/or isopropyl; $C_{1-6}$alkoxy such as methoxy or ethoxy; aryl such as phenyl or pyridyl, each of which is optionally substituted by one or two $C_{1-6}$alkyl groups such as methyl, ethyl, propyl or isopropyl; and aryl$C_{1-6}$alkyl such as pyridylmethyl, optionally substituted by one or two $C_{1-6}$alkyl groups such as methyl, ethyl, propyl or isopropyl. R may be attached to any available atom in the above groups, including any available nitrogen atoms.

When $R_3$ and $R_4$, together with the nitrogen atom to which $R_3$ and $R_4$ are attached, form an optionally substituted 8-11 membered bicyclic heterocyclic group, it may be for example a 8-10 membered bicyclic heterocyclic group optionally substituted by one or more, for example 1, 2, 3, 4 or 5, substituents selected from oxo, halogen, $C_{1-6}$alkyl, cyano, $CF_3$, $C_{1-6}$alkoxy, $C_{1-6}$alkanoyl, aryl and aryl$C_{1-6}$alkyl (wherein the aryl and the aryl$C_{1-6}$alkyl are further optionally substituted by one or more halogen, oxo, $C_{1-6}$alkyl, cyano, $CF_3$, $C_{1-6}$alkoxy or $C_{1-6}$alkanoyl). Examples include:

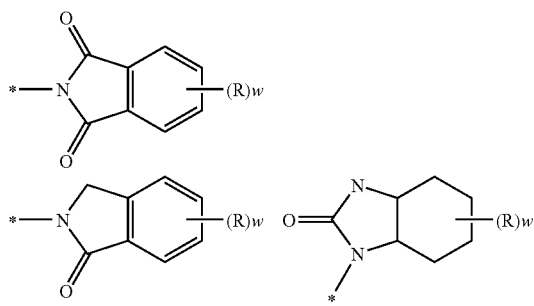

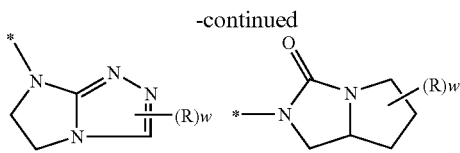

wherein w is 0, 1, 2, 3 or 4 and R is independently halogen, oxo, $C_{1-6}$alkyl, cyano, $CF_3$, $C_{1-6}$alkoxy, $C_{1-6}$alkanoyl, aryl or aryl$C_{1-6}$alkyl, wherein the aryl and the aryl$C_{1-6}$alkyl are further optionally substituted by one or more halogen, oxo, $C_{1-6}$alkyl, cyano, $CF_3$, $C_{1-6}$alkoxy or $C_{1-6}$alkanoyl. Examples of R include halogen such as fluoro or chloro, $C_{1-6}$alkyl such as methyl, ethyl, propyl and/or isopropyl; $C_{1-6}$alkoxy such as methoxy or ethoxy; aryl such as phenyl or pyridyl, each of which is optionally substituted by one or two $C_{1-6}$alkyl groups such as methyl, ethyl, propyl or isopropyl; and aryl$C_{1-6}$alkyl such as pyridylmethyl, optionally substituted by one or two $C_{1-6}$alkyl groups such as methyl, ethyl, propyl or isopropyl. It should be noted that R may be attached to any available atom in the above groups, including any available nitrogen atoms.

In one embodiment, q may be 0. In other embodiment, q is 1 and $R_5$ is halogen such as fluoro, attached to the phenyl ring in formula (I) at the position which is para to the group —$NR_3R_4$.

In one embodiment, compounds of the present invention may have a general formula (Ia):

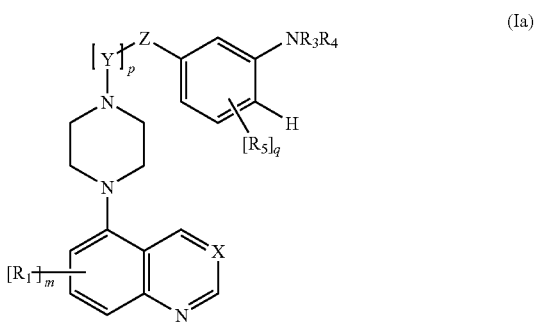

(Ia)

wherein:
$R_1$ is halogen, cyano, $C_{1-6}$alkyl, $C_{1-6}$alkoxy, halo$C_{1-6}$alkoxy or halo$C_{1-6}$alkyl;
m is 0, 1, 2, 3 or 4;
X is N or CH;
p is 1, 2, 3 or 4;
Y is —$CH_2$—, —CH($C_{1-6}$alkyl)- or —C($C_{1-6}$alkyl)($C_{1-6}$alkyl)-;
Z is —$CH_2$—, —CHOH—, —$CHR_6$— or —$CR_6R_7$—, wherein $R_6$ and $R_7$ are independently halogen, cyano, $C_{1-6}$alkyl or $C_{1-6}$alkoxy;
$R_3$ and $R_4$ are independently hydrogen, $C_{1-6}$alkyl, $C_{1-6}$alkylsulfonyl or a group having the formula (II):

(II)

wherein:
r is 0, 1, 2, 3 or 4;
A is oxygen or sulfur;
B is a single bond or —NR$_8$— wherein R$_8$ is hydrogen, C$_{1-6}$alkyl or aryl optionally substituted by one or more substituents independently selected from halogen, oxo, C$_{1-6}$alkyl, CF$_3$, cyano, hydroxy, C$_{1-6}$alkanoyl, and C$_{1-6}$alkoxy;
D is —(CH$_2$)$_t$—, —(CH$_2$)$_t$O— or —O(CH$_2$)$_t$—, wherein t is 0, 1, 2, 3 or 4; and
E is C$_{1-6}$alkyl, haloC$_{1-6}$alkyl, C$_{3-7}$cycloalkyl (optionally substituted by one or more halogen, hydroxy, oxo, C$_{1-6}$alkyl, cyano, CF$_3$, OCF$_3$, C$_{1-6}$alkoxy or C$_{1-6}$alkanoyl), or aryl (optionally substituted by one or more substituents independently selected from halogen, oxo, C$_{1-6}$alkyl, CF$_3$, cyano, hydroxy, C$_{1-6}$alkanoyl, and C$_{1-6}$alkoxy); or E is —NR$_9$R$_{10}$ (wherein R$_9$ and R$_{10}$ are independently selected from hydrogen, C$_{1-6}$alkyl and aryl optionally substituted by one or more substituents independently selected from halogen, oxo, C$_{1-6}$alkyl, CF$_3$, cyano, hydroxy, C$_{1-6}$alkanoyl, and C$_{1-6}$alkoxy);
or R$_3$ and R$_4$, together with the nitrogen atom to which R$_3$ and R$_4$ are attached, combine to form a 3-7 membered monocyclic heterocyclic group (optionally substituted by 1 to 4 substituents, which may be the same or different, and which are selected from halogen, oxo, C$_{1-6}$alkyl, cyano, CF$_3$, C$_{1-6}$alkoxy and C$_{1-6}$alkanoyl);
R$_5$ is independently halogen, cyano, C$_{1-6}$alkyl or C$_{1-6}$alkoxy; and
q is 0, 1, 2, 3 or 4.

In another embodiment, compounds of the present invention may have a general formula (Ib):

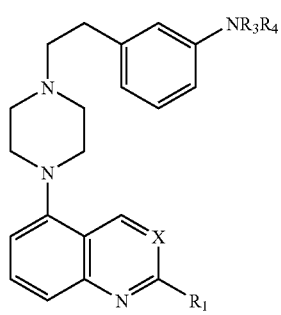

wherein X, R$_1$, R$_3$ and R$_4$ are as defined for formula (I).

All features and embodiments of formula (I) apply to formula (Ia) and (Ib), mutatis mutandis.

Specific compounds of this invention include Example numbers 1-170 (E1-E170) described below. For example, the present invention provides:

3-(3-{2-[4-(2-methyl-5-quinolinyl)-1-piperazinyl]ethyl}phenyl)-1,3-oxazolidin-2-one;

N-(3-{2-[4-(2-methyl-5-quinolinyl)-1-piperazinyl]ethyl}phenyl)-N'-phenylurea;

N-[2-(methyloxy)phenyl]-N'-(3-{2-[4-(2-methyl-5-quinolinyl)-1-piperazinyl]ethyl}phenyl)urea;

1-(3-{2-[4-(2-methyl-5-quinolinyl)-1-piperazinyl]ethyl}phenyl)-2-imidazolidinone;

2,4-dimethyl-N-(3-{2-[4-(2-methyl-5-quinolinyl)-1-piperazinyl]ethyl}phenyl)-1,3-thiazole-5-carboxamide;

N-(3-{1-hydroxy-2-[4-(2-methyl-5-quinolinyl)-1-piperazinyl]ethyl}phenyl)-2,4-dimethyl-1,3-thiazole-5-carboxamide;

2-fluoro-N-(3-{2-[4-(2-methyl-5-quinolinyl)-1-piperazinyl]ethyl}phenyl)benzamide;

3-(3-{2-[4-(2-methyl-5-quinolinyl)-1-piperazinyl]propyl}phenyl)-1,3-oxazolidin-2-one;

3-(3-{2-[(2R)-2-methyl-4-(2-methyl-5-quinolinyl)-1-piperazinyl]ethyl}phenyl)-1,3-oxazolidin-2-one;

1-methyl-3-(3-{2-[4-(2-methyl-5-quinolinyl)-1-piperazinyl]ethyl}phenyl)-2-imidazolidinone;

1-(4-fluoro-3-{2-[4-(2-methyl-5-quinolinyl)-1-piperazinyl]ethyl}phenyl)-2-imidazolidinone;

3-(4-fluoro-3-{2-[4-(2-methyl-5-quinolinyl)-1-piperazinyl]ethyl}phenyl)-1,3-oxazolidin-2-one;

1-(3-{2-[4-(2-methyl-5-quinolinyl)-1-piperazinyl]ethyl}phenyl)-2,4-imidazolidinedione;

1-(3-{2-[4-(2-methyl-5-quinolinyl)-1-piperazinyl]ethyl}phenyl)-1,3-dihydro-2H-imidazol-2-one;

1-methyl-3-(3-{2-[4-(2-methyl-5-quinolinyl)-1-piperazinyl]ethyl}phenyl)-1,3-dihydro-2H-imidazol-2-one;

4,4-dimethyl-1-(3-{2-[4-(2-methyl-5-quinolinyl)-1-piperazinyl]ethyl}phenyl)-2-imidazolidinone;

and pharmaceutically acceptable salts thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric, hydroiodic, metaphosphoric, or phosphoric acid; and organic acids e.g. succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, methanesulfonic or naphthalenesulfonic acid; base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts. Certain of the compounds of formula (I) may form acid addition salts with less than one or one or more equivalents of the acid, for example to form a dihydrochloride salt. The present invention includes within its scope all possible stoichiometric and non-stoichiometric forms. Salts having a non-physiologically acceptable anion or cation are within the scope of the invention as useful intermediates for the preparation of physiologically acceptable salts and/or for use in non-therapeutic, for example, in vitro, situations.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Certain compounds of formula (I) are capable of existing in stereoisomeric forms (e.g. geometric (or "cis-trans") isomers, diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. The present invention includes within its scope all such isomers, including mixtures.

Compounds of formula (I) may be prepared according to procedures described herein, or by analogous procedures thereto.

A reaction route for a compound of formula (I) wherein m is 1 and $R_1$ is methyl, p is 0, n is 0, and q is 0, is as follows:

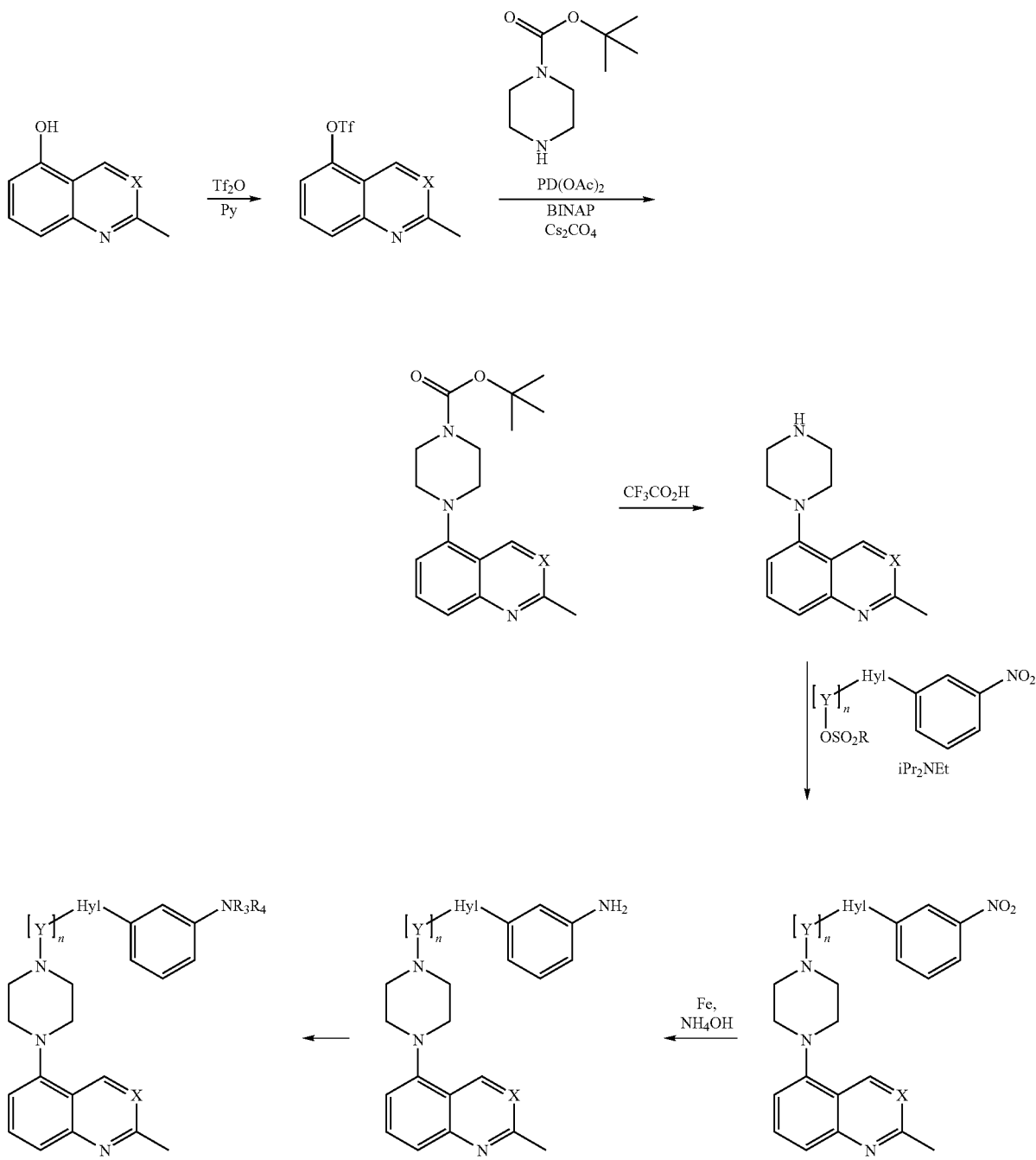

The above reaction scheme may be adapted to prepare compounds of formula (I) wherein m is other than 1, $R_1$ is other than methyl and in a position other than as illustrated above, and p, n and q are other than 0.

Compounds of formula (I) wherein Y and Z together form a $C_{3-7}$cycloalkylene group may be prepared according to procedures described herein, or by analogous procedures thereto.

A typical reaction route for a compound of formula (I) wherein Y and Z together form a cyclopropylene group, and wherein m is 1 and $R_1$ is methyl, p is 0, n is 0, and q is 0, is as follows:

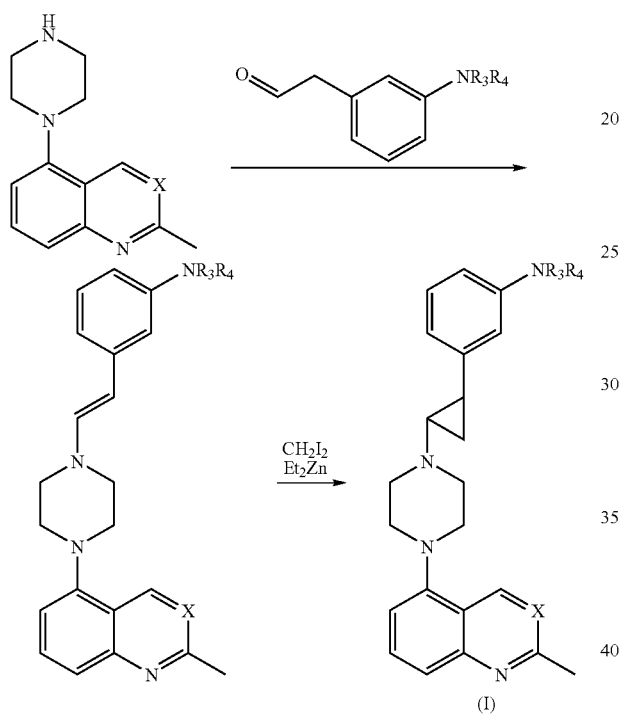

wherein X, $R_3$ and $R_4$ are as defined for formula (I). Thus, treatment of the piperazine described above with a 2-arylacetaldehyde produces an enamine, which can be treated under reaction conditions known to those skilled in the art, e.g. Simmons-Smith cyclopropanation reaction using diiodoethane and diethylzinc, to produce compounds of formula (I) wherein Y and Z together form a $C_{3-7}$cycloalkylene group. The above reaction scheme may be adapted to prepare compounds of formula (I) wherein m is other than 1, $R_1$ is other than methyl and in a position other than as illustrated above, p, n and q are other than 0, and Y and Z form a $C_{3-7}$cycloalkylene group other than cyclopropylene.

Alternatively, the reaction of an aromatic nucleophile such as a Grignard reagent (M=MgX) or aryllithium (M=Li) with a cycloalkyl epoxide (where n=0, 1, 2), optionally in the presence of a catalyst e.g. a copper(I) halide, may provide an intermediate alcohol, as illustrated in the scheme below. The alcohol may conveniently be converted into a ketone using a suitable oxidising agent, e.g. pyridinium chlorochromate. The ketone may then be transformed to a compound of formula (I) using methods described in the preceding scheme.

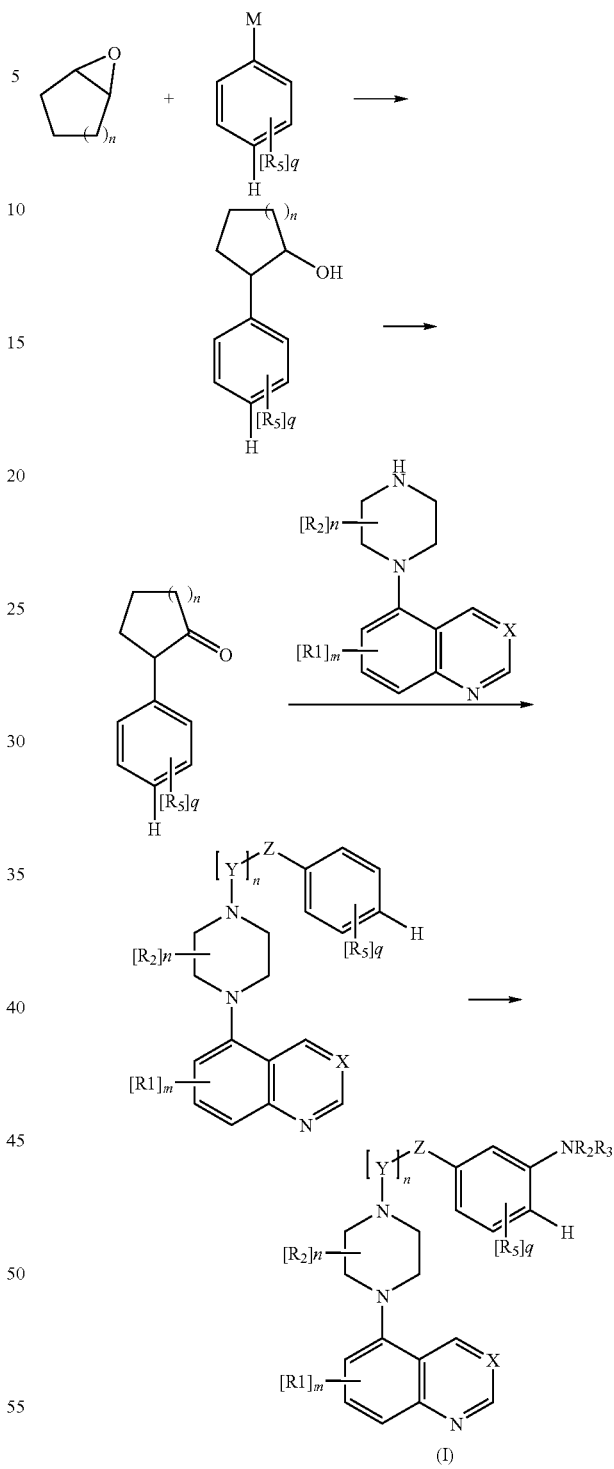

The above scheme illustrates the case where p is 0, but may be adapted for cases where p is other than 0.

Alternatively, the reaction of an aromatic nucleophile such as a Grignard reagent (M=MgX) or aryllithium (M=Li) with an α,β-unsaturated ketone (where n=1, 2), in the presence of a catalyst e.g. a copper(I) halide may provide a cycloalkyl ketone product. The ketone may then be transformed to a compound of formula (I) using methods described above.

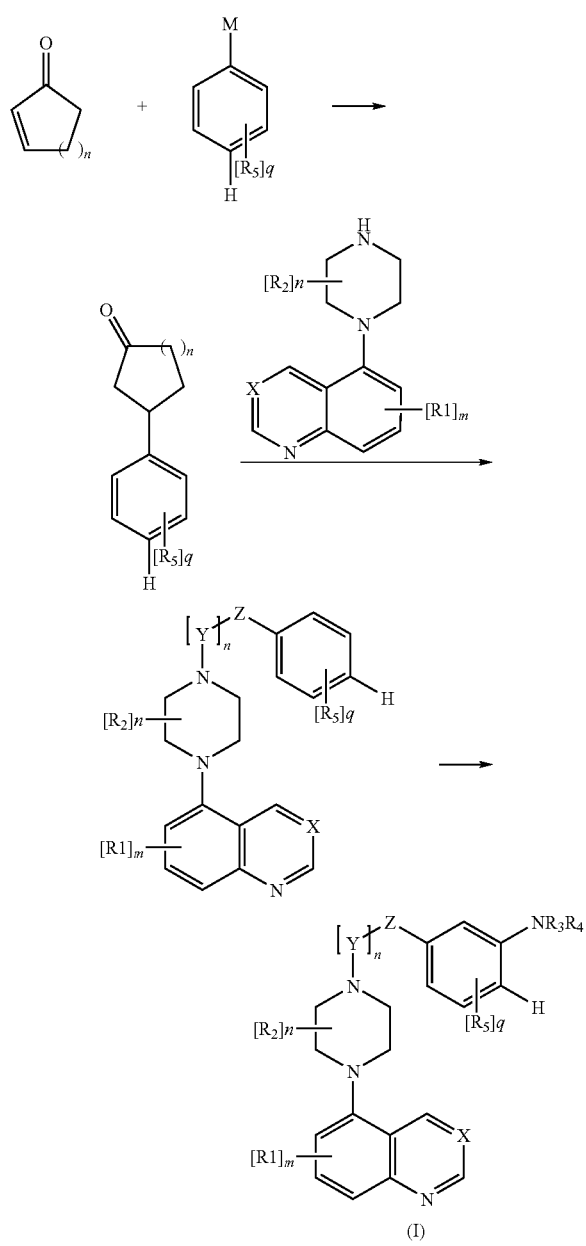

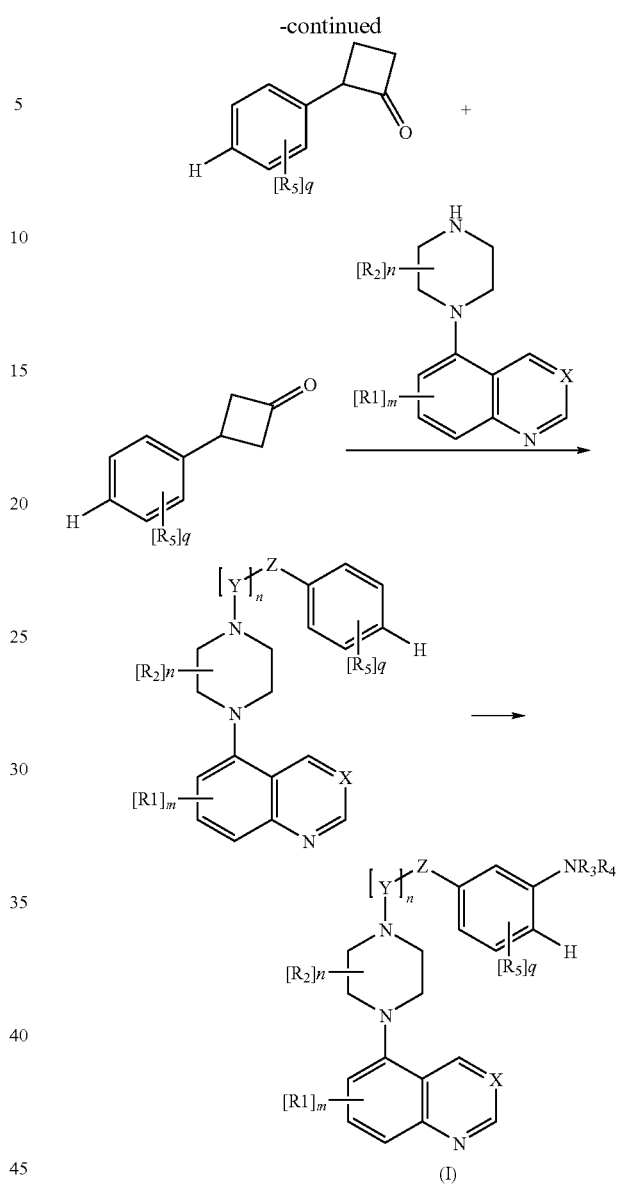

The above scheme illustrates the case where p is 0, but may be adapted for cases where p is other than 0.

Alternatively, the treatment of a substituted 2-phenyl acetyl chloride with diazomethane may produce a regioisomeric mixture of the 1,2 and 1,3-cyclobutyl ketone derivatives (Synthesis, 1977, (6), 411). The ketone regioisomers may then be transformed to a compound of formula (I) using methods described above.

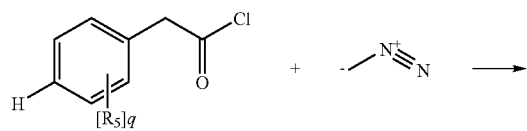

The above scheme illustrates the case where p is 0, but may be adapted for cases where p is other than 0.

Compounds of formula (I) can also be prepared according to the scheme below. Reaction of a substituted benzaldehyde with a reagent such as methoxymethyltriphenylphosphonium chloride in the presence of a suitable base, e.g. potassium carbonate or sodium methoxide or sodium hydride, produces an enol ether. The enol ether can be hydrolysed under acidic conditions, e.g. using aqueous hydrochloric acid optionally in a suitable co-solvent such as tetrahydrofuran, to give a substituted 2-phenylacetaldehyde derivative. The aldehyde can be reductively coupled to a 5-(1-piperazinyl)quinoline or quinazoline compound using conditions familiar to those skilled in the art e.g. using sodium triacetoxyborohydride or sodium cyanoborohydride. The product may be converted to a compound of formula (I) using methods described previously (if the aromatic substituents do not already include a group of formula —$NR_3R_4$).

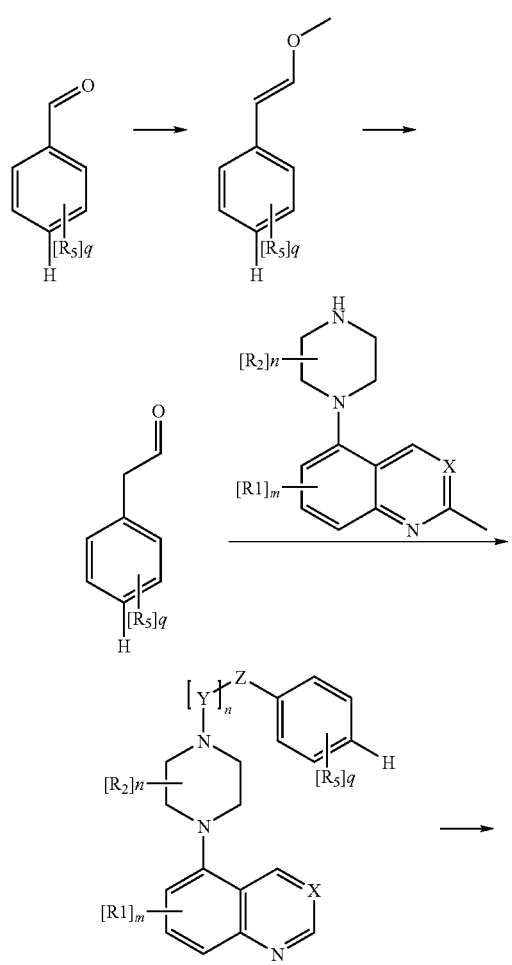

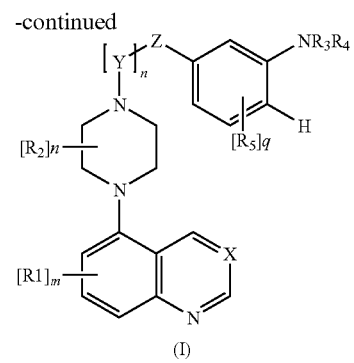

(I)

The above scheme illustrates the case where p is 0, but may be adapted for cases where p is other than 0.

Alternatively, compounds of formula (I) may be prepared according to the following scheme. Esterification of a 3-aminophenylacetic acid derivative under acidic conditions in an alcoholic solvent e.g. trimethylsilyl chloride in methanol produces the acetate ester hydrochloride. Reaction of the ester hydrochloride with a reagent such as a 2-halo-ethyl-isocyanate or a synthetic equivalent thereof, e.g. sequential addition of phosgene (or equivalent e.g. carbonyldiimidazole, disuccinimidyl carbonate) and a 2-haloethylamine ($Y=NH_2$) or 2-haloethanol ($Y=OH$), optionally in the presence of a base, produces an intermediate where X is a leaving group as defined previously. Treatment of the intermediate with a strong base, such as sodium hydride, produces a cyclised product. Reduction of the ester group with a suitable reagent, for example lithium borohydride, produces a substituted 3-phenyl ethanol derivative. Conversion of the alcohol group to a sulfonate leaving group, such as by reaction with a sulfonic anhydride or sulfonyl chloride e.g. methanesulfonyl chloride, optionally in the presence of a suitable base, produces a compound, which can be converted to a compound of formula (I) according to the procedures described previously.

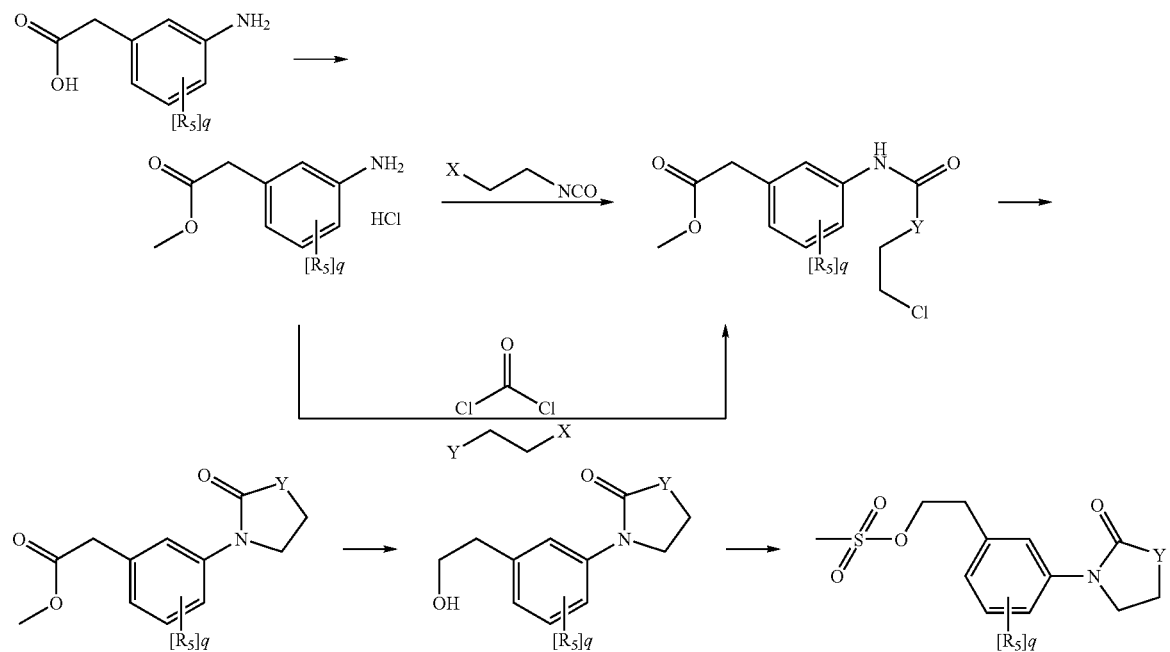

-continued

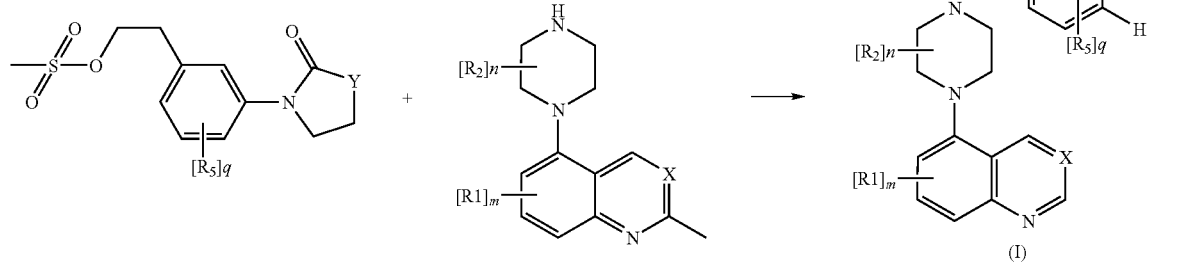

Thus, in a further aspect, this invention provides a process for the preparation of a compound of formula (I) or a pharmaceutically acceptable salt thereof, which process comprises the steps of:

(a) converting a compound of formula (III):

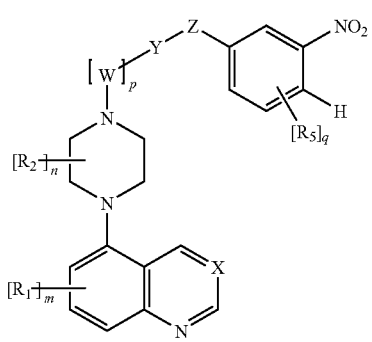

wherein $R_1$, m, X, $R_2$, n, W, p, Y, Z, $R_5$ and q are as defined for formula (I), or (b) for a compound of formula (I) wherein Y and Z form a cyclopropylene group, converting a compound of formula (IV):

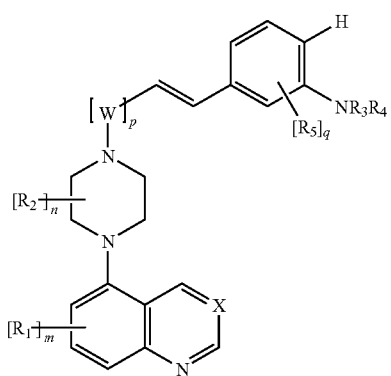

wherein $R_1$, m, X, $R_2$, n, W, p, $R_3$, $R_4$ and $R_5$ and q are as defined for formula (I); or (c) reacting a compound of formula (V):

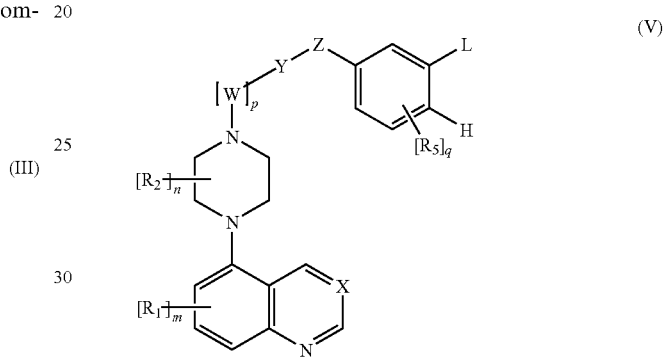

wherein $R_1$, m, X, $R_2$, n, W, p, Y, Z, $R_5$ and q are as defined for formula (I), and L is a leaving group, with a compound of formula (VI):

$$R_3R_4NH \quad (VI)$$

wherein $R_3$ and $R_4$ are as defined for formula (I); or (d) reacting a compound of formula (VII):

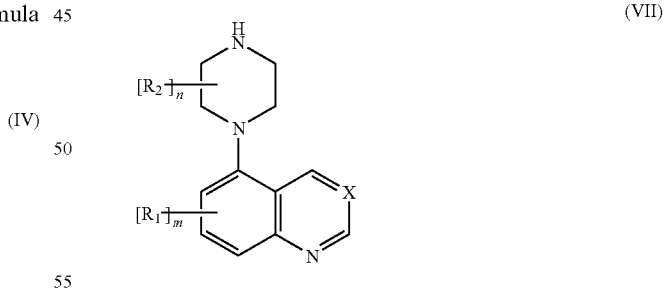

wherein $R_1$, m, X, $R_2$ and n are as defined for formula (I), with a compound of formula (VIII):

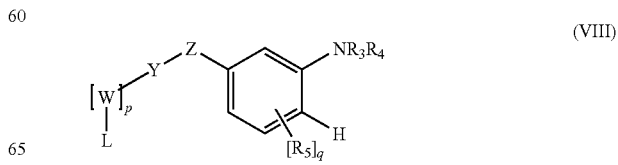

wherein W, p, Y, Z, $R_5$, q, $R_3$ and $R_4$ are as defined for formula (I), and L is a leaving group; or (e) for a compound of formula (I) wherein Z is —CH(OH), reacting a compound of formula (VII) as defined in step (d) with a compound of formula (XIII):

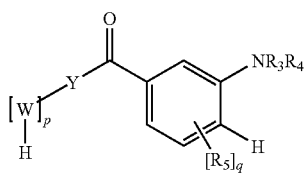

(XIII)

wherein W, p, Y, Z, $R_5$, q, $R_3$ and $R_4$ are as defined for formula (I);

or (f) for a compound of formula (I) wherein Y and Z form a $C_{3-7}$cycloalkylene group, reacting a compound of formula (VII) as defined above with a compound of formula (XIV):

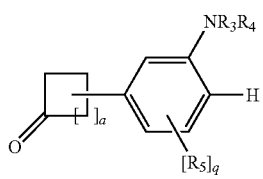

(XIV)

wherein $R_5$, $R_2$, $R_3$ and q are as defined for formula (I), a is 0, 1, 2, 3 or 4;

or (g) for a compound of formula (I) wherein the group W or Y attached to the nitrogen in the piperazine group in formula (I) is $CH_2$ or $CH(C_{1-6}alkyl)$, reacting a compound of formula (VII) as defined above with a compound of formula (XV):

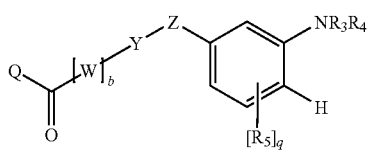

(XV)

wherein $R_3$, $R_4$, $R_5$, q, Z, Y and W are as defined for formula (I), b is 0, 1 or 2 and Q is hydrogen or $C_{1-6}$alkyl;

and thereafter optionally for any of steps (a) to (g):
  removing any protecting groups and/or
  converting a compound of formula (I) into another compound of formula (I) and/or
  forming a pharmaceutically acceptable salt.

In step (a), a compound of formula (III) is converted to form a compound of formula (I) by standard reduction reactions known to the skilled person, for example by reaction with iron and $NH_4OH$ to form a compound of formula (I) wherein $R_3$ and $R_4$ are both hydrogen. Such compounds may then be converted to other compounds of formula (I) as described below. Compounds of formula (III) may be prepared according to procedures described herein, by known literature methods, or by analogous procedures thereto.

A compound of formula (I) wherein Y and Z form a cyclopropylene group may be made by step (b), by conversion of a compound of formula (IV). As noted above, the conversion reaction may be for example a Simmons-Smith reaction. Compounds of formula (IV) may be prepared according to procedures described herein, by known literature methods, or by analogous procedures thereto. For example, compounds of formula (IV) may be made by reacting a compound of formula (VII) as defined above with a compound of formula (XVI): wherein p, W, $R_3$, $R_4$, $R_5$ and q are as defined for formula (I).

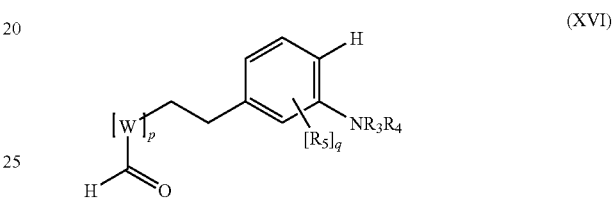

(XVI)

In step (c), a compound of formula (V) is reacted with a compound of formula (VI). The reaction may take place under conditions known to those skilled in the art, for example optionally in the presence of a copper-based catalyst. Compounds of formula (V) may be prepared according to procedures described herein, by known literature methods, or by analogous procedures thereto.

In step (d), a compound of formula (VII) is reacted with a compound of formula (VIII). Suitable reaction conditions for step (d) include the use of a base, for example triethylamine or N'N-diisopropylethylamine, in a suitable solvent such as dimethylformamide, acetonitrile, dimethylsulfoxide or N-methylpyrrolidinone with optional heating of the reaction to a temperature between 30 and 200° C., preferably between 50 and 150° C.

Suitable leaving groups for aliphatic nucleophilic substitution (J. March, Advanced Organic Chemistry, $4^{th}$ Edition, John Wiley and Sons, 1992, pp. 351-356) include, but are not limited to: halides e.g. chloro, bromo, iodo; sulfate; sulfonate esters e.g. tosylate, brosylate, nosylate and mesylate; dialkylphosphates; oxonium ions; perchlorates, betylates (ammonioalkanesulfonate esters); activated sulfonate esters e.g. fluorosulfonate, triflate, nonaflate and tresylate; halonium ions; ditosylamine; and 1-pyridinium salts.

Suitable leaving groups for aromatic substitution (J. March, Advanced Organic Chemistry, $4^{th}$ Edition, John Wiley and Sons, 1992, pp. 652-653) include, but are not limited to: halides e.g. fluoro, chloro, bromo, iodo; trialkylammonium; diazo; sulfate; sulfonate esters e.g. tosylate, brosylate, nosylate and mesylate phenylsulfanyl, phenylsulfonyl; activated sulfonate esters e.g. fluorosulfonate, triflate, nonaflate and tresylate; phosphate; dialkyl phosphate; nitro; alkoxy; aryloxy; alkylsulfonyl; and alkylsulfanyl.

Compounds of formula (VIII) may be prepared for example by converting a compound of formula (XVII):

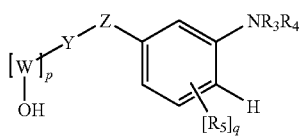

(XVII)

wherein W, p, Y, Z, $R_3$, $R_4$, $R_5$ and q are as defined for formula (I), to introduce the leaving group L by for example reacting with $MeSO_2Cl$.

The present invention provides a process for the preparation of a compound of formula (Ia) as defined above or a pharmaceutically acceptable salt thereof, which process comprises the step of reacting a compound of formula (XVIII):

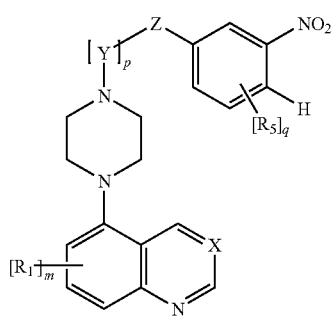

(XVIII)

wherein $R_1$, m, X, Y, p, Z, $R_5$ and q are as defined for formula (Ia) above, with compound(s) containing appropriate functional group(s) which is/are capable of reacting with a compound of formula (XVIII) to form a compound of formula (I). Compounds of formula (XVIII) may be prepared according to procedures described herein, by known literature methods, or by analogous procedures thereto.

Compounds of formula (I) can be converted into further compounds of formula (I) using standard techniques. For example, and by way of illustration rather than limitation, possible conversion reactions include acylation with an appropriate acylating agent such as acetyl chloride, alkylation using an appropriate alkylating reagent such as methyl iodide, and sulfonylation using a sulfonylating agent such as methanesulfonic anhydride. For example, for a compound of formula (I) wherein $R_3$ and $R_4$ are independently $C_{1-6}$alkylsulfonyl, a compound of formula (I) wherein $R_3$ and $R_4$ are both hydrogen may be reacted with a $C_{1-6}$alkylsulfonylchloride. For a compound of formula (I) wherein $R_3$ and $R_4$ are independently formula (II), a compound of formula (I) wherein $R_3$ and $R_4$ are both hydrogen may be reacted with a compound of formula (XIX):

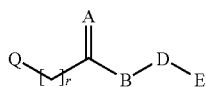

(XIX)

wherein r, A, B, D and E are as defined for formula (II) above, and Q is a suitable leaving group such as chlorine, or is —OH when r is zero. To obtain a compound of formula (I) wherein B is —$NR_8$, an appropriate isocyanate or isothiocyanate may be used. On the other hand, for compounds of formula (I) wherein $R_3R_4$, together with the nitrogen atom to which $R_3$ and $R_4$ are attached, form a 3-7 membered monocyclic heterocyclic group, an appropriate chloroformate or an isocyanate may be used to react with a compound of formula (I) wherein $R_3$ and $R_4$ are both hydrogen.

It will be appreciated by those skilled in the art that it may be necessary to protect certain reactive substituents during some of the above procedures. Standard protection and deprotection techniques, such as those described in Greene T. W. *Protective groups in organic synthesis*, New York, Wiley (1981), can be used. For example, primary amines can be protected as phthalimide, benzyl, t-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as t-butyloxycarbonyl may be removed using an acid such as hydrochloric or trifluororoacetic acid in a suitable solvent such as dichloromethane, diethylether, isopropanol or mixtures thereof.

Pharmaceutically acceptable salts may be prepared conventionally by reaction with the appropriate acid or acid derivative.

The affinities of the compounds of this invention for $5-HT_{1A}$, $5-HT_{1B}$ and $5-HT_{1D}$ receptors can be determined by the following assay. CHO cells expressing $5-HT_{1A}$ receptors ($4\times10^7$ cells/ml) are homogenised in Tris buffer and stored in 1 ml aliquots. CHO cells expressing $5-HT_{1B}$ receptors ($4\times10^7$ cells/ml) are homogenised in Tris buffer and stored in 1.5 ml aliquots. CHO cells expressing $5-HT_{1D}$ receptors ($1\times10^8$/ml) are homogenised in Tris buffer and stored in 1 ml aliquots. 0.4 ml of a cell suspension is incubated with [$^3$H]-5-HT (4 nM) for $5-HT_{1B/1D}$ receptors and [$^3$H]WAY100635 (1 nM) for $5-HT_{1A}$ receptors in Tris Mg HCl buffer (pH 7.7) and test drug, at 37° C. for 45 minutes. Each test drug is tested at 10 concentrations (0.01 mM to 0.3 nM final concentration), with non-specific binding defined using 0.01 mM 5-HT. The total assay volume is 0.5 ml. Incubation is stopped by rapid filtration using a Packard Filtermate and radioactivity measured by Topcount scintillation counting. pKi values are calculated from the $IC_{50}$ generated by an iterative least squares curve fitting programme.

Alternatively, functional potency can be measured by the following GTPγS binding protocol. Cells used in the study are Chinese Hamster Ovary (CHO) Cells, Human Embryo Kidney (HEK293). Cells were transfected with DNA coding for human receptors.

Cell Line

HEK293__5-HT1A

CHO__5-HT1B

CHO__5-HT1D

Compounds were initially dissolved in 100% Dimethyl Sulphoxide at a concentration of 10 mM. Serial dilution of drugs in 100% Dimethyl Sulphoxide were carried out using a Biomek FX. The final top concentration of compound was 3 uM in the assay. The compound at 1.0% total assay volume (TAV) was added to a solid, white, 384 well assay plate (Costar). 50% TAV of precoupled (for 90 mins @ RT) membranes, 5 ug/well, and Wheatgerm Agglutinin Polystyrene Scintillation Proximity Assay beads (RPNQ0260 Amersham International), 0.25 mg/well, in 20 mM HEPES pH 7.4, 100 mM NaCl, 3 mM MgCl$_2$ and 10 μM GDP was added. The third addition was a 20% TAV addition of either buffer, agonist format, or EC$_{80}$ final assay concentration (FAC) of agonist, 5HT antagonist format, prepared in assay buffer. The assay was started by the addition of 29% TAV of GTP S 0.38 nM FAC. After all additions assay plates were incubated at RT for 2-3 hours. Assay plates were counted on a Viewlux, 613/55 filter for 5 mins. Assay plates were read between 2-6 hours after the final addition.

The Example compounds shown below were tested and were found to have pKi values >6.0 at 5-HT$_{1A}$ receptors, with many showing a considerably higher affinity (having pKi values in the range 8.0-10.0) Certain compounds of this invention also demonstrate comparable affinity for 5-HT$_{1B}$ and 5-HT$_{1D}$ receptors.

The intrinsic activity of the compounds of this invention can be determined according to the following assay. HEK293 cell membranes stably expressing human 5-HT$_{1A}$ receptors and CHO cell membranes stably expressing human 5-HT$_{1B}$ receptors are homogenised in HEPES/EDTA buffer and stored in 1 ml aliquots, and [$^{35}$S]GTPγS binding studies are carried out essentially as described by Lazareno et al., (Life Sci., 1993, 52, 449) with some minor modifications. Membranes from 10$^6$ cells are pre-incubated at 30° C. for 30 minutes in 20 mM HEPES buffer (pH 7.4) in the presence of MgCl$_2$ (3 mM), NaCl (100 mM), GDP (10 μM) and ascorbate (0.2 mM), with or without test compounds. The reaction is started by the addition of 50 μl of [$^{35}$S]GTPγS (100 μM, assay concentration) followed by a further 30 minutes incubation at 30° C. Non-specific binding is determined using nonradiolabelled GTPγS (20 μM) added prior to the membranes. The reaction is terminated by rapid filtration through Whatman GF/B grade filters followed by 5×1 ml washes with ice cold HEPES (20 mM)/MgCl$_2$ (3 mM) buffer. Radioactivity is measured using liquid scintillation spectrometry. This procedure is hereafter referred to as the [$^{35}$S]GTPγS functional assay.

It has been found, using the [$^{35}$S]GTPγS functional assay, that certain compounds of formula (I) appear to be antagonists at 5-HT$_1$ type receptors whilst others appear to be inverse agonists, agonists or partial agonists.

The efficacy of the compounds of this invention to inhibit the re-uptake of serotonin can be measured in a 5-HT uptake assay by measurement of uptake of [$^3$H]-5-HT into LLCPK cells expressing human or rat serotonin transporters. In brief, cells are harvested and plated onto 96-well plates (10,000 cells per well). 24 hr later cells are washed 2× with HBSSH (Hanks' balanced salt solution +20 mM HEPES). 50 ul of test compound or vehicle is added to each well and incubated for 10 min. Subsequently, [$^3$H]5-HT (final concentration 25 nM) is added and the test mixture is incubated for a further 7 min. The reaction is terminated by aspiration of test mixture and the cells are washed 6× with HBSSH. 50 ul of scintillation cocktail (Microscint-20, Packard) is added onto the cells and the top and bottom of the plate is sealed. Plates are read, 30 min later, in a Packard TopCount.

Alternatively: the potency of the compounds to bind the re-uptake site of serotonin may be assessed using [3H]citalopram binding assays performed in recombinant epithelial pig kidney cells stably transfected with human SERT (hSERT/LLCPK). The cells were grown onto Petri dishes of 500 cm$^2$. At 80% of confluence the cells were harvested in phosphate buffered saline (PBS) containing 5 mM EDTA and centrifuged at 900 g for 8 min at 4° C. The pellet was homogenized in 30-50 vols of assay buffer (50 mM Tris, 120 mM NaCl, 5 mM KCl, 10 μM Pargyline, 0.1% Ascorbate (pH=7.7)) and centrifuged at 48000 g for 20 min at 4° C. The pellet was resuspended in the same volume and after incubation at 37° C. for 20 min, centrifuged as before and finally alqouted at ~0.2 mg protein/ml in cold assay buffer. [3H]citalopram binding assays consisted of 100 μl of test compound, assay buffer (to define total binding) or a final concentration of 10 μM paroxetine (to define non-specific binding), 100 μl of [3H] Citalopram at final concentration of 0.25 nM and 200 μl of membranes diluted in assay buffer at concentration of 2 μg/well of protein. Membranes were added last to initiate the reaction and incubated at room temperature for 2 h. The reaction was then stopped by rapid filtration through GF/B 96-filterplate pre-soaked in 0.5% polyethylenimmine (PEI) using a Packard cell harvester. 96-filterplate was washed 3 times with 1 ml/well cold 0.9% NaCl solution and the radioactivity was counted in Packard TopCount.

Some of the Example compounds tested according to this uptake assay were found to have potency at the uptake site of pIC$_{50}$ of >6.0.

Compounds of formula (I) and their pharmaceutically acceptable salts are of use in the treatment of certain CNS disorders such as depression (which term includes bipolar depression, unipolar depression, single or recurrent major depressive episodes with or without psychotic features, catatonic features, melancholic features, atypical features or postpartum onset, seasonal affective disorder and dysthymia, depressive disorders resulting from a general medical condition including, but not limited to, myocardial infarction, diabetes, miscarriage or abortion), anxiety disorders (which includes generalised anxiety and social anxiety disorder), schizophrenia, panic disorder, agoraphobia, social phobia, obsessive compulsive disorder, post-traumatic stress disorder, pain (particularly neuropathic pain), memory disorders (including dementia, amnesic disorders and age-associated memory impairment), disorders of eating behaviours (including anorexia nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative ipnotic, amphetamine or amphetamine-related drugs such as dextroamphetamine, methylamphetamine or a combination thereof), motor disorders such as Parkinson's disease, dementia in Parkinson's disease, neuroleptic-induced Parkinsonism and tardive dyskinesias, as well as other psychiatric disorders, and certain gastrointestinal disorders such as irritable bowel syndrome. The compounds may also be useful in treating tumours such as prostate tumours.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of a CNS disorder such as depression (which term includes bipolar depression, unipolar depression, single or recurrent major depressive episodes with or without psychotic features, catatonic features, melancholic features, atypical features or postpartum onset, seasonal affective disorder and dysthymia, depressive disorders resulting from a general medical condition including, but not limited to, myocardial infarction, diabetes, miscarriage or abortion), anxiety disorders (which includes generalised anxiety and social anxiety disorder), schizophrenia, panic disorder, agoraphobia, social phobia, obsessive compulsive disorder, post-traumatic stress disorder, pain (particularly neuropathic pain), memory disorders (including dementia, amnesic disorders and age-associated memory impairment), disorders of eating behaviours (including anorexia nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative ipnotic, amphetamine or amphetamine-related drugs such as dextroamphetamine, methylamphetamine or a combination thereof), motor disorders such as Parkinson's disease, dementia in Parkinson's disease, neuroleptic-induced Parkinsonism and tardive dyskinesias, as well as other psychiatric disorders, and certain gastrointestinal disorders such as irritable bowel syndrome, and tumours such as prostate tumours.

In particular the invention provides a compound of formula (I) or a pharmaceutically acceptable salt thereof for use as a therapeutic substance in the treatment of depression and/or anxiety.

Compounds of the invention may be administered in combination with other active substances such as 5HT3 antagonists, serotonin agonists, NK-1 antagonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination or composition may be administered simultaneously (either in the same or different pharmaceutical formulations), separately or sequentially.

The invention further provides a method of treatment of the above disorders in mammals including humans, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the above disorders.

In order to use the compounds of formula (I) in therapy, they will normally be formulated into a pharmaceutical composition in accordance with standard pharmaceutical practice.

The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants lubricants (e.g. magnesium stearate, talc or silica), disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Preparations and Examples illustrate the compounds of the present invention and preparation thereof.

Description 1

2-Methyl-5-quinolinyl trifluoromethanesulfonate (D1)

A solution of 2-methyl-quinolin-5-ol (2.5 g; 1 eq) in dichloromethane (25 mL) and pyridine (6.4 mL; 5 eq) was cooled to 0° C. and trifluoromethanesulfonic anhydride (4.2 mL; 1.6 eq) was added dropwise over 10 minutes. The reaction mixture was stirred under an inert atmosphere at r.t. for 1 h, then poured into water (20 mL) and extracted into ethyl acetate (3×15 mL). The organic layers were combined, dried over $Na_2SO_4$ and concentrated under reduced pressure. The crude was purified by flash chromatography, eluting with ethyl acetate/cyclohexane (4/6) affording the title compound in 92% yield (4.2 g).

MS; (ES) m/z: 292.3 [MH$^+$]. $C_{11}H_8F_3NO_3S$ requires 291.
$^1$H-NMR (300 MHz, d$_6$-DMSO) δ(ppm): 8.05 (d, 1H), 7.85 (d, 1H), 7.64 (t, 1H), 7.48 (d, 1H), 7.43 (d, 1H), 2.48 (s, 3H).

Description 2

1,1-Dimethylethyl 4-(2-methyl-5-quinolinyl)-1-piperazinecarboxylate (D2)

tert-Butyl 1-piperazine carboxylate (1.6 g; 1.2 eq), cesium carbonate (1.7 g; 1.5 eq), palladium acetate (0.33 g; 0.14 eq) and 2,2'-bis(diphenylphosphino)-1,1'-binaphthyl (0.97 mg; 0.15 eq) were added to a solution of 2-methyl-5-quinolinyl trifluoromethanesulfonate (D1) in toluene (20 mL) under an inert atmosphere. The reaction mixture was stirred at reflux under nitrogen for 8 hours. The reaction was quenched at room temperature using a saturated aqueous solution of ammonium chloride (15 mL) and extracted into ethyl acetate (3×20 mL). The organic layers were combined, dried over $Na_2SO_4$ and concentrated under reduced pressure. The crude was purified by flash chromatography, eluting with ethyl acetate/cyclohexane (3/7) affording the title compound in 62% yield (1.4 g).

MS; (ES) m/z: 328.4 [MH]$^+$. $C_{19}H_{25}N_3O_2$ requires 327.
$^1$H-NMR (500 MHz, CDCl$_3$) δ(ppm): 8.40 (d, 1H), 7.76 (d, 1H), 7.61 (t, 1H), 7.29 (d, 1H), 7.06 (d, 1H), 3.69 (bs, 4H), 3.03 (bs, 4H), 2.74 (s, 3H), 1.51 (s, 9H).

Description 3

2-Methyl-5-(1-piperazinyl)quinoline (D3)

1,1-dimethylethyl 4-(2-methyl-5-quinolinyl)-1-piperazinecarboxylate (D2) (1.1 g) in a 25% solution of trifluoroacetic acid in dichloromethane (10 mL) was stirred at r.t. under an inert atmosphere for 3 hours. The reaction mixture was concentrated under reduced pressure and desalted by means of a 20 g SCX cartridge affording the title compound in 96% yield (0.74 g).

MS; (ES) m/z: 228.4 [MH]$^+$. $C_{14}H_{17}N_3$ requires 227.
$^1$H-NMR (300 MHz, d$_6$-DMSO) δ(ppm): 8.34 (d, 1H), 7.57 (m, 2H), 7.35 (m, 1H), 7.06 (m, 1H), 2.93 (bm, 8H), 2.62 (s, 3H).

Description 4

2-(3-Nitrophenyl)ethyl methanesulfonate (D4)

Methanesulfonyl chloride (0.28 mL) was added dropwise to a stirred solution of 2-(3-nitrophenyl)ethanol (0.5 g; 1 eq) in dichloromethane (3 mL) and triethylamine (0.5 mL; 1.2 eq) at 0° C. under an inert atmosphere. The solution was allowed to reach r.t. and stirred for 5 hours. The reaction mixture was diluted with water (3 mL) and extracted into dichloromethane (3×3 mL). The organic layers were combined, dried over $Na_2SO_4$ and concentrated under reduced pressure. The crude was purified by flash chromatography, eluting with a gradient from dichloromethane to dichloromethane/MeOH (98/2) affording the title compound in 84% yield (0.62 g).

¹H-NMR (300 MHz, CDCl₃) δ(ppm): 8.15 (m, 2H), 7.53 (m, 2H), 4.45 (t, 2H), 3.15 (t, 2H), 2.92 (s, 3H).

Description 5

2-Methyl-5-{4-[2-(3-nitrophenyl)ethyl]-1-piperazinyl}quinoline (D5)

N,N-Diisopropylethylamine (0.8 mL; 5 eq) was added to a solution of 2-methyl-5-(1-piperazinyl)quinoline (D3) (0.2 g; 1 eq) and 2-(3-nitrophenyl)ethyl methanesulfonate (D4) (0.22; 1 eq) in dimethylformamide (1.5 mL). The reaction mixture was heated to 100° C. for 10 hours. The dark solution was concentrated under reduced pressure, diluted with water (3 mL) and brine (1 mL) and extracted into ethyl acetate (3×3 mL). The organic layers were combined, dried over $Na_2SO_4$ and concentrated under reduced pressure. The crude was purified by flash chromatography, eluting with a gradient from dichloromethane to dichloromethane/MeOH (98/2) affording the title compound in 64% yield (0.21 g).

MS; (ES) m/z: 228.4 [MH]⁺. $C_{22}H_{24}N_4O_2$ requires 376.
¹H-NMR (300 MHz, CDCl₃) δ(ppm): 8.35 (d, 1H), 8.11 (s, 1H), 8.05 (d, 1H), 7.70 (d, 1H), 7.55 (m, 2H), 7.45 (t, 1H), 7.25 (m, 1H), 7.05 (d, 1H), 3.10 (mt, 4H), 2.95 (bm, 2H), 2.75 (bm, 6H), 2.70 (s, 3H).

Description 6

3-{2-[4-(2-Methyl-5-quinolinyl)-1-piperazinyl]ethyl}aniline (D6)

A solution of 2-methyl-5-{4-[2-(3-nitrophenyl)ethyl]-1-piperazinyl}quinoline (D5) (0.14 g; 1 eq) in methanol (3 mL) was added dropwise to a suspension of iron powder (0.07 g; 3.2 eq) and ammonium chloride (0.1 g; 5.3 eq) in water (3 mL). The reactants were heated at reflux for 8 hours, adding additional amounts of iron powder (total 0.07 g; 3.2 eq) and ammonium chloride (total 0.1 g; 5.03 eq) in 3 portions during the reaction. The reaction mixture was filtered using a Millipore filter. The filtrate was concentrated under reduced pressure, diluted with water (5 mL) and a saturated aqueous solution of sodium hydrogen carbonate (2 mL), extracted into ethyl acetate (3×5 mL), dried over $Na_2SO_4$ and concentrated under reduced pressure obtaining the title compound in 84% yield (0.11 g).

MS; (ES) m/z: 347.4 [MH]⁺. $C_{22}H_{26}N_4$ requires 346.
¹H-NMR (300 MHz, CDCl₃) δ(ppm): 8.35 (d, 1H), 7.70 (d, 1H), 7.55 (t, 1H), 7.25 (d, 1H), 7.08 (m, 2H), 6.65 (md, 1H), 6.55 (m, 2H), 3.65 (bs, 2H), 3.15 (t, 4H), 2.80 (m, 4H), 2.75 (s, 3H), 2.70 (m, 4H).

Description 7

N-Methyl-3-{2-[4-(2-methyl-5-quinolinyl)-1-piperazinyl]ethyl}aniline (D7)

Propyl (3-{2-[4-(2-methyl-5-quinolinyl)-1-piperazinyl]ethyl}phenyl)carbamate dihydrochloride (E47) (0.065 mmol) was charged onto an SPE cartridge (SCX) and eluted with a solution of ammonia in MeOH to obtain the corresponding free base (0.0618 mmol). This was then dissolved in tetrahydrofuran (1 ml) and treated with LiAlH₄ (3 equiv.). The resulting reaction mixture was warmed to 70° C. and stirred for 3 h. Then, the reaction mixture was poured into NH₄Cl aq. at 0° C. The aqueous phase was extracted with dichloromethane (20 ml). The organic phases were washed with water, dried over $Na_2SO_4$ and concentrated under reduced pressure. The crude was purified on SPE cartridge (Silica) using CH₂Cl₂/MeOH (98/2) as eluent to give the title compound in 43% yield.

MS: (ES/+) m/z: 361 [MH⁺]. $C_{23}H_{28}N_4$ required 360.
¹H-NMR (300 MHz, CDCl₃) δ(ppm): 8.35 (1H, d), 7.70 (1H, d), 7.65 (1H, t), 7.15-7.00 (2H, m), 6.55 (1H, d), 6.50-6.40 (2H, m) 3.15 (4H, m), 2.85-2.65 (8H, m), 2.80 (3H, s), 2.70 (3H, s).

Description 8

1-(3-Aminophenyl)-2-[4-(2-methyl-5-quinolinyl)-1-piperazinyl]ethanol (D8)

Sodium carbonate (1.5 eq) and 2-bromo-1-(3-nitrophenyl)ethanone (1.5 eq) were added to a stirred solution of 2-methyl-5-(1-piperazinyl)quinoline (D3) (1 eq) in tetrahydrofuran at room temperature under an inert atmosphere, and the reaction was left under stirring for 1 h. The solution was then diluted with MeOH, NaBH₄ (2 eq) was added and the reaction was left under stirring for 1 h. The solvent was removed under reduced pressure. The crude material was purified on SPE cartridge (SCX) using as eluant a gradient from MeOH to MeOH:CH₂Cl₂ (1:1) and then 2M NH₃ in MeOH affording an intermediate which was reduced following a similar procedure to D6 to give the title compound in 55% yield.

MS: (ES/+) m/z: 363 [MH⁺]. $C_{22}H_{26}N_4O$ required 362.
¹H-NMR (300 MHz, CDCl₃) δ(ppm): 8.35 (1H, d), 7.70 (1H, d), 7.55 (1H, t), 7.25 (1H, d), 7.10 (1H, t), 7.05 (1H, d), 6.80-6.70 (2H, m), 6.60 (1H, dd), 4.70 (1H, dd), 3.65 (2H, bs), 3.15 (4H, bs), 3.00 (2H, bm), 2.80-2.50 (7H, m).

General Procedure for the Preparation of Amides, Ureas and Carbamates Starting from Arylbromides: Method A K₂CO₃ (1.5 eq), an amide, urea or carbamate (2 eq), CuI (0.1 eq) and N,N'-dimethyl-1,2-ethanediamine (0.11 eq) were added to a stirred solution of an arylbromide (1 eq) in dioxane at room temperature under an inert atmosphere, and the reaction was heated at 90-100° C. for 1-5 hrs. The mixture was then added to a saturated aqueous solution of NH₄Cl, and extracted with dichloromethane. The organic phase was washed with brine, dried over $Na_2SO_4$ and the solvent was removed under reduced pressure. The crude material was purified on SPE cartridge (Silica) using as eluant Cyclohexane/ethyl acetate 8:2, affording the final compound (yields ranged from 18 to 99%).

Description 9

1-(3-Acetylphenyl)-2-pyrrolidinone (D9)

The title compound was prepared in 98% yield according to the general procedure for the preparation of the amides, ureas and carbamates (Method A) starting from 1-(3-bromophenyl)ethanone and 2-pyrrolidinone.

MS: (ES) m/z: 204 [MH⁺]. $C_{12}H_{13}NO_2$ requires 203.
¹H-NMR (300 MHz, CDCl₃) δ(ppm): 8.15 (bs, 1H), 8.0 (dd, 1H), 7.7 (dd, 1H), 7.45 (t, 1H), 3.95 (t, 2H), 2.65 (m, 2H), 2.60 (s, 3H), 2.2 (m, 2H).

Description 10

1-(3-Acetylphenyl)-2-azetidinone (D10)

The title compound was prepared in 97% yield according to the general procedure for the preparation of the amides, ureas and carbamates (Method A) starting from 1-(3-bromophenyl)ethanone and 2-azetidinone.

MS: (ES) m/z: 190 [MH$^+$]. $C_{11}H_{11}NO_2$ requires 189.

$^1$H-NMR (300 MHz, CDCl$_3$) δ(ppm): 7.6 (d, 1H); 7.55 (dd, 1H); 7.45 (dd, 1H); 7.2 (t, 1H); 3.5 (t, 2H), 3.0 (t. 2H), 2.45 (s, 3H)

Description 11

3-(3-Acetylphenyl)-1,3-oxazolidin-2-one (D11)

The title compound was prepared in quantitative yield according to the general procedure for the preparation of the amides, ureas and carbamates (Method A) starting from 1-(3-bromophenyl)ethanone and 1,3-oxazolidin-2-one.

MS: (ES) m/z: 206 [MH$^+$]. $C_{11}H_{11}NO_3$ requires 205.

$^1$H-NMR (300 MHz, CDCl$_3$) δ(ppm): 7.95 (m, 2H), 7.7 (dd, 1H), 7.45 (t, 1H), 4.5 (t, 2H), 4.2 (t, 2H), 2.6 (s, 3H)

Description 12

1-(3-Acetylphenyl)-2-imidazolidinone (D12)

The title compound was prepared in 18% yield according to the general procedure for the preparation of the amides, ureas and carbamates (Method A) starting from 1-(3-bromophenyl)ethanone and 2-imidazolidinone.

MS: (ES) m/z: 205 [MH$^+$]. $C_{11}H_{12}N_2O_2$ requires 204.

$^1$H-NMR (300 MHz, CDCl$_3$) δ(ppm): 7.8 (m, 2H), 7.54 (dd, 1H), 7.25 (t, 1H), 5.0 (bs, 1H), 3.8 (t, 2H), 3.4 (t, 2H), 2.45 (s, 3H).

Description 13

2-(3-Bromophenyl)ethyl methanesulfonate (D13)

The title compound was prepared in 77% yield using a similar procedure to description D4 starting from 2-(3-bromophenyl)ethanol.

MS: (ES/+) m/z: 278 and 280 [MH$^+$]. $C_9H_{11}BrO_3S$ requires 277 and 279.

$^1$H-NMR (200 MHz, CDCl$_3$) δ(ppm): 7.40 (2H, m), 7.5 (2H, m), 4.40 (2H, t), 3.00 (2H, t), 2.85 (3H, s).

Description 14

5-{4-[2-(3-Bromophenyl)ethyl]-1-piperazinyl}-2-methylquinoline (D14)

The title compound was prepared in 56% yield using a similar procedure to description D5 starting from 2-methyl-5-(1-piperazinyl)quinoline (D3) and 2-(3-bromophenyl)ethyl methanesulfonate (D13).

MS: (ES/+): m/z: 412 and 410 [MH$^+$]. $C_{22}H_{14}BrN_3$ requires 409 and 411.

$^1$H-NMR (400 MHz, CDCl$_3$) δ(ppm): 8.29 (1H, d), 7.54 (2H, m), 7.35 (1H, br m), 7.34 (1H, d), 7.23 (2H, m), 7.06 (1H, dd), 2.98 (4H, br s), 2.76 (2H, br t), 2.68 (5H, br s), 2.59 (2H, br m), 2.58 (3H, s).

Description 15

2-(3-Nitrophenyl)ethyl 4-nitrobenzenesulfonate (D15)

The title compound was prepared in 68% yield using a similar procedure to description D4 starting from 2-(3-nitrophenyl)ethanol and 4-nitrobenzenesulfonyl chloride.

MS: (ES) m/z: 351 [MH$^+$]. $C_{14}H_{12}N_2O_7S$ requires 352.

$^1$H-NMR (300 MHz, CDCl$_3$) δ(ppm): 8.3 (m, 2H), 8.05 (d, 1H), 8.0-7.9 (m, 3H), 7.5 (m, 2H), 4.4 (t, 2H), 3.1 (t, 2H).

Description 16

7-Chloro-2-methyl-5-(1-piperazinyl)quinoline (D16)

The title compound was prepared from 7-chloro-5-hydroxy-2-methylquinoline (WO/0234754) using similar procedures to descriptions D1, D2 and D3.

MS; (ES) m/z: 262.1 [MH]$^+$. $C_{14}H_{16}ClN_3$ requires 261.

$^1$H-NMR (300 MHz, d$_6$-DMSO) δ(ppm): 8.36 (d, 1H), 7.61 (d, 1H), 7.40 (d, 1H), 6.92 (d, 1H, 3.32 (m, 4H), 2.93 (m, 4H), 2.62 (s, 3H).

Description 17

7-Chloro-2-methyl-5-{4-[2-(3-nitrophenyl)ethyl]-1-piperazinyl}quinoline (D17)

The title compound was prepared in 92% yield using a similar procedure to description D5 starting from 7-chloro-2-methyl-5-(1-piperazinyl)quinoline (D16) and 2-(3-Nitrophenyl)ethyl 4-nitrobenzenesulfonate (D15).

MS: (ES) m/z: 411 [MH$^+$]. $C_{22}H_{23}ClN_4O_2$ requires 410.

$^1$H-NMR (300 MHz, CDCl$_3$) δ(ppm): 8.3 (d, 1H), 8.2 (bd, 1H), 8.05 (bd, 1H), 7.7 (s, 1H), 7.55 (d, 1H), 7.4 (t, 1H), 7.2 (d, 1H), 6.95 (s, 1H), 3.1 (bm, 4H), 2.95 (t, 2H), 2.8-2.6 (bm, 6H), 2.6 (s, 3H)

Description 18

3-{2-[4-(7-Chloro-2-methyl-5-quinolinyl)-1-piperazinyl]ethyl}aniline (D18)

The title compound was prepared in 92% yield using a similar procedure to description D6 starting from 7-Chloro-2-methyl-5-{4-[2-(3-nitrophenyl)ethyl]-1-piperazinyl}quinoline (D17).

MS: (ES) m/z: 381 [MH$^+$]. $C_{22}H_{25}ClN_4$ requires 380.

$^1$H-NMR (300 MHz, CDCl$_3$) δ(ppm): 8.25 (d, 1H), 7.65 (s, 1H), 7.2 (d, 1H), 7.05 (t, 1H), 6.95 (s, 1H), 6.6 (d, 1H), 6.5 (m, 2H), 3.6 (bs, 2H), 2.8-2.5 (m, 12H), 2.65 (s, 3H)

Description 19

[3-(1H-Pyrazol-1-yl)phenyl]acetic acid (D19)

Pyrazole (1.2 eq), Cs$_2$CO$_3$ (2.5 eq), CuI (0.5 eq), trans-1,2-cyclohexanediamine (0.6 eq) and dodecane (1 eq), were added to a stirred solution of 3-bromophenylacetic acid (1 eq) in dioxane at room temperature under an inert atmosphere. The mixture was irradiated in a microwave reactor (PersonalChemistry Emrys™ Optimiser, 300 W, 160° C., 20 min), then added to a 1N aqueous solution of NaOH, and extracted with Et$_2$O. The aqueous phase was acidified to pH=3 with HCl 2N, then extracted with ethyl acetate; this phase was washed with brine, dried over Na$_2$SO$_4$ and the solvent was removed under reduced pressure. The crude material was purified on SPE cartridge (Silica) eluting with a gradient from Cyclohexane/ethyl acetate 8:2, to Cyclohexane/ethyl acetate 1:1, affording the title compound in 65% yield.

MS: (ES) m/z: 203 [MH$^+$]. $C_{11}H_{10}N_2O_2$ requires 202.

$^1$H-NMR (300 MHz, CDCl$_3$) δ(ppm): 7.9 (m, 1H), 7.75 (m, 1H), 7.65 (m, 1H), 7.55 (d, 1H), 7.35 (t, 1H), 7.3-7.1 (m, 2H), 6.55 (m, 1H), 3.7 (s, 2H)

EXAMPLES

General Procedure for the Preparation of Amides Starting from 3-{2-[4-(2-methyl-5-quinolinyl)-1-piperazinyl]ethyl}aniline (D6): Method B Triethylamine or diisopropylethylamine (1.7 eq) and then an acyl chloride (1.5 eq) were added dropwise to a stirred solution of 3-{2-[4-(2-methyl-5-quinolinyl)-1-piperazinyl]ethyl}aniline (D6) (1 eq) in dichloromethane at room temperature under an inert atmosphere. The reaction was left under stirring for 16 h. The mixture was then washed with a saturated aqueous solution of $NH_4Cl$, a saturated aqueous solution of $NaHCO_3$, brine, dried over $Na_2SO_4$ and the solvent was removed under reduced pressure. The crude material was purified on SPE cartridge (Silica) using as eluent a gradient from dichloromethane/MeOH 99/1 to dichloromethane/MeOH 98/2 affording the final compound (yields ranged from 30 to 80%).

General Procedure for the Preparation of Amides and their Corresponding Dihydrochloride Salts Starting from 3-{2-[4-(2-methyl-5-quinolinyl)-1-piperazinyl]ethyl}aniline (D6): Method C EDC•HCl (1.5 eq) and HOBt (1.5 eq) were added sequentially to a stirred solution of a carboxylic acid (1.5 eq) in dichloromethane/dimethylformamide (1/1) at room temperature. The reaction mixture was left under stirring for 30 min then 3-{2-[4-(2-methyl-5-quinolinyl)-1-piperazinyl]ethyl}aniline (D6) (1 eq) dissolved in dichloromethane/dimethylformamide (1/1) was added dropwise. The solution was stirred for 16 h then diluted with dichloromethane and washed with a saturated aqueous solution of $NaHCO_3$ and brine and then dried over $Na_2SO_4$. The solution was concentrated under reduced pressure and the residual solvent was removed by means of an SCX cartridge. The crude material was purified on SPE cartridge (Silica) eluting from a gradient from dichloromethane/MeOH 99/1 to dichloromethane/MeOH 98/2 affording the final compound (yields ranged from 20 to 96%).

The free base could be converted into its dihydrochloride salt by dissolving the compound in dichloromethane and adding a 1M ethereal solution of HCl (2.1 eq) dropwise. A yellow solid precipitated and the suspension was stirred for 15 min. The solvent was removed under reduced pressure affording a crude material which was triturated with $Et_2O$. The final compound was then recovered by filtration (yield quantitative).

Example 1

N-(3-{2-[4-(2-Methyl-5-quinolinyl)-1-piperazinyl]ethyl}phenyl)acetamide (E1)

The title compound was prepared in 52% yield according to the general procedure for the preparation of the amides (Method B) starting from 3-{2-[4-(2-methyl-5-quinolinyl)-1-piperazinyl]ethyl}aniline (D6) and acetyl chloride.

MS: (ES) m/z: 389 [MH]$^+$. $C_{24}H_{28}N_4O$ requires 388.

$^1$H-NMR (500 MHz, $d_6$-DMSO) δ(ppm): 9.84 (s, 1H), 8.33 (d, 1H), 7.58 (m, 2H), 7.46 (s, 1H), 7.39 (m, 2H), 7.19 (t, 1H), 7.10 (dd, 1H), 6.92 (d, 1H), 3.03 (bm, 4H), 2.73 (bm, 6H), 2.62 (s+bm, 5H), 2.02 (s, 3H).

Example 2

N-(3-{2-[4-(2-Methyl-5-quinolinyl)-1-piperazinyl]ethyl}phenyl)propanamide (E2)

The title compound was prepared in 73% yield according to the general procedure for the preparation of the amides (Method B) starting from 3-{2-[4-(2-methyl-5-quinolinyl)-1-piperazinyl]ethyl}aniline (D6) and propanoyl chloride.

MS: (ES/+) m/z: 403 [MH$^+$]. $C_{25}H_{30}N_4O$ requires 402.

$^1$H-NMR (300 MHz, CDCl$_3$) δ(ppm): 8.35 (d, 1H), 7.70 (d, 1H), 7.55 (t, 1H), 7.50 (br s, 1H), 7.25 (m, 3H), 7.12 (br, 1H), 7.07 (d, 1H), 6.98 (br d, 1H), 3.20 (br m, 4H), 3.00-2.75 (br m, 8H), 2.73 (s, 3H), 2.37 (q, 2H), 1.23 (t, 3H)

Example 3

2-Methyl-N-(3-{2-[4-(2-methyl-5-quinolinyl)-1-piperazinyl]ethyl}phenyl) propanamide (E3)

The title compound was prepared in 81% yield according to the general procedure for the preparation of the amides (Method B) starting from 3-{2-[4-(2-methyl-5-quinolinyl)-1-piperazinyl]ethyl}aniline (D6) and 2-methylpropanoyl chloride.

MS: (ES/+) m/z: 417 [MH$^+$]. $C_{26}H_{32}N_4O$ requires 416.

$^1$H-NMR (300 MHz, CDCl$_3$) δ(ppm): 8.35 (d, 1H), 7.70 (d, 1H), 7.55 (m, 2H), 7.25 (m, 3H), 7.13 (br s, 1H), 7.08 (d, 1H), 6.98 (br d, 1H), 3.20 (br m, 4H), 3.00-2.75 (br m, 8H), 2.73 (s, 3H), 2.48 (m, 1H), 1.25 (d, 6H)

Example 4

3-Methyl-N-(3-{2-[4-(2-methyl-5-quinolinyl)-1-piperazinyl]ethyl}phenyl) butanamide (E4)

The title compound was prepared in 64% yield according to the general procedure for the preparation of the amides (Method B) starting from 3-{2-[4-(2-methyl-5-quinolinyl)-1-piperazinyl]ethyl}aniline (D6) and 3-methylbutanoyl chloride.

MS: (ES/+) m/z: 431 [MH$^+$]. $C_{27}H_{34}N_4O$ requires 430.

$^1$H-NMR (300 MHz, CDCl$_3$) δ(ppm): 8.35 (d, 1H), 7.70 (d, 1H), 7.60-7.50 (m, 2H), 7.30-7.20 (m, 3H), 7.10 (d, 2H), 7.00 (d, 1H), 3.20 (br s, 4H), 3.00-2.80 (br m, 8H), 2.70 (s, 3H), 2.20 (m, 3H), 1.00 (d, 6H).

Example 5

2,2-Dimethyl-N-(3-{2-[4-(2-methyl-5-quinolinyl)-1-piperazinyl]ethyl}phenyl) propanamide (E5)

The title compound was prepared in 66% yield according to the general procedure for the preparation of the amides (Method B) starting from 3-{2-[4-(2-methyl-5-quinolinyl)-1-piperazinyl]ethyl}aniline (D6) and 2,2-dimethylpropanoyl chloride.

MS: (ES/+) m/z: 431 [MH$^+$]. $C_{27}H_{34}N_4O$ requires 430.

$^1$H-NMR (300 MHz, CDCl$_3$) δ(ppm): 8.35 (d, 1H), 7.70 (d, 1H), 7.55 (t, 2H), 7.30-7.20 (m, 4H), 7.10 (d, 1H), 7.00 (m, 1H), 3.20 (br s, 4H), 2.85 (br s, 8H), 2.70 (s, 3H), 1.30 (s, 9H)

Example 6

N-(3-{2-[4-(2-Methyl-5-quinolinyl)-1-piperazinyl]ethyl}phenyl)benzamide (E6)

The title compound was prepared in 60% yield according to the general procedure for the preparation of the amides (Method B) starting from 3-{2-[4-(2-methyl-5-quinolinyl)-1-piperazinyl]ethyl}aniline (D6) and benzoyl chloride.

MS: (ES/+) m/z: 451 [MH$^+$]. $C_{29}H_{30}N_4O$ requires 450.

$^1$H-NMR (300 MHz, CDCl$_3$) δ(ppm): 8.35 (d, 1H), 7.87 (m, 2H), 7.80 (br s, 1H), 7.72 (d, 1H), 7.65 (br s, 1H), 7.6-7.4 (m, 5H), 7.30 (t, 1H), 7.27 (m, 1H), 7.08 (d, 1H), 7.05 (d, 1H), 3.18 (br s, 4H), 3.00-2.75 (br m, 8H), 2.72 (s, 3H).

Example 7

N-(3-{2-[4-(2-Methyl-5-quinolinyl)-1-piperazinyl]ethyl}phenyl)-2-phenyl acetamide (E7)

The title compound was prepared in 64% yield according to the general procedure for the preparation of the amides (Method B) starting from 3-{2-[4-(2-methyl-5-quinolinyl)-1-piperazinyl]ethyl}aniline (D6) and phenylacetyl chloride.

MS: (ES/+) m/z: 465 [MH$^+$]. $C_{30}H_{32}N_4O$ requires 464.

$^1$H-NMR (300 MHz, CDCl$_3$) δ(ppm): 8.35 (d, 1H), 7.70 (d, 1H), 7.55 (t, 1H), 7.45-7.15 (m, 9H), 7.10-6.95 (m, 3H), 3.70 (s, 2H), 3.10 (br s, 4H), 2.90-2.70 (br s, 8H), 2.70 (s, 3H).

Example 8

3,3-Dimethyl-N-(3-{2-[4-(2-methyl-5-quinolinyl)-1-piperazinyl]ethyl}phenyl) butanamide (E8)

The title compound was prepared in 62% yield according to the general procedure for the preparation of the amides (Method B) starting from 3-{2-[4-(2-methyl-5-quinolinyl)-1-piperazinyl]ethyl}aniline (D6) and 3,3-dimethylbutanoyl chloride.

MS: (ES/+) m/z: 445 [MH$^+$]. $C_{28}H_{36}N_4O$ requires 444.

$^1$H-NMR (300 MHz, CDCl$_3$) δ(ppm): 8.35 (d, 1H), 7.70 (d, 1H), 7.60-7.45 (m, 2H), 7.30-7.20 (m, 3H), 7.15-7.05 (m, 2H), 7.00 (d, 1H), 3.10 (t, 4H), 2.90-2.60 (m, 8H), 2.65 (s, 3H), 2.20 (s, 2H), 1.05 (s, 9H).

Example 9

N-(3-{2-[4-(2-Methyl-5-quinolinyl)-1-piperazinyl]ethyl}phenyl)cyclohexane carboxamide (E9)

The title compound was prepared in 30% yield according to the general procedure for the preparation of the amides (Method B) starting from 3-{2-[4-(2-methyl-5-quinolinyl)-1-piperazinyl]ethyl}aniline (D6) and cyclohexanecarbonyl chloride.

MS: (ES/+) m/z: 457 [MH$^+$]. $C_{29}H_{36}N_4O$ requires 456.

$^1$H-NMR (300 MHz, CDCl$_3$) δ(ppm): 8.35 (d, 1H), 7.70 (d, 1H), 7.60-7.50 (m, 2H), 7.30-7.20 (m, 3H), 7.15-7.05 (m, 2H), 7.00 (d, 1H), 3.15 (br s, 4H), 2.95-2.75 (m, 8H), 2.70 (s, 3H), 2.20-1.40 (m, 7H), 1.40-1.10 (m, 4H).

Example 10

5-Methyl-N-(3-{2-[4-(2-methyl-5-quinolinyl)-1-piperazinyl]ethyl}phenyl)-3-isoxazolecarboxamide (E10)

The title compound was prepared in 40% yield according to the general procedure for the preparation of the amides (Method B) starting from 3-{2-[4-(2-methyl-5-quinolinyl)-1-piperazinyl]ethyl}aniline (D6) and 5-methyl-3-isoxazolecarbonyl chloride.

MS: (ES/+) m/z: 456 [MH$^+$]. $C_{27}H_{29}N_5O_2$ requires 455.

$^1$H-NMR (300 MHz, CDCl$_3$) δ(ppm): 8.50 (s, 1H), 8.35 (d, 1H), 7.70 (d, 1H), 7.60 (m, 2H), 7.40 (d, 1H), 7.30-7.20 (m, 2H), 7.20-7.10 (t, 2H), 6.50 (s, 1H), 3.15 (t, 4H), 2.95-2.70 (m, 8H), 2.70 (s, 3H), 2.50 (s, 3H).

Example 11

N-(3-{2-[4-(2-Methyl-5-quinolinyl)-1-piperazinyl]ethyl}phenyl)-2-(2-thienyl)acetamide (E11)

The title compound was prepared in 42% yield according to the general procedure for the preparation of the amides (Method B) starting from 3-{2-[4-(2-methyl-5-quinolinyl)-1-piperazinyl]ethyl}aniline (D6) and 2-thienylacetyl chloride.

MS: (ES/+) m/z: 471 [MH$^+$]. $C_{28}H_{30}N_4OS$ requires 470.

$^1$H-NMR (300 MHz, CDCl$_3$) δ(ppm): 8.35 (d, 1H), 7.70 (d, 1H), 7.60 (t, 1H), 7.40 (s, 1H), 7.30 (dd, 1H), 7.25-7.15 (m, 3H), 7.10-6.90 (m, 5H), 3.90 (s, 2H), 3.15 (br s, 4H), 3.00-2.70 (m, 8H), 2.70 (s, 3H).

Example 12

2-(Methyloxy)-N-(3-{2-[4-(2-methyl-5-quinolinyl)-1-piperazinyl]ethyl}phenyl)acetamide (E12)

The title compound was prepared in 62% yield according to the general procedure for the preparation of the amides (Method B) starting from 3-{2-[4-(2-methyl-5-quinolinyl)-1-piperazinyl]ethyl}aniline (D6) and (methyloxy)acetyl chloride.

MS: (ES/+) m/z: 419 [MH$^+$]. $C_{25}H_{30}N_4O_2$ requires 418.

$^1$H-NMR (300 MHz, CDCl$_3$) δ(ppm): 8.35 (d, 1H), 8.20 (s, 1H), 7.70 (d, 1H), 7.60 (t, 1H), 7.50 (s, 1H), 7.35 (d, 1H), 7.30-7.20 (m, 2H), 7.10-6.90 (dd, 2H), 4.00 (s, 2H), 3.50 (s, 3H), 3.10 (t, 4H), 2.90-2.70 (m, 8H), 2.70 (s, 3H).

Example 13

N-(3-{2-[4-(2-Methyl-5-quinolinyl)-1-piperazinyl]ethyl}phenyl)-2-(phenyloxy)acetamide (E13)

The title compound was prepared in 41% yield according to the general procedure for the preparation of the amides (Method B) starting from 3-{2-[4-(2-methyl-5-quinolinyl)-1-piperazinyl]ethyl}aniline (D6) and (phenyloxy)acetyl chloride.

MS: (ES/+) m/z: 481 [MH$^+$]. $C_{30}H_{32}N_4O_2$ requires 480.

$^1$H-NMR (400 MHz, CDCl$_3$) δ(ppm): 8.33 (d, 1H), 7.53 (m, 3H), 7.54 (br s, 1H), 7.46 (br d, 1H), 7.37 (d, 1H), 7.30 (dd, 2H), 7.23 (t, 1H), 7.09 (dd, 1H), 6.99 (m, 3H), 6.96 (t, 1H), 4.67 (s, 2H), 3.02 (br m, 4H), 2.80-2.60 (m, 8H), 2.62 (s, 3H).

Example 14

N-(3-{2-[4-(2-Methyl-5-quinolinyl)-1-piperazinyl]ethyl}phenyl)cyclopropane carboxamide (E14)

The title compound was prepared in 70% yield according to the general procedure for the preparation of the amides (Method B) starting from 3-{2-[4-(2-methyl-5-quinolinyl)-1-piperazinyl]ethyl}aniline (D6) and cyclopropanecarbonyl chloride.

MS: (ES/+) m/z: 415 [MH$^+$]. $C_{26}H_{30}N_4O$ requires 414.

$^1$H-NMR (300 MHz, CDCl$_3$) δ(ppm): 8.35 (d, 1H), 7.60-7.50 (m, 2H), 7.30 (br s, 1H), 7.30-7.20 (m, 3H), 7.05 (d, 1H), 6.95 (br d, 1H), 3.10 (t, 4H), 2.90-2.70 (m, 8H), 2.70 (s, 3H), 1.20 (t, 1H), 1.10 (m, 2H), 0.85 (m, 2H).

Example 15

N-(3-{2-[4-(2-Methyl-5-quinolinyl)-1-piperazinyl]ethyl}phenyl)-2-oxo-4-imidazolidinecarboxamide (E15)

The title compound was prepared in 51% yield according to the general procedure for the preparation of the amides (Method C) starting from 3-{2-[4-(2-methyl-5-quinolinyl)-1-piperazinyl]ethyl}aniline (D6) and 2-oxo-4-imidazolidinecarboxylic acid.

MS: (ES/+) m/z: 459 [MH$^+$]. $C_{26}H_{30}N_6O_2$ requires 458.

$^1$H-NMR (300 MHz, CDCl$_3$) δ(ppm): 8.40 (s, 1H), 8.38 (d, 1H), 7.70 (d. 1H), 7.55 (t, 1H), 7.50 (d, 1H), 7.40 (dd, 1H), 7.30-7.20 (m, 2H), 7.05 (m, 2H), 5.20 (d, 1H), 4.75 (s, 1H), 4.45 (m, 1H), 4.00 (t, 1H), 3.65 (dd, 1H), 3.10 (br s, 4H), 2.95-2.70 (m, 8H), 2.70 (br s, 3H).

Example 16

N-(3-{2-[4-(2-Methyl-5-quinolinyl)-1-piperazinyl]ethyl}phenyl)-2-pyrazine carboxamide (E16)

The title compound was prepared in 89% yield according to the general procedure for the preparation of the amides (Method C) starting from 3-{2-[4-(2-methyl-5-quinolinyl)-1-piperazinyl]ethyl}aniline (D6) and 2-pyrazinecarboxylic acid.

MS: (ES/+) m/z: 453 [MH$^+$]. $C_{27}H_{28}N_6O$ requires 452.

$^1$H-NMR (300 MHz, CDCl$_3$) δ(ppm): 9.65 (s, 1H), 9.50 (m, 1H), 8.80 (d, 1H), 8.60 (t, 1H) 8.38 (d, 1H), 7.75 (d, 1H), 7.70 (d, 1H), 7.58 (t, 1H), 7.55 (dd, 1H), 7.35 (t, 1H), 7.28 (d, 1H), 7.08 (m, 2H), 3.15 (br s, 4H, 2.95-2.70 (m, 8H), 2.70 (br s, 3H).

Example 17

5-(Methyloxy)-N-(3-{2-[4-(2-methyl-5-quinolinyl)-1-piperazinyl]ethyl}phenyl)-1,3-oxazole-2-carboxamide (E17)

The title compound was prepared in 30% yield according to the general procedure for the preparation of the amides (Method C) starting from 3-{2-[4-(2-methyl-5-quinolinyl)-1-piperazinyl]ethyl}aniline (D6) and 5-(methyloxy)-1,3-oxazole-2-carboxylic acid.

MS: (ES/+) m/z: 472 [MH$^+$]. $C_{27}H_{29}N_5O_2$ requires 471.

$^1$H-NMR (300 MHz, CDCl$_3$) δ(ppm): 8.58 (s, 1H), 8.39 (d, 1H), 7.71 (d, 1H), 7.58 (t, 1H) 7.60 (d, 1H), 7.48 (dd, 1H), 7.30 (t, 1H), 7.26 (d, 1H), 7.08 (dd, 1H), 7.04 (d, 1H), 6.28 (s, 1H), 4.03 (s, 3H), 3.15 (t, 4H) 2.95-2.70 (m, 8H), 2.74 (br s, 3H).

Example 18

N-(3-{2-[4-(2-Methyl-5-quinolinyl)-1-piperazinyl]ethyl}phenyl)-1,2,3-thiadiazole-4-carboxamide (E18)

The title compound was prepared in 75% yield according to the general procedure for the preparation of the amides (Method C) starting from 3-{2-[4-(2-methyl-5-quinolinyl)-1-piperazinyl]ethyl}aniline (D6) and 1,2,3-thiadiazole-4-carboxylic acid.

MS: (ES/+) m/z: 459 [MH$^+$]. $C_{25}H_{26}N_6OS$ requires 458.

$^1$H-NMR (300 MHz, CDCl$_3$) δ(ppm): 9.30 (s, 1H), 9.25 (s, 1H), 8.38 (d, 1H), 7.70 (d, 1H), 7.68 (d, 1H) 7.58 (t, 1H), 7.55 (dd, 1H), 7.35 (t, 1H), 7.28 (d, 1H), 7.10 (m, 2H), 3.15 (br s, 4H) 2.95-2.70 (m, 8H), 2.70 (s, 3H).

Example 19

2,4-Dimethyl-N-(3-{2-[4-(2-methyl-5-quinolinyl)-1-piperazinyl]ethyl}phenyl)-1,3-thiazole-5-carboxamide (E19)

The title compound was prepared in 68% yield according to the general procedure for the preparation of the amides (Method C) starting from 3-{2-[4-(2-methyl-5-quinolinyl)-1-piperazinyl]ethyl}aniline (D6) and 2,4-dimethyl-1,3-thiazole-5-carboxylic acid.

MS: (ES/+) m/z: 486 [MH$^+$]. $C_{28}H_{31}N_5OS$ requires 485.

$^1$H-NMR (300 MHz, CDCl$_3$) δ(ppm): 8.38 (d, 1H), 7.70 (d, 1H), 7.58 (t, 1H) 7.55 (d, 1H), 7.35-7.20 (dd, 1H), 7.30 (br s, 1H), 7.10 (m, 2H), 3.15 (t, 4H) 2.95-2.70 (m, 8H), 2.72 (s, 6H), 2.70 (s, 3H).

Example 20

1,5-Dimethyl-N-(3-{2-[4-(2-methyl-5-quinolinyl)-1-piperazinyl]ethyl}phenyl)-1H-pyrazole-3-carboxamide (E20)

The title compound was prepared in 35% yield according to the general procedure for the preparation of the amides (Method C) starting from 3-{2-[4-(2-methyl-5-quinolinyl)-1-piperazinyl]ethyl}aniline (D6) and 1,5-dimethyl-1H-pyrazole-3-carboxylic acid.

MS: (ES/+) m/z: 469 [MH$^+$]. $C_{28}H_{32}N_6O$ requires 468.

$^1$H-NMR (300 MHz, CDCl$_3$) δ(ppm): 8.60 (s, 1H), 8.38 (d, 1H), 7.70 (d, 1H), 7.68 (d, 1H), 7.58 (t, 1H) 7.45 (d, 1H), 7.35-7.20 (dd, 2H), 7.08 (d, 1H), 7.00 (d, 1H), 6.60 (s, 1H), 3.80 (s, 3H), 3.15 (t, 4H) 2.95-2.70 (m, 8H), 2.72 (s, 3H), 2.30 (s, 3H).

Example 21

N-(3-{2-[4-(2-Methyl-5-quinolinyl)-1-piperazinyl]ethyl}phenyl)-4-oxo-4,5,6,7-tetrahydro-1-benzofuran-2-carboxamide (E21)

The title compound was prepared in 20% yield according to the general procedure for the preparation of the amides (Method C) starting from 3-{2-[4-(2-methyl-5-quinolinyl)-1-piperazinyl]ethyl}aniline (D6) and 4-oxo-4,5,6,7-tetrahydro-1-benzofuran-3-carboxylic acid.

MS: (ES/+) m/z: 509 [MH+]. $C_{31}H_{32}N_4O_3$ requires 508.
¹H-NMR (300 MHz, CDCl₃) δ(ppm): 11.80 (s, 1H), 8.10 (s, 1H), 8.38 (d, 1H), 7.72 (d, 1H) 7.70 (d, 1H), 7.65 (dd, 1H), 7.58 (t, 1H), 7.30-7.20 (m, 2H), 7.08 (d, 1H), 7.00 (d, 1H), 3.15 (t, 4H), 3.00-2.65 (m, 12H), 2.70 (s, 3H), 2.25 (m, 2H).

Example 22

2-Fluoro-N-(3-{2-[4-(2-methyl-5-quinolinyl)-1-piperazinyl]ethyl}phenyl)benzamide dihydrochloride salt (E22)

The title compound was prepared in 96% yield according to the general procedure for the preparation of the amides (Method C) starting from 3-{2-[4-(2-methyl-5-quinolinyl)-1-piperazinyl]ethyl}aniline (D6) and 2-fluorobenzoic acid.
MS: (ES/+) m/z: 469 [MH+]. $C_{29}H_{29}FN_4O$ requires 468.
¹H-NMR (500 MHz, d₆-DMSO) δ(ppm): 11.00 (br s, 1H), 10.46 (s. 1H), 8.80 (br s, 1H), 8.00-7.72 (m, 4H), 7.65 (t, 1H), 7.58 (q, 1H), 7.52 (d, 1H), 7.73 (br s, 1H), 7.37-7.32 (m, 3H), 7.08 (d, 1H), 3.74 (d, 2H), 3.7-3.3 (m, 9H), 3.15 (m, 2H), 2.88 (s, 3H)

Example 23

4-Fluoro-N-(3-{2-[4-(2-methyl-5-quinolinyl)-1-piperazinyl]ethyl}phenyl)benzamide dihydrochloride salt (E23)

The title compound was prepared in 82% yield according to the general procedure for the preparation of the amides (Method C) starting from 3-{2-[4-(2-methyl-5-quinolinyl)-1-piperazinyl]ethyl}aniline (D6) and 4-fluorobenzoic acid.
HPLC/MS (ES/+): $t_R$=6.45 min; assay 98.2% a/a; m/z: 469 [MH+]. $C_{29}H_{29}FN_4O$ requires 468.
¹H-NMR (400 MHz, d₆-DMSO) δ(ppm): 11.29 (br s, 1H), 10.36 (s, 1H), 8.96 (br s, 1H), 8.08 (m, 2H), 7.99 (br s, 1H), 7.86 (br s, 1H), 7.62 (d, 1H), 7.47 (br d, 1H), 7.40 (m, 3H), 7.09 (d, 1H), 3.70-3.30 (m, 10H), 3.18 (dd, 2H), 2.93 (br s, 3H).

Example 24

2,4-Difluoro-N-(3-{2-[4-(2-methyl-5-quinolinyl)-1-piperazinyl]ethyl}phenyl)benzamide dihydrochloride salt (E24)

The title compound was prepared in 78% yield according to the general procedure for the preparation of the amides (Method C) starting from 3-{2-[4-(2-methyl-5-quinolinyl)-1-piperazinyl]ethyl}aniline (D6) and 2,4-difluorobenzoic acid.
HPLC/MS (ES/+): $t_R$=6.51 min; assay >99% a/a; m/z: 487 [MH+]. $C_{29}H_{28}F_2N_4O$ requires 486.
¹H-NMR (400 MHz, d₆-DMSO) δ(ppm): 11.16 (br s, 1H), 10.49 (s, 1H), 8.93 (br s, 1H), 7.70 (br s, 2H), 7.81 (br s, 2H), 7.75 (m, 1H), 7.53 (d, 1H), 7.47 (m, 2H), 7.39 (t, 1H), 7.25 (td, 1H), 7.10 (d, 1H), 3.70-3.30 (m, 10H), 2.92 (s, 3H).

Example 25

3-Fluoro-N-(3-{2-[4-(2-methyl-5-quinolinyl)-1-piperazinyl]ethyl}phenyl)benzamide dihydrochloride salt (E25)

The title compound was prepared in 91% yield according to the general procedure for the preparation of the amides (Method C) starting from 3-{2-[4-(2-methyl-5-quinolinyl)-1-piperazinyl]ethyl}aniline (D6) and 3-fluorobenzoic acid.
HPLC/MS (ES/+): $t_R$=6.45 min; assay >99% a/a; m/z: 469 [MH+]. $C_{29}H_{29}FN_4O$ requires 468.
¹H-NMR (400 MHz, d₆-DMSO) δ(ppm): 11.18 (br s, 1H), 10.41 (s, 1H), 8.94 (br s, 1H), 7.97 (br s, 2H), 7.87 (br s, 2H), 7.80 (m, 2H), 7.62 (m, 2H), 7.48 (m, 2H), 7.10 (d, 1H), 3.80-3.30 (m, 10H), 3.18 (m, 2H), 2.92 (br s, 3H).

Example 26

2,5-Difluoro-N-(3-{2-[4-(2-methyl-5-quinolinyl)-1-piperazinyl]ethyl}phenyl)benzamide dihydrochloride salt (E26)

The title compound was prepared in 82% yield according to the general procedure for the preparation of the amides (Method C) starting from 3-{2-[4-(2-methyl-5-quinolinyl)-1-piperazinyl]ethyl}aniline (D6) and 2,5-difluorobenzoic acid.
HPLC/MS (ES/+): $t_R$=6.45 min; assay >99% a/a; m/z: 487 [MH+]. $C_{29}H_{28}F_2N_4O$ requires 486.
¹H-NMR (400 MHz, d₆-DMSO) δ(ppm): 11.20 (br s, 1H), 10.54 (s, 1H), 8.91 (br s, 1H), 7.96 (br m, 2H), 7.80 (br m, 2H), 7.56-7.40 (m, 5H), 7.36 (t, 1H), 7.09 (d, 1H), 3.80-3.10 (m, 12H), 2.90 (s, 3H).

Example 27

3,5-Difluoro-N-(3-{2-[4-(2-methyl-5-quinolinyl)-1-piperazinyl]ethyl}phenyl)benzamide dihydrochloride salt (E27)

The title compound was prepared in 74% yield according to the general procedure for the preparation of the amides (Method C) starting from 3-{2-[4-(2-methyl-5-quinolinyl)-1-piperazinyl]ethyl}aniline (D6) and 3,5-difluorobenzoic acid.
HPLC/MS (ES/+): $t_R$=6.66 min; assay 98.6% a/a; m/z: 487 [MH+]. $C_{29}H_{28}F_2N_4O$ requires 486.
¹H-NMR (400 MHz, d₆-DMSO) δ(ppm): 11.00 (br s, 1H), 10.46 (s, 1H), 8.90 (br s, 1H), 7.93 (s, 2H), 7.90 (br s, 1H), 7.72 (m, 2H), 7.86 (s, 1H), 7.62 (d, 1H), 7.56 (m, 1H), 7.45 (br s, 1H), 7.40 (t, 1H), 7.12 (d, 1H), 3.76 (d, 2H), 3.70-3.30 (m, 8H), 3.17 (m, 2H), 2.99 (br s, 3H).

Example 28

2,3-Difluoro-N-(3-{2-[4-(2-methyl-5-quinolinyl)-1-piperazinyl]ethyl}phenyl)benzamide dihydrochloride salt (E28)

The title compound was prepared in 86% yield according to the general procedure for the preparation of the amides (Method C) starting from 3-{2-[4-(2-methyl-5-quinolinyl)-1-piperazinyl]ethyl}aniline (D6) and 2,3-difluorobenzoic acid.
HPLC/MS (ES/+): $t_R$=6.41 min, assay >99% a/a; m/z: 486 [MH+]. $C_{29}H_{28}F_2N_4O$ requires 486.
¹H-NMR (400 MHz, d₆-DMSO) δ(ppm): 11.00 (br s, 1H), 10.62 (s, 1H), 8.95 (br s, 1H), 7.94 (s, 2H), 7.82 (s, 1H), 7.80 (br s, 1H), 7.65 (m, 1H), 7.53 (d, 1H), 7.50 (m, 1H), 7.45 (br s, 1H), 7.39 (t, 1H), 7.38 (m, 1H), 7.12 (d, 1H), 3.76 (d, 2H), 3.70-3.30 (m, 8H), 3.17 (m, 2H), 2.96 (br s, 3H).

Example 29

2,6-Difluoro-N-(3-{2-[4-(2-methyl-5-quinolinyl)-1-piperazinyl]ethyl}phenyl)benzamide dihydrochloride salt (E29)

The title compound was prepared in 68% yield according to the general procedure for the preparation of the amides (Method C) starting from 3-{2-[4-(2-methyl-5-quinolinyl)-1-piperazinyl]ethyl}aniline (D6) and 2,6-difluorobenzoic acid.

HPLC/MS (ES/+): $t_R$=6.24 min; assay >99% a/a; m/z: 486 [MH$^+$]. $C_{29}H_{28}F_2N_4O$ requires 486.

$^1$H-NMR (400 MHz, d$_6$-DMSO) δ(ppm): 10.90 (br s, 1H), 10.87 (s, 1H), 8.87 (br s, 1H), 7.92 (s, 2H), 7.84 (s, 1H), 7.79 (br s, 1H), 7.62 (m, 1H), 7.48 (d, 1H), 7.50 (m, 1H), 7.44 (br s, 1H), 7.39 (t, 1H), 7.27 (m, 2H), 7.12 (d, 1H), 3.76 (d, 2H), 3.70-3.30 (m, 8H), 3.17 (m, 2H), 2.88 (br s, 3H).

Example 30

3,4-Difluoro-N-(3-{2-[4-(2-methyl-5-quinolinyl)-1-piperazinyl]ethyl}phenyl)benzamide dihydrochloride salt (E30)

The title compound was prepared in 92% yield according to the general procedure for the preparation of the amides (Method C) starting from 3-{2-[4-(2-methyl-5-quinolinyl)-1-piperazinyl]ethyl}aniline (D6) and 3,4-difluorobenzoic acid.

HPLC/MS (ES/+): $t_R$=6.66 min; assay >99% a/a; m/z: 486 [MH$^+$]. $C_{29}H_{28}F_2N_4O$ requires 486.

$^1$H-NMR (400 MHz, d$_6$-DMSO) δ(ppm): 11.04 (br s, 1H), 10.42 (s, 1H), 8.90 (br s, 1H), 8.08 (m, 1H), 7.93 (s, 2H), 7.90 (m, 1H), 7.85 (s, 1H), 7.81 (br s, 1H), 7.65 (m, 1H), 7.62 (d, 1H), 7.45 (br s, 1H), 7.39 (t, 1H), 7.11 (d, 1H), 3.76 (d, 2H), 3.70-3.30 (m, 8H), 3.17 (m, 2H), 2.89 (br s, 3H).

Example 31

3-(Methyloxy)-N-(3-{2-[4-(2-methyl-5-quinolinyl)-1-piperazinyl]ethyl}phenyl)benzamide dihydrochloride salt (E31)

The title compound was prepared in 83% yield according to the general procedure for the preparation of the amides (Method C) starting from 3-{2-[4-(2-methyl-5-quinolinyl)-1-piperazinyl]ethyl}aniline (D6) and 3-(methyloxy)benzoic acid.

HPLC/MS (ES/+): $t_R$=6.39 min; assay >99% a/a; m/z: 481[MH$^+$]. $C_{30}H_{30}N_4O_2$ requires 480.

$^1$H-NMR (400 MHz, d$_6$-DMSO) δ(ppm): 11.88 (br s, 1H), 10.30 (s, 1H), 8.86 (br s, 1H), 7.91 (br s, 2H), 7.87 (br s, 1H), 7.78 (br s, 2H), 7.63 (dd, 1H), 7.56 (d, 1H), 7.51 (m, 1H), 7.47 (t, 1H), 7.47 (br s, 1H), 7.38 (t, 1H), 7.19 (dm, 1H), 7.09 (d, 1H), 3.86 (s, 3H), 3.76 (d, 2H), 3.70-3.25 (m, 8H), 3.17 (m, 2H), 2.88 (br s, 3H).

Example 32

2-(Methyloxy)-N-(3-{2-[4-(2-methyl-5-quinolinyl)-1-piperazinyl]ethyl}phenyl)benzamide dihydrochloride salt (E32)

The title compound was prepared in 85% yield according to the general procedure for the preparation of the amides (Method C) starting from 3-{2-[4-(2-methyl-5-quinolinyl)-1-piperazinyl]ethyl}aniline (D6) and 2-(methyloxy)benzoic acid.

HPLC/MS (ES/+): $t_R$=6.54 min; assay >99% a/a; m/z: 481 [MH$^+$]. $C_{30}H_{30}N_4O_2$ requires 480.

$^1$H-NMR (400 MHz, d$_6$-DMSO) δ(ppm): 11.13 (br s, 1H), 10.17 (s, 1H), 8.93 (br s, 1H), 7.97 (s, 2H), 7.86-7.78 (br s, 1H), 7.64 (dd, 1H), 7.58-7.50 (m, 2H), 7.47 (br s, 1H), 7.36 (t, 1H), 7.21 (d, 1H), 7.09 (dt, 1H), 7.07 (d, 1H), 3.92 (s, 3H), 3.76 (d, 2H), 3.70-3.30 (m, 8H), 3.17 (m, 2H), 2.91 (br s, 3H).

Example 33

4-(Methyloxy)-N-(3-{2-[4-(2-methyl-5-quinolinyl)-1-piperazinyl]ethyl}phenyl)benzamide dihydrochloride salt (E33)

The title compound was prepared in 83% yield according to the general procedure for the preparation of the amides (Method C) starting from 3-{2-[4-(2-methyl-5-quinolinyl)-1-piperazinyl]ethyl}aniline (D6) and 4-(methyloxy)benzoic acid.

HPLC/MS (ES/+): $t_R$=6.21 min; assay >99% a/a; m/z: 481 [MH$^+$]. $C_{30}H_{30}N_4O_2$ requires 480.

$^1$H-NMR (500 MHz, d$_6$-DMSO) δ(ppm): 11.09 (br s, 1H), 10.16 (s, 1H), 8.91 (br s, 1H), 7.97 (d, 2H), 7.94 (br s, 2H), 7.84 (s, 1H), 7.81 (br s, 1H), 7.60 (d, 1H), 7.44 (br s, 1H), 7.34 (t, 1H), 7.05 (m, 3H), 3.83 (s, 3H), 3.74 (br d, 2H), 3.60-3.40 (m, 6H), 3.33 (br t, 2H), 3.14 (dd, 2H), 2.89 (br s, 3H).

Example 34

4-Cyano-N-(3-{2-[4-(2-methyl-5-quinolinyl)-1-piperazinyl]ethyl}phenyl)benzamide dihydrochloride salt (E34)

The title compound was prepared in 85% yield according to the general procedure for the preparation of the amides (Method C) starting from 3-{2-[4-(2-methyl-5-quinolinyl)-1-piperazinyl]ethyl}aniline (D6) and 4-cyanobenzoic acid.

HPLC/MS (ES/+): $t_R$=6.15 min assay >99% a/a; m/z: 481 [MH$^+$]. $C_{30}H_{30}N_4O_2$ requires 480.

$^1$H-NMR (500 MHz, d$_6$-DMSO) δ(ppm): 10.72 (br s, 1H), 10.56 (s, 1H), 8.81 (br s, 1H), 8.11 (d, 2H), 8.04 (d, 2H), 7.86 (br s, 3H), 7.75 (br s, 1H), 7.59 (d, 1H), 7.39 (br s, 1H), 7.38 (t, 1H), 7.09 (d, 1H), 3.74 (br d, 2H), 3.70-3.40 (m, 6H), 3.28 (br t, 2H), 3.14 (dd, 2H), 2.84 (br s, 3H).

Example 35

3,5-Dimethyl-N-(3-{2-[4-(2-methyl-5-quinolinyl)-1-piperazinyl]ethyl}phenyl)-4-isoxazolecarboxamide (E35)

The title compound was prepared in 56% yield according to the general procedure for the preparation of the amides (Method C) starting from 3-{2-[4-(2-methyl-5-quinolinyl)-1-piperazinyl]ethyl}aniline (D6) and 3,5-dimethyl-4-isoxazolecarboxylic acid.

MS: (ES/+) m/z: 470 [MH$^+$]. $C_{28}H_{31}N_5O_2$ requires 469.

$^1$H-NMR (400 MHz, CDCl$_3$) δ(ppm): 8.38 (d, 1H), 7.72 (d, 1H), 7.58 (t, 1H), 7.52 (br s, 1H), 7.31 (m, 2H), 7.25 (d, 1H), 7.20 (br s, 1H), 7.08 (m, 2H), 3.14 (m, 4H), 2.90 (m, 2H), 2.81 (m, 4H), 2.76 (m, 2H), 2.73 (s, 3H), 2.68 (s, 3H), 2.52 (s, 3H).

Example 36

2-Methyl-N-(3-{2-[4-(2-methyl-5-quinolinyl)-1-piperazinyl]ethyl}phenyl)-4-(trifluoromethyl)-1,3-thiazole-5-carboxamide dihydrochloride salt (E36)

The title compound was prepared in 33% yield according to the general procedure for the preparation of the amides (Method C) starting from 3-{2-[4-(2-methyl-5-quinolinyl)-1-piperazinyl]ethyl}aniline (D6) and 2-methyl-4-(trifluoromethyl)-1,3-thiazole-5-carboxylic acid.

MS: (ES/+) m/z: 540 [MH$^+$]. $C_{28}H_{28}F_3N_5OS$ requires 539.
$^1$H-NMR (400 MHz, d$_6$-DMSO) δ(ppm): 10.93 (br s, 1H), 8.82 (br s, 1H), 7.88 (br s, 2H), 7.75 (br s, 1H), 7.70 (br s, 1H), 7.43 (d, 1H), 7.40 (br s, 1H), 7.36 (t, 1H), 7.10 (d, 1H), 3.8-3.2 (m, 10H), 3.12 (m, 2H), 2.85 (s, 3H), 2.75 (s, 3H).

Example 37

2-Methyl-N-(3-{2-[4-(2-methyl-5-quinolinyl)-1-piperazinyl]ethyl}phenyl)-1,3-thiazole-4-carboxamide dihydrochloride salt (E37)

The title compound was prepared in 52% yield according to the general procedure for the preparation of the amides (Method C) starting from 3-{2-[4-(2-methyl-5-quinolinyl)-1-piperazinyl]ethyl}aniline (D6) and 2-methyl-1,3-thiazole-4-carboxylic acid.

MS: (ES/+) m/z: 472 [MH$^+$]. $C_{27}H_{29}N_5OS$ requires 471.
$^1$H-NMR (400 MHz, d$_6$-DMSO) δ(ppm): 10.70 (br s, 1H), 10.15 (s, 1H), 8.77 (br s, 1H), 8.26 (s, 1H), 7.87 (br s, 1H), 7.75-7.85 (m, 2H), 7.39 (br s, 1H), 7.34 (t, 1H), 7.06 (d, 1H), 3.80-3.20 (m, 10H), 3.12 (dd, 2H), 2.83 (br s, 3H), 2.76 (s, 3H).

Example 38

4-Methyl-N-(3-{2-[4-(2-methyl-5-quinolinyl)-1-piperazinyl]ethyl}phenyl)-1,3-thiazole-5-carboxamide dihydrochloride salt The title compound was prepared in 46% yield according to the general procedure for the preparation of the amides (Method C) starting from 3-{2-[4-(2-methyl-5-quinolinyl)-1-piperazinyl]ethyl}aniline (D6) and 4-methyl-1,3-thiazole-5-carboxylic acid.

MS: (ES/+) m/z: 472 [MH$^+$]. $C_{27}H_{29}N_5OS$ requires 471.
$^1$H-NMR (400 MHz, d$_6$-DMSO) δ(ppm): 10.83 (br s, 1H), 10.28 (s, 1H), 9.13 (s, 1H), 8.86 (br s, 1H), 7.90 (br s, 2H), 7.80-7.74 (br s-s, 2H), 7.50 (d, 1H), 7.43 (br s, 1H), 7.35 (t, 1H), 7.08 (d, 1H), 3.9-3.2 (m, 10H), 3.13 (dd, 2H), 2.87 (br s, 3H), 2.61 (s, 3H).

Example 39

1-Methyl-N-(3-{2-[4-(2-methyl-5-quinolinyl)-1-piperazinyl]ethyl}phenyl)-1H-pyrazole-5-carboxamide dihydrochloride salt (E39)

The title compound was prepared in 60% yield according to the general procedure for the preparation of the amides (Method C) starting from 3-{2-[4-(2-methyl-5-quinolinyl)-1-piperazinyl]ethyl}aniline (D6) and 1-methyl-1H-pyrazole-5-carboxylic acid.

MS: (ES/+) m/z: 455 [MH$^+$]. $C_{27}H_{30}N_6O$ requires 454.
$^1$H-NMR (400 MHz, d$_6$-DMSO) δ(ppm): 10.96 (br s, 1H), 10.27 (s, 1H), 8.85 (br s, 1H), 8.0-7.7 (m, 4H), 7.6-7.5 (m, 2H), 7.42 (br s, 1H), 7.6 (t, 1H), 7.10-7.08 (m, 2H), 4.09 (s, 3H), 3.74 (d, 2H), 3.51-3.29 (m, 8H), 3.14 (m, 2H), 2.87 (s, 3H).

Example 40

N-(3-{1-Hydroxy-2-[4-(2-methyl-5-quinolinyl)-1-piperazinyl]ethyl}phenyl)-2,4-dimethyl-1,3-thiazole-5-carboxamide dihydrochloride salt (E40)

The title compound was prepared in 68% yield according to the general procedure for the preparation of amides (Method C) starting from 1-(3-aminophenyl)-2-[4-(2-methyl-5-quinolinyl)-1-piperazinyl]ethanol (D8) and 2,4-dimethyl-1,3-thiazole-5-carboxylic acid.

MS: (ES/+) m/z: 502 [MH$^+$]. $C_{28}H_{31}N_5O_2S$ required 501.
$^1$H-NMR (400 MHz, d$_6$-DMSO) δ(ppm): 10.18 (2H, br s), 8.85 (1H, br s), 7.89 (3H, s), 7.77 (1H, br s), 7.53 (1H, d), 7.37 (2H, m), 7.18 (1H, d), 6.36 (1H, br s), 5.17 (1H, dd), 3.80-3.20 (10H, m), 2.85 (3H, s), 2.64 (3H, s), 2.53 (3H, s).

Example 41

N-(3-{1-Hydroxy-2-[4-(2-methyl-5-quinolinyl)-1-piperazinyl]ethyl}phenyl)-2-methyl-1,3-thiazole-4-carboxamide dihydrochloride salt (E41)

The title compound was prepared in 82% yield according to the general procedure for the preparation of amides (Method C) starting from 1-(3-aminophenyl)-2-[4-(2-methyl-5-quinolinyl)-1-piperazinyl]ethanol (D8) and 2-methyl-1,3-thiazole-4-carboxylic acid.

MS: (ES/+) m/z: 488 [MH$^+$]. $C_{27}H_{29}N_5O_2S$ required 487.
$^1$H-NMR (400 MHz, d$_6$-DMSO) δ(ppm): 10.38 (1H, br s), 10.23 (1H, s), 8.88 (1H, br s), 8.30 (1H, s), 8.08 (1H, br s), 7.95 (2H, br s), 7.82 (1H, br s), 7.75 (1H, dd), 7.44 (1H, br s), 7.41 (1H, t), 7.22 (1H, d), 6.40 (1H, br s), 5.22 (1H, br d), 3.81 (2H, br d), 3.70-3.30 (8H, br m), 2.90 (3H, br s), 2.79 ppm (3H, s).

Example 42

N-(3-{1-Hydroxy-2-[4-(2-methyl-5-quinolinyl)-1-piperazinyl]ethyl}phenyl)-1,5-dimethyl-1H-pyrazole-3-carboxamide dihydrochloride salt (E42)

The title compound was prepared in 95% yield according to the general procedure for the preparation of amides (Method C) starting from 1-(3-aminophenyl)-2-[4-(2-methyl-5-quinolinyl)-1-piperazinyl]ethanol (D8) and 1,5-dimethyl-1H-pyrazole-3-carboxylic acid.

MS: (ES/+) m/z: 485 [MH$^+$]. $C_{28}H_{32}N_6O_2$ required 484.
$^1$H-NMR (400 MHz, d$_6$-DMSO) δ(ppm): 10.30 (1H, br s), 9.97 (1H, s), 8.86 (1H, br s), 8.08 (1H, s), 7.92 (2H, br s), 7.79 (1H, br s), 7.69 (1H, d), 7.43 (1H, br s), 7.38 (1H, t), 7.17 (1H, d), 6.58 (1H, s), 6.38 (1H, br s), 5.19 (1H, br d), 3.86 (3H, s), 3.80 (2H, br m), 3.70-3.20 (8H, br m), 2.89 (3H, br s), 2.33 ppm (3H, s).

Example 43

N-(3-{2-[4-(2-Methyl-5-quinolinyl)-1-piperazinyl]ethyl}phenyl)methanesulfonamide (E43)

Methanesulfonyl chloride (8 μL; 1.2 eq) was added dropwise to a solution of 3-{2-[4-(2-methyl-5-quinolinyl)-1-piperazinyl]ethyl}aniline (D6) (0.03 g; 1 eq) in pyridine (0.5 mL). The reaction was stirred at r.t. overnight. The reaction mixture was concentrated under reduced pressure, diluted with water (1 mL) and a saturated aqueous solution of sodium hydrogen carbonate (1 mL), extracted into dichloromethane (3×2 mL), dried over $Na_2SO_4$ and concentrated under reduced pressure. The crude was purified by flash chromatography, eluting with a gradient from dichloromethane to dichloromethane/MeOH (98/2) affording the title compound in 44% yield (0.016 g).

MS; (ES) m/z: 425.4 [MH]$^+$. $C_{23}H_{28}N_4O_2S$ requires 424.
$^1$H-NMR (300 MHz, MeOD) δ(ppm): 8.40 (d, 1H), 7.55 (m, 2H), 7.30 (d, 1H), 7.15 (t, 1H), 7.10 (m, 2H), 6.90 ((bt, 2H), 3.05 (bt, 4H), 2.85 (s, 3H), 2.83-2.63 (bm, 8H), 2.60 (s, 3H).

Example 44

N-(3-{2-[4-(2-Methyl-5-quinolinyl)-1-piperazinyl]ethyl}phenyl)-1-propanesulfonamide (E44)

The title compound was prepared in 62% yield using a similar procedure to example E43 starting from 3-{2-[4-(2-methyl-5-quinolinyl)-1-piperazinyl]ethyl}aniline (D6) and propanesulfonyl chloride.

MS; (ES) m/z: 453.4 [MH]$^+$. $C_{25}H_{32}N_4O_2S$ requires 452.
$^1$H-NMR (300 MHz, CDCl$_3$) δ(ppm): 8.35 (d, 1H), 7.70 (d, 1H), 7.60 (t, 1H), 7.30 (m, 2H), 7.1 (m, 2H), 7.01 (d, 1H), 3.30 (bm, 6H), 2.80 (bm, 6H), 2.60 (s, 3H), 1.80 (m, 2H), 1.0 (t, 3H).

General Procedure for the Preparation of Carbamates and their Corresponding Dihydrochloride Salts Starting from 3-{2-[4-(2-methyl-5-quinolinyl)-1-piperazinyl]ethyl}aniline (D6): Method D Diisopropylethylamine (1.5 eq) and a chloroformate (1.2 eq) were added sequentially to a stirred solution of 3-{2-[4-(2-methyl-5-quinolinyl)-1-piperazinyl]ethyl}aniline (D6) (1 eq) in dichloromethane at 0° C. The solution was stirred for 1 hr at room temperature, then diluted with dichloromethane and washed with a saturated aqueous solution of NH$_4$Cl and brine and then dried over Na$_2$SO$_4$. The solution was concentrated under reduced pressure. The crude material was purified on SPE cartridge (Silica) eluting with a gradient from dichloromethane/MeOH 99/1 to dichloromethane/MeOH 98/2 affording the final compound (yields ranged from 43 to 78%).

The free base could be converted into its dihydrochloride salt by dissolving the compound in dichloromethane and adding a 1M ethereal solution of HCl (2.1 eq) dropwise. A yellow solid precipitated and the suspension was stirred for 15 min. The solvent was removed under reduced pressure affording a crude material which was triturated with Et$_2$O. The final compound was then recovered by filtration (yield quantitative).

Example 45

Methyl (3-{2-[4-(2-methyl-5-quinolinyl)-1-piperazinyl]ethyl}phenyl)carbamate (E45)

The title compound was prepared in 41% yield according to the general procedure for the preparation of carbamates (Method D) starting from 3-{2-[4-(2-methyl-5-quinolinyl)-1-piperazinyl]ethyl}aniline (D6) and methyl chloroformate.

MS; (ES) m/z: 405.4 [MH]$^+$. $C_{24}H_{28}N_4O_2$ requires 404.
$^1$H-NMR (300 MHz, CDCl$_3$) δ(ppm): 8.33 (d, 1H), 7.70 (d, 1H), 7.6 (t, 1H), 7.30 (bs, 1H), 7.25 (t, 1H), 7.22 (dd, 1H), 7.20 (d, 1H), 7.10 (d, 1H), 6.95 (dd, 1H), 6.55 (bs, 1H), 3.8 (s, 3H), 3.28 (bm, 4H), 3.28 (t, 2H), 2.85 (t, 2H), 2.75 (bm, 4H), 2.66 (s, 3H).

Example 46

Ethyl (3-{2-[4-(2-methyl-5-quinolinyl)-1-piperazinyl]ethyl}phenyl)carbamate dihydrochloride (E46)

The title compound was prepared in 79% yield according to the general procedure for the preparation of carbamates (Method D) starting from 3-{2-[4-(2-methyl-5-quinolinyl)-1-piperazinyl]ethyl}aniline (D6) and ethyl chloroformate.

MS: (ES) m/z: 419 [MH$^+$]. $C_{25}H_{30}N_4O_2$ requires 418.
$^1$H-NMR (400 MHz, d$_6$-DMSO) δ(ppm): 11.00 (bs, 1H), 9.74 (s, 1H), 8.95 (s, 1H), 8.00 (s, 2H), 7.87 (s, 1H), 7.57 (s, 1H), 7.51 (bs, 1H), 7.36 (m, 2H), 7.02 (d, 1H), 4.21 (q, 2H), 3.80 (d, 2H), 3.7-3.3 (m, 8H), 3.17 (m, 2H), 2.96 (bs, 3H), 1.33 (t, 3H).

Example 47

Propyl (3-{2-[4-(2-methyl-5-quinolinyl)-1-piperazinyl]ethyl}phenyl)carbamate dihydrochloride (E47)

The title compound was prepared in 78% yield according to the general procedure for the preparation of carbamates (Method D) starting from 3-{2-[4-(2-methyl-5-quinolinyl)-1-piperazinyl]ethyl}aniline (D6) and propyl chloroformate.

MS: (ES) m/z: 433 [MH$^+$]. $C_{26}H_{32}N_4O_2$ requires 432.
$^1$H-NMR (400 MHz, d$_6$-DMSO) δ(ppm): 10.88 (bs, 1H), 9.65 (s, 1H), 8.84 (bs, 1H), 7.89 (bs, 2H), 7.76 (bs, 1H), 7.47 (s, 1H), 7.40 (bs, 1H), 7.27-6.92 (m-d, 3H), 4.02 (t, 2H), 3.8-3.2 (bm, 10H), 3.07 (dd, 2H), 2.85 (bs, 3H), 1.62 (m, 2H), 0.91 (t, 3H).

Example 48

1-Methylethyl (3-{2-[4-(2-methyl-5-quinolinyl)-1-piperazinyl]ethyl}phenyl)carbamate dihydrochloride (E48)

The title compound was prepared in 77% yield according to the general procedure for the preparation of carbamates (Method D) starting from 3-{2-[4-(2-methyl-5-quinolinyl)-1-piperazinyl]ethyl}aniline (D6) and 1-methylethyl chloridocarbonate.

MS: (ES) m/z: 433 [MH$^+$]. $C_{26}H_{32}N_4O_2$ requires 432.
$^1$H-NMR (400 MHz, d$_6$-DMSO) δ(ppm): 10.98 (bs, 1H), 9.58 (s, 1H), 8.86 (bs, 1H), 7.91 (bs, 2H), 7.77 (bs, 1H), 7.48 (s, 1H), 7.42 (bs, 1H), 7.25 (m, 2H), 6.91 (d, 1H), 4.87 (m, 1H), 3.75-3.2 (bm, 10H), 3.07 (dd, 2H), 2.87 (bs, 3H), 1.24 (d, 6H).

Example 49

2-Methylpropyl (3-{2-[4-(2-methyl-5-quinolinyl)-1-piperazinyl]ethyl}phenyl) carbamate dihydrochloride (E49)

The title compound was prepared in 70% yield according to the general procedure for the preparation of carbamates (Method D) starting from 3-{2-[4-(2-methyl-5-quinolinyl)-1-piperazinyl]ethyl}aniline (D6) and 2-methylpropyl chloridocarbonate.

MS: (ES) m/z: 447 [MH$^+$]. $C_{27}H_{34}N_4O_2$ requires 446.

¹H-NMR (400 MHz, d₆-DMSO) δ(ppm): 10.94 (bs, 1H), 9.64 (s, 1H), 8.86 (s, 1H), 7.91 (s, 2H), 7.77 (s, 1H), 7.48 (s, 1H), 7.41 (bs, 1H), 7.28 (m, 2H), 6.93 (d, 1H), 3.85 (q, 2H), 3.70 (d, 2H), 3.7-3.25 (m, 8H), 3.07 (m, 2H), 2.86 (bs, 3H), 1.09 (m, 1H), 0.92 (d, 6H).

Example 50

Phenyl (3-{2-[4-(2-methyl-5-quinolinyl)-1-piperazinyl]ethyl}phenyl)carbamate dihydrochloride (E50)

The title compound was prepared in 59% yield according to the general procedure for the preparation of carbamates (Method D) starting from 3-{2-[4-(2-methyl-5-quinolinyl)-1-piperazinyl]ethyl}aniline (D6) and phenyl chloridocarbonate.

MS: (ES) m/z: 467 [MH⁺]. $C_{29}H_{30}N_4O_2$ requires 466.

¹H-NMR (400 MHz, d₆-DMSO) δ(ppm): 10.95 (bs, 1H), 10.27 (s, 1H), 8.84 (s, 1H), 7.90 (s, 2H), 7.75 (s, 1H), 7.52 (s, 1H), 7.4-7.2 (m, 8H), 7.00 (d, 1H), 3.71 (d, 2H), 3.7-3.3 (m, 8H), 3.09 (m, 2H), 2.86 (bs, 3H)

Example 51

Phenyl methyl (3-{2-[4-(2-methyl-5-quinolinyl)-1-piperazinyl]ethyl}phenyl)carbamate dihydrochloride (E51)

The title compound was prepared in 43% yield according to the general procedure for the preparation of carbamates (Method D) starting from 3-{2-[4-(2-methyl-5-quinolinyl)-1-piperazinyl]ethyl}aniline (D6) and phenylmethyl chloridocarbonate.

MS: (ES) m/z: 481 [MH⁺]. $C_{30}H_{32}N_4O_2$ requires 480.

¹H-NMR (400 MHz, d₆-DMSO) δ(ppm): 10.8 (bs, 1H), 9.8 (s, 1H), 8.9 (bs, 1H), 7.9 (bs, 2H), 7.76 (bs, 1H), 7.50 (bs, 1H), 7.4-7.2 (m, 8H), 6.95 (d, 1H), 5.15 (s, 2H), 3.72 (bd, 2H), 3.6-3.2 (m, 8H), 3.09 (m, 2H), 2.86 (bs, 3H).

General Procedure for the Preparation of Ureas or Thioureas and their Corresponding Dihydrochloride Salts Starting from 3-{2-[4-(2-methyl-5-quinolinyl)-1-piperazinyl]ethyl}aniline (D6): Method E An isocyanate or isothiocyanate (1 eq) was added to a stirred solution of 3-{2-[4-(2-methyl-5-quinolinyl)-1-piperazinyl]ethyl}aniline (D6) (1 eq) in dichloromethane at room temperature under an inert atmosphere, and the reaction was left under stirring for 16 h. The solution was then poured into water and extracted with dichloromethane, the organic phase was dried over Na₂SO₄ and the solvent was removed under reduced pressure. The crude material was purified on SPE cartridge (Silica) using a gradient from dichloromethane to dichloromethane/MeOH 95/5 as eluant affording the final compound (yields ranged from 30 to 80%).

The free base could be converted into its dihydrochloride salt by dissolving the compound in Et₂O and MeOH and adding an 1M ethereal solution of HCl (2.1 eq) dropwise. A yellow solid precipitated and the suspension was stirred for 15 min. The solvent was removed under reduced pressure affording a crude material which was triturated with Et₂O. The final compound was then recovered by filtration (yield quantitative).

General Procedure for the Preparation of Ureas and their Corresponding Dihydrochloride Salts Starting from 3-{2-[4-(2-methyl-5-quinolinyl)-1-piperazinyl]ethyl}aniline(D6): Method F Triethylamine(6 eq) and solid triphosgene (0.5 eq) were in added sequentially to a stirred solution of 3-{2-[4-(2-methyl-5-quinolinyl)-1-piperazinyl]ethyl}aniline (D6) (1 eq) in dichloromethane at 0° C. under an inert atmosphere. The reaction mixture was left under stirring for 1 h then diisopropylethylamine and an amine (1.1 eq) dissolved in CH₃CN were added dropwise. The solution was stirred for 16 h then diluted with dichloromethane, washed with saturated aqueous solutions of NaHCO₃ and brine and dried over Na₂SO₄. The solution was concentrated under reduced pressure and the crude material was purified on SPE cartridge (Silica) eluting with a gradient from dichloromethane to dichloromethane/MeOH 98/2 affording the final compound (yields ranged from 20 to 50%). The free base could be converted into its dihydrochloride salt by dissolving the compound in Et₂O and MeOH and adding an 1M ethereal solution of HCl (2.1 eq) dropwise. A yellow solid precipitated and the suspension was stirred for 15 min. The solvent was removed under reduced pressure affording a crude material which was triturated with Et₂O. The final compound was then recovered by filtration (yield quantitative).

Example 52

N-(3,5-Difluorophenyl)-N'-(3-{2-[4-(2-methylquinolin-5-yl)piperazin-1-yl]ethyl}phenyl)urea dihydrochloride (E52)

The title compound was prepared in 40% yield according to the general procedure for the preparation of ureas (Method E) starting from 3-{2-[4-(2-methyl-5-quinolinyl)-1-piperazinyl]ethyl}aniline (D6) and 1,3-difluoro-5-isocyanatobenzene.

MS:(ES/+) m/z: 502 [MH⁺] $C_{29}H_{29}F_2N_5O$ requires 501.

¹H-NMR (400 MHz, d₆-DMSO) δ(ppm): 10.8 (bs, 1H), 9.71 (s, 1H), 9.29 (s, 1H), 8.9 (bs, 1H), 7.94 (bs, 2H), 7.82 (bs, 1H), 7.53 (s, 1H), 7.45 (bs, 1H), 7.31 (d, 2H), 7.20 (dd, 2H), 6.97 (t, 1H), 6.80 (tt, 1H), 3.70 (bd, 2H), 3.7-3.2 (m, 8H), 3.13 (dd, 2H), 2.90 (bs, 3H).

Example 53

N-(2-Chlorophenyl)-N'-(3-{2-[4-(2-methyl-5-quinolinyl)-1-piperazinyl]ethyl}phenyl)urea dihydrochloride (E53)

The title compound was prepared in 55% yield according to the general procedure for the preparation of ureas (Method E) starting from 3-{2-[4-(2-methyl-5-quinolinyl)-1-piperazinyl]ethyl}aniline (D6) and 1-chloro-2-isocyanatobenzene.

MS: (ES/+) m/z: 500 [MH⁺] $C_{29}H_{30}ClN_5O$ requires 499.

¹H-NMR (400 MHz, d₆-DMSO) δ(ppm): 10.89 (bs, 1H), 9.66 (s, 1H), 8.86 (bs, 1H), 8.41 (s, 1H), 8.14 (dd, 1H), 7.90 (bs, 2H), 7.78 (bs, 1H), 7.54 (d, 1H), 7.40 (bs, 1H), 7.43 (dd, 1H), 7.27 (m, 3H), 7.02 (dt, 1H), 6.93 (m, 1H), 3.71 (d, 2H), 3.6-3.2 (m, 8H), 3.10 (m, 2H), 2.86 (bs, 3H).

Example 54

N-(3-Chlorophenyl)-N'-(3-{2-[4-(2-methyl-5-quinolinyl)-1-piperazinyl]ethyl}phenyl)urea dihydrochloride (E54)

The title compound was prepared in 52% yield according to the general procedure for the preparation of ureas (Method E) starting from 3-{2-[4-(2-methyl-5-quinolinyl)-1-piperazinyl]ethyl}aniline (D6) and 1-chloro-3-isocyanatobenzene.

MS: (ES/+) m/z: 500 [MH$^+$] C$_{29}$H$_{30}$ClN$_5$O requires 499.

$^1$H-NMR (400 MHz, d$_6$-DMSO) δ(ppm): 10.53 (bs, 1H), 9.34 (s, 1H), 9.15 (s, 1H), 8.81 (bs, 1H), 7.88 (bs, 2H), 7.76 (t, 1H), 7.74 (bs, 1H), 7.57 (s, 1H), 7.41 (bs, 1H), 7.30 (m, 4H), 7.03 (dt, 1H), 6.96 (bd, 1H), 3.76 (bd, 2H), 3.6-3.2 (m, 8H), 3.11 (dd, 2H), 2.85 (bs, 3H).

Example 55

N-(3-Fluorophenyl)-N'-(3-{2-[4-(2-methyl-5-quinolinyl)-1-piperazinyl]ethyl}phenyl)urea dihydrochloride (E55)

The title compound was prepared in 48% yield according to the general procedure for the preparation of ureas (Method E) starting from 3-{2-[4-(2-methyl-5-quinolinyl)-1-piperazinyl]ethyl}aniline (D6) and 1-fluoro-3-isocyanatobenzene.

MS: (ES/+) m/z: 484[MH$^+$] C$_{29}$H$_{30}$FN$_5$O requires 483.

$^1$H-NMR (400 MHz, d$_6$-DMSO) δ(ppm): 10.7 (bs, 1H), 9.47 (s, 1H), 9.24 (s, 1H), 8.75 (bs, 1H), 7.81 (bs, 2H), 7.68 (bs, 1H), 7.50 (d+bs, 2H), 7.44 (bs, 1H), 7.31 (t, 1H), 7.3-7.24 (m, 2H), 7.09 (d, 1H), 6.89 (d, 1H), 6.74 (td, 1H), 3.7-3.2 (m, 10H), 3.07 (m, 2H), 2.8 (bs, 3H).

Example 56

N-(4-Fluorophenyl)-N'-(3-{2-[4-(2-methyl-5-quinolinyl)-1-piperazinyl]ethyl}phenyl)urea dihydrochloride (E56)

The title compound was prepared in 64% yield according to the general procedure for the preparation of ureas (Method E) starting from 3-{2-[4-(2-methyl-5-quinolinyl)-1-piperazinyl]ethyl}aniline (D6) and 1-fluoro-4-isocyanatobenzene.

MS: (ES/+) m/z: 484[MH$^+$]. C$_{29}$H$_{30}$FN$_5$O requires 483.

$^1$H-NMR (400 MHz, d$_6$-DMSO) δ(ppm): 10.49 (bs, 1H), 9.40 (s, 1H), 8.96 (s, 1H), 8.77 (bs, 1H), 7.83 (bs, 2H), 7.71 (bs, 1H), 7.51 (bs, 1H), 7.45 (dd, 2H), 7.37 (bs, 1H), 7.25 (bd, 2H), 7.10 (t, 2H), 6.90 (bt, 1H), 3.8-3.2 (m, 10H), 3.06 (dd, 2H), 2.81 (bs, 3H).

Example 57

N-(2-Fluorophenyl)-N'-(3-{2-[4-(2-methyl-5-quinolinyl)-1-piperazinyl]ethyl}phenyl)urea dihydrochloride (E57)

The title compound was prepared in 75% yield according to the general procedure for the preparation of ureas (Method E) starting from 3-{2-[4-(2-methyl-5-quinolinyl)-1-piperazinyl]ethyl}aniline (D6) and 1-fluoro-2-isocyanatobenzene.

MS: (ES/+) m/z: 484[MH$^+$] C$_{29}$H$_{30}$FN$_5$O requires 483.

$^1$H-NMR (400 MHz, d$_6$-DMSO) δ(ppm): 10.9 (bs, 1H), 9.36 (s, 1H), 8.8 (bs, 1H), 8.67 (s, 1H), 8.11 (t, 1H), 7.86 (bs, 2H), 7.71 (bs, 1H), 7.49 (d, 1H), 7.37 (bs, 1H), 7.26 (m, 2H), 7.20 (dd, 1H), 7.07 (dd, 1H), 6.98 (m, 1H), 6.90 (m, 1H), 3.69 (d, 2H), 3.5-3.2 (m, 8H), 3.09 (m, 2H), 2.82 (bs, 3H).

Example 58

N-[4-(Methyloxy)phenyl]-N'-(3-{2-[4-(2-methyl-5-quinolinyl)-1-piperazinyl]ethyl}phenyl)urea dihydrochloride (E58)

The title compound was prepared in 54% yield according to the general procedure for the preparation of ureas (Method E) starting from 3-{2-[4-(2-methyl-5-quinolinyl)-1-piperazinyl]ethyl}aniline (D6) and 1-isocyanato-4-(methyloxy)benzene.

MS: (ES/+) m/z: 496[MH$^+$] C$_{30}$H$_{33}$N$_5$O$_2$ requires 495.

$^1$H-NMR (400 MHz, d$_6$-DMSO) δ(ppm): 10.66 (bs, 1H), 8.92 (s, 1H), 8.82 (bs, 1H), 8.80 (s, 1H), 7.88 (bs, 2H), 7.76 (bs, 1H), 7.50 (bs, 1H), 7.39 (bs, 1H), 7.24 (m, 2H), 6.88 (m, 1H), 7.34 (d, 2H), 6.84 (d, 2H), 3.72 (m, 2H), 3.69 (s, 3H), 3.6-3.0 (m, 10H), 2.81 (bs, 3H).

Example 59

N-[3-(Methyloxy)phenyl]-N'-(3-{2-[4-(2-methyl-5-quinolinyl)-1-piperazinyl]ethyl}phenyl)urea dihydrochloride (E59)

The title compound was prepared in 58% yield according to the general procedure for the preparation of ureas (Method E) starting from 3-{2-[4-(2-methyl-5-quinolinyl)-1-piperazinyl]ethyl}aniline (D6) and 1-isocyanato-3-(methyloxy)benzene.

MS: (ES/+) m/z: 496[MH$^+$] C$_{30}$H$_{33}$N$_5$O$_2$ requires 495.

$^1$H-NMR (400 MHz, d$_6$-DMSO) δ(ppm): 10.54 (bs, 1H), 9.00 (s, 1H), 8.99 (s, 1H), 8.80 (bs, 1H), 7.91 (t, 1H), 7.85 (bs, 2H), 7.73 (bs, 1H), 7.52 (bs, 1H), 7.39 (bs, 1H), 7.25 (m, 2H), 7.15 (t, 1H), 6.90 (m, 1H), 3.72 (m, 2H), 3.69 (s, 3H), 3.6-3.0 (m, 10H), 2.81 (bs, 3H).

Example 60

N-[2-(Methyloxy)phenyl]-N'-(3-{2-[4-(2-methyl-5-quinolinyl)-1-piperazinyl]ethyl}phenyl)urea dihydrochloride (E60)

The title compound was prepared in 42% yield according to the general procedure for the preparation of ureas (Method E) starting from 3-{2-[4-(2-methyl-5-quinolinyl)-1-piperazinyl]ethyl}aniline (D6) and 1-isocyanato-2-(methyloxy)benzene.

MS (ES/+) m/z: 496[MH$^+$] C$_{30}$H$_{33}$N$_5$O$_2$ requires 495.

$^1$H-NMR (400 MHz, d$_6$-DMSO) δ(ppm): 10.77 (bs, 1H), 9.43 (s, 1H), 8.83 (bs, 1H), 8.26 (s, 1H), 8.10 (dd, 1H), 7.88 (bs, 2H), 7.75 (bs, 1H), 7.56 (s, 1H), 7.40 (bs, 1H), 7.24 (m, 2H), 7.0-6.8 (m, 4H), 3.86 (s, 3H), 3.72 (d, 2H), 3.6-3.2 (m, 8H), 3.08 (m, 2H), 2.84 (bs, 3H).

Example 61

N-(3-{2-[4-(2-Methyl-5-quinolinyl)-1-piperazinyl]ethyl}phenyl)-N'-[2-(trifluoromethyl)phenyl]urea dihydrochloride (E61)

The title compound was prepared in 63% yield according to the general procedure for the preparation of ureas (Method E) starting from 3-{2-[4-(2-methyl-5-quinolinyl)-1-piperazinyl]ethyl}aniline (D6) and 1-isocyanato-2-(trifluoromethyl)benzene.

MS (ES/+) m/z: 534[MH$^+$] $C_{30}H_{30}F_3N_5O$ requires 533.

$^1$H-NMR (400 MHz, d$_6$-DMSO) δ(ppm): 10.83 (bs, 1H), 9.54 (s, 1H), 8.83 (bs, 1H), 8.15 (s, 1H), 8.14 (dd, 1H), 7.88 (bs, 2H), 7.73 (bs, 1H), 7.64 (d, 1H), 7.59 (t, 1H), 7.50 (s, 1H), 7.38 (bs, 1H), 7.25 (m, 3H), 6.91 (m, 1H), 3.69 (m, 2H), 3.6-3.2 (m, 8H), 3.07 (m, 2H), 2.83 (bs, 3H).

Example 62

N-(3-{2-[4-(6-Methyl-1-naphthalenyl)-1-piperazinyl]ethyl}phenyl)-N'-[3-(trifluoromethyl)phenyl]urea dihydrochloride (E62)

The title compound was prepared in 23% yield according to the general procedure for the preparation of ureas (Method E) starting from 3-{2-[4-(2-methyl-5-quinolinyl)-1-piperazinyl]ethyl}aniline (D6) and 1-isocyanato-3-(trifluoromethyl)benzene.

MS: (ES/+) m/z: 534[MH$^+$] $C_{31}H_{31}F_3N_4O$ requires 533.

$^1$H-NMR (400 MHz, d$_6$-DMSO) δ(ppm): 10.41 (bs, 1H), 9.47 (s, 1H), 9.16 (s, 1H), 8.81 (bs, 1H), 8.08 (s, 1H), 7.86 (bs, 2H), 7.72 (bs, 1H), 7.61 (s, 1H), 7.6-7.5 (m, 2H), 7.41 (bs, 1H), 7.35-7.25 (m, 3H), 6.97 (d, 1H), 3.76 (bm, 2H), 3.7-3.3 (bm, 6H), 3.27 (bm, 2H), 3.11 (m, 2H), 2.85 (bs, 3H).

Example 63

N-(3-{2-[4-(2-Methyl-5-quinolinyl)-1-piperazinyl]ethyl}phenyl)-N'-[4-(trifluoromethyl)phenyl]urea dihydrochloride (E63)

The title compound was prepared in 45% yield according to the general procedure for the preparation of ureas (Method E) starting from 3-{2-[4-(2-methyl-5-quinolinyl)-1-piperazinyl]ethyl}aniline (D6) and 1-isocyanato-4-(trifluoromethyl)benzene.

MS: (ES/+) m/z: 534[MH$^+$] $C_{30}H_{30}F_3N_5O$ requires 533.

$^1$H-NMR (400 MHz, d$_6$-DMSO) δ(ppm): 10.34 (bs, 1H), 9.45 (s, 1H), 9.12 (s, 1H), 8.71 (bs, 1H), 7.81 (t, 1H), 7.63 (m, 5H), 7.54 (s, 1H), 7.53 (bs, 1H), 7.27 (bs, 2H), 6.93 (bd, 1H), 3.8-3.1 (bm, 10H), 3.07 (dd, 2H), 2.79 (bs, 3H).

Example 64

N-(3-{2-[4-(2-Methyl-5-quinolinyl)-1-piperazinyl]ethyl}phenyl)-N'-propyl urea dihydrochloride (E64)

The title compound was prepared in 53% yield according to the general procedure for the preparation of ureas (Method E) starting from 3-{2-[4-(2-methyl-5-quinolinyl)-1-piperazinyl]ethyl}aniline (D6) and 1-isocyanatopropane.

MS: (ES/+) m/z: 432[MH$^+$] $C_{26}H_{33}N_5O$ requires 431.

$^1$H-NMR (400 MHz, d$_6$-DMSO) δ(ppm): 10.5 (bs, 1H), 8.75 (bs, 1H), 8.54 (s, 1H), 7.83 (bs, 2H), 7.7 (bs, 1H), 7.45 (s, 1H), 7.38 (bs, 1H), 7.18 (m, 2H), 6.81 (d, 1H), 6.23 (bt, 1H), 3.7-3.25 (bd, bt, 4H), 3.6-3.3 (m, 4H), 3.4-3.02 (m, m, 6H), 2.81 (bs, 3H), 1.41 (m, 2H), 0.85 (t, 3H).

Example 65

N-(1,1-Dimethylethyl)-N'-(3-{2-[4-(2-methyl-5-quinolinyl)-1-piperazinyl]ethyl}phenyl)urea dihydrochloride (E65)

The title compound was prepared in 79% yield according to the general procedure for the preparation of ureas (Method E) starting from 3-{2-[4-(2-methyl-5-quinolinyl)-1-piperazinyl]ethyl}aniline (D6) and 2-isocyanato-2-methylpropane.

MS: (ES/+) m/z: 446[MH$^+$] $C_{27}H_{35}N_5O$ requires 445.

$^1$H-NMR (400 MHz, d$_6$-DMSO) δ(ppm): 10.48 (bs, 1H), 8.75 (bs, 1H), 8.37 (s, 1H), 7.83 (bs, 2H), 7.7 (bs, 1H), 7.51 (s, 1H), 7.38 (bs, 1H), 7.17 (t, 1H), 7.04 (dd, 1H), 6.79 (d, 1H), 6.08 (s, 1H), 3.71-3.24 (bd, bt, 4H), 3.6-3.3 (m, 4H), 3.40 (m, 2H), 3.02 (m, 2H), 2.81 (bs, 3H), 1.27 (s, 9H).

Example 66

N-(3-{2-[4-(2-Methyl-5-quinolinyl)-1-piperazinyl]ethyl}phenyl)-N'-(phenyl methyl)urea dihydrochloride (E66)

The title compound was prepared in 68% yield according to the general procedure for the preparation of ureas (Method E) starting from 3-{2-[4-(2-methyl-5-quinolinyl)-1-piperazinyl]ethyl}aniline (D6) and (isocyanatomethyl)benzene.

MS: (ES/+) m/z: 480 [MH$^+$] $C_{30}H_{33}N_5O$ requires 479.

$^1$H-NMR (400 MHz, d$_6$-DMSO) δ(ppm): 10.74 (bs, 1H), 8.84 (bs, 1H), 8.76 (s, 1H), 7.88 (bs, 2H), 7.75 (bs, 1H), 7.48 (s, 1H), 7.40 (bs, 1H), 7.32 (m, 4H), 7.20 (m, 3H), 6.80 (m, 1H), 6.77 (t, 1H), 4.28 (d, 2H), 3.70 (d, 2H), 3.71 (d, 2H), 3.6-3.2 (m, 8H), 3.04 (m, 2H), 2.85 (bs, 3H).

Example 67

N-Methyl-N'-(3-{2-[4-(2-methyl-5-quinolinyl)-1-piperazinyl]ethyl}phenyl)-N-phenylurea dihydrochloride (E67)

The title compound was prepared in 47% yield according to the general procedure for the preparation of ureas (Method F) starting from 3-{2-[4-(2-methyl-5-quinolinyl)-1-piperazinyl]ethyl}aniline (D6) and N-methylaniline.

MS: (ES/+) m/z: 480 [MH$^+$]. $C_{30}H_{33}N_5O$ requires 479.

$^1$H-NMR (400 MHz, d$_6$-DMSO) δ(ppm): 10.9 (bs, 1H), 8.85 (bs, 1H), 8.14 (s, 1H), 7.9 (bs, 2H), 7.75 (bs, 1H), 7.44-7.36 (m, 4H), 7.32-7.25 (m, 3H), 7.24 (d, 1H), 7.20 (t, 1H), 6.88 (d, 1H), 3.69 (bd, 2H), 3.6-3.2 (m, 8H), 3.26 (s, 3H), 3.05 (m, 2H), 2.85 (bs, 3H).

Example 68

N-(3-{2-[4-(2-Methyl-5-quinolinyl)-1-piperazinyl]ethyl}phenyl)-N'-phenylurea dihydrochloride (E68)

The title compound was prepared in 73% yield according to the general procedure for the preparation of ureas (Method E) starting from 3-{2-[4-(2-methyl-5-quinolinyl)-1-piperazinyl]ethyl}aniline (D6) and isocyanatobenzene.

MS: (ES/+) m/z: 466 [MH$^+$] $C_{29}H_{31}N_5O$ requires 465.

$^1$H-NMR (500 MHz, d$_6$-DMSO) δ(ppm): 10.4 (bs, 1H), 8.95 (bd, 2H), 8.75 (bs, 1H), 7.83 (bs, 2H), 7.7 (bs, 1H), 7.54 (s, 1H), 7.45 (dd, 2H), 7.38 (bs, 1H), 7.27 (m, 4H), 6.96 (m, 1H), 6.91 (m, 1H), 3.73 (bd, 2H), 3.6-3.3 (m, 6H), 3.24 (t, 2H), 3.08 (dd, 2H), 2.81 (bs, 3H).

Example 69

N-cyclohexyl-N'-(3-{2-[4-(2-methyl-5-quinolinyl)-1-piperazinyl]ethyl}phenyl)urea dihydrochloride (E69)

The title compound was prepared in 64% yield according to the general procedure for the preparation of ureas (Method E) starting from 3-{2-[4-(2-methyl-5-quinolinyl)-1-piperazinyl]ethyl}aniline (D6) and isocyanatocyclohexane.

MS: (ES/+) m/z: 472 [MH$^+$] $C_{29}H_{37}N_5O$ requires 471.

$^1$H-NMR (400 MHz, d$_6$-DMSO) δ(ppm): 8.84 (bs, 1H), 8.5 (bd, 1H), 7.9 (bs, 2H), 7.78 (bs, 1H), 7.4 (bs, 2H), 7.26 (m, 2H), 6.8 (d, 1H), 6.2 (bd, 1H), 3.7-3.2 (m, 11H), 3.03 (dd, 2H), 2.85 (bs, 3H), 1.8 (m, 2H), 1.65 (m, 2H), 1.5 (m, 1H), 1.25 (m, 3H), 1.15 (m, 2H).

Example 70

N-Ethyl-N'-(3-{2-[4-(2-methyl-5-quinolinyl)-1-piperazinyl]ethyl}phenyl)thiourea dihydrochloride (E70)

The title compound was prepared in 74% yield according to the general procedure for the preparation of ureas (Method E) starting from 3-{2-[4-(2-methyl-5-quinolinyl)-1-piperazinyl]ethyl}aniline (D6) and isothiocyanatoethane.

MS:(ES/+) m/z: 434 [MH$^+$] $C_{25}H_{31}N_5S$ requires 433.

$^1$H-NMR (400 MHz, d$_6$-DMSO) δ(ppm): 11.11 (bs, 1H), 9.73 (bs, 1H), 8.93 (bs, 1H), 7.99 (m, 3H), 7.82 (bd, 1H), 7.44 (s, 2H), 7.30 (m, 2H), 7.03 (dd, 1H), 3.8-3.2 (m, 12H), 3.1 (m, 2H), 2.9 (bs, 3H), 1.10 (t, 3H).

Example 71

N-(3-{2-[4-(2-Methyl-5-quinolinyl)-1-piperazinyl]ethyl}phenyl)-N'-[2-(2-thienyl)ethyl]urea dihydrochloride (E71)

The title compound was prepared in 46% yield according to the general procedure for the preparation of ureas (Method E) starting from 3-{2-[4-(2-methyl-5-quinolinyl)-1-piperazinyl]ethyl}aniline (D6) and 2-(2-isocyanatoethyl)thiophene.

MS: (ES/+) m/z: 500 [MH$^+$] $C_{29}H_{33}N_5OS$ requires 499.

$^1$H-NMR (400 MHz, d$_6$-DMSO) δ(ppm): 10.48 (bs, 1H), 8.75 (bs, 1H), 8.64 (s, 1H), 7.83 (m, 3H), 7.68 (bs, 1H), 7.48 (bs, 1H), 7.36 (bs, 1H), 7.33 (dd, 1H), 7.19 (t, 1H), 7.15 (dt, 1H), 6.95 (dd, 1H), 6.89 (m, 1H), 6.82 (dt, 1H), 6.3 (t, 1H), 3.71 (bd, 2H), 3.6-3.2 (m, 12H), 3.02 (m, 2H), 2.95 (bs, 2H), 2.81 (bs, 3H).

Example 72

N-(3-{2-[4-(2-Methyl-5-quinolinyl)-1-piperazinyl]ethyl}phenyl)-N'-phenylthiourea dihydrochloride (E72)

The title compound was prepared in 59% yield according to the general procedure for the preparation of ureas (Method E) starting from 3-{2-[4-(2-methyl-5-quinolinyl)-1-piperazinyl]ethyl}aniline (D6) and isothiocyanatobenzene.

MS: (ES/+) m/z: 482[MH$^+$] $C_{29}H_{31}N_5S$ requires 481.

$^1$H-NMR (400 MHz, d$_6$-DMSO) δ(ppm): 10.55 (bs, 1H), 10.09 (s, 1H), 10.07 (s, 1H), 8.75 (bs, 1H), 7.83 (bs, 2H), 7.68 (bs, 1H), 7.51 (s, 1H), 7.49 (d, 2H), 7.4-7.3 (m, 2H), 7.35 (bs, 1H), 7.31 (t, 2H), 7.10 (t, 1H), 7.06 (d, 1H), 3.71 (d, 2H), 3.5-3.2 (m, 8H), 3.09 (m, 2H), 2.80 (bs, 3H).

Example 73

N-Cyclopentyl-N'-(3-{2-[4-(2-methyl-5-quinolinyl)-1-piperazinyl]ethyl}phenyl)urea dihydrochloride (E73)

The title compound was prepared in 96% yield according to the general procedure for the preparation of ureas (Method E) starting from 3-{2-[4-(2-methyl-5-quinolinyl)-1-piperazinyl]ethyl}aniline (D6) and isocyanatocyclopentane.

MS (ES/+) m/z: 458 [MH$^+$] $C_{28}H_{35}N_5O$ requires 457.

$^1$H-NMR (400 MHz, d$_6$-DMSO) δ(ppm): 10.94 (bs, 1H), 8.89 (bs, 1H), 8.51 (s, 1H), 7.93 (bs, 2H), 7.80 (bd, 1H), 7.43 (bs, 2H), 7.17 (m, 2H), 6.81 (m, 1H), 6.35 (bd, 1H), 3.90 (m, 1H), 3.8-3.2 (bm, 10H), 3.04 (dd, 2H), 2.88 (bs, 3H), 1.80 (m, 2H), 1.62 (m, 2H), 1.51 (m, 2H), 1.34 (m, 2H).

Example 74

N-(1-Methylpropyl)-N'-(3-{2-[4-(2-methyl-5-quinolinyl)-1-piperazinyl]ethyl}phenyl)urea dihydrochloride (E74)

The title compound was prepared in 60% yield according to the general procedure for the preparation of ureas (Method E) starting from 3-{2-[4-(2-methyl-5-quinolinyl)-1-piperazinyl]ethyl}aniline (D6) and 2-isocyanatobutane.

MS: (ES/+) m/z: 446 [MH$^+$] $C_{27}H_{35}N_5O$ requires 445.

$^1$H-NMR (400 MHz, d$_6$-DMSO) δ(ppm): 11.07 (bs, 1H), 8.91 (bs, 1H), 8.57 (s, 1H), 7.95 (bm, 2H), 7.81 (bd, 1H), 7.43 (bs, 2H), 7.17 (m, 2H), 6.80 (m, 1H), 6.17 (bd, 1H), 3.8-3.2 (bm, 11H), 3.06 (dd, 1H), 2.89 (bs, 3H), 1.39 (q, 1H), 1.04 (d, 3H), 0.85 (t, 3H).

Example 75

N-Ethyl-N'-(3-{2-[4-(2-methyl-5-quinolinyl)-1-piperazinyl]ethyl}phenyl)urea dihydrochloride (E75)

The title compound was prepared in 95% yield according to the general procedure for the preparation of ureas (Method E) starting from 3-{2-[4-(2-methyl-5-quinolinyl)-1-piperazinyl]ethyl}aniline (D6) and isocyanatoethane.

MS: (ES/+) m/z: 418 [MH$^+$] $C_{25}H_{31}N_5O$ requires 417.

$^1$H-NMR (400 MHz, d$_6$-DMSO) δ(ppm): 10.89 (bs, 1H), 8.60 (bs, 1H), 8.90 (s, 1H), 7.92 (bs, 2H), 7.80 (bs, 1H), 7.44 (s, 2H), 7.19 (m, 2H), 6.81 (m, 1H), 3.71 (d, 2H), 3.6-3.2 (m, 10H), 3.07 (m, 2H), 2.87 (bs, 3H), 1.02 (t, 3H).

Example 76

N-(2-Methyl phenyl)-N'-(3-{2-[4-(2-methyl-5-quinolinyl)-1-piperazinyl]ethyl}phenyl)urea dihydrochloride (E76)

The title compound was prepared in 60% yield according to the general procedure for the preparation of ureas (Method E) starting from 3-{2-[4-(2-methyl-5-quinolinyl)-1-piperazinyl]ethyl}aniline (D6) and 1-isocyanato-2-methylbenzene.

MS: (ES/+) m/z: 480 [MH$^+$] $C_{30}H_{33}N_5O$ requires 479.

$^1$H-NMR (400 MHz, d$_6$-DMSO) δ(ppm): 10.65 (bs, 1H), 9.37 (s, 1H), 8.80 (d, 1H), 8.13 (s, 1H), 7.85 (m, 2H), 7.79 (d, 1H), 7.72 (bs, 1H), 7.52 (s, 1H), 7.37 (bs, 1H), 7.25 (m, 1H), 7.09 (m, 2H), 6.88 (m, 2H), 3.69 (d, 2H), 3.6-3.2 (m, 6H), 3.06 (m, 2H), 2.81 (bs, 3H), 2.22 (s, 3H).

Example 77

N-[3,5-Bis(trifluoromethyl)phenyl]-N'-(3-{2-[4-(2-methyl-5-quinolinyl)-1-piperazinyl]ethyl}phenyl) urea dihydrochloride (E77)

The title compound was prepared in 60% yield according to the general procedure for the preparation of ureas (Method E) starting from 3-{2-[4-(2-methyl-5-quinolinyl)-1-piperazinyl]ethyl}aniline (D6) and 1-isocyanato-3,5-bis(trifluoromethyl)benzene.

MS:(ES/+) m/z: 602 [MH$^+$] C$_{31}$H$_{29}$F$_6$N$_5$O requires 601.
$^1$H-NMR (400 MHz, d$_6$-DMSO) δ(ppm): 10.6 (b, 1H), 10.06 (s, 1H), 9.41 (s, 1H), 8.85 (bs, 1H), 8.15 (s, 2H), 7.9 (bs, 2H), 7.78 (bs, 1H), 7.66 (s, 1H), 7.6 (s, 1H), 7.43 (bs, 1H), 7.32 (d, 2H), 6.99 (t, 1H), 3.76 (bd, 2H), 3.4-3.7 (bm, 6H), 3.29 (t, 2H), 3.13 (dd, 2H), 2.87 (bs, 3H).

Example 78

N-Methyl-N-(3-{2-[4-(2-methyl-5-quinolinyl)-1-piperazinyl]ethyl}phenyl)-N'-phenylurea dihydrochloride salt The title compound was prepared in 85% yield according to general procedure for the preparation of ureas (Method E) starting from N-methyl-3-{2-[4-(2-methyl-5-quinolinyl)-1-piperazinyl]ethyl}aniline (D7) and isocyanatobenzene.

MS: (ES) m/z: 480 [MH$^+$]. C$_{30}$H$_{35}$Cl$_2$N$_5$O requires 479.
$^1$H-NMR (400 MHz, d$_6$-DMSO) δ(ppm): 10.90 (1H, bs), 8.80 (1H, bs), 8.18 (1H, s), 7.88 (2H, bs), 7.75 (1H, bs), 7.43 (2H, d), 7.37 (1H, d), 7.43 (1H, d), 7.30 (1H, bs), 7.25-7.15 (2H, m), 7.19 (2H, dt), 6.92 (1H, tt), 3.69 (4H, br d), 3.60-3.20 (6H, m), 3.28 (3H, s), 3.12 (2H, m), 2.85 (2H, s).

Example 79

1-(3-{2-[4-(2-Methyl-5-quinolinyl)-1-piperazinyl]ethyl}phenyl)-3-phenyl-2-imidazolidinone dihydrochloride salt (E79)

The title compound was prepared in 50% yield according to the general procedure for the preparation of ureas from arylbromides (Method A) starting from 5-{4-[2-(3-bromophenyl)ethyl]-1-piperazinyl}-2-methylquinoline (D14) and 1-phenyl-2-imidazolidinone using 3.0 equiv. of CuI and N,N'-dimethylethylenediamine.

MS: (ES/+) m/z: 492 [MH$^+$]. C$_{31}$H$_{33}$N$_5$O requires 491.
$^1$H-NMR (400 MHz, d$_6$-DMSO) δ(ppm):11.0 (1H, br s), 8.90 (1H, br s), 7.94 (2H, br s), 7.80 (1H, br s), 7.71 (1H, br s), 7.66 (2H, d), 7.51 (1H, br d), 7.39 (1H, m), 7.09 (1H, m), 7.05 (1H, d), 4.01 (4H, s), 3.80-3.20 (10H, m), 3.17 (2H, dd), 2.90 (2H, br s).

Example 80

1-[4-(Methyloxy)phenyl]-3-(3-{2-[4-(2-methyl-5-quinolinyl)-1-piperazinyl]ethyl}phenyl)-2-imidazolidinone dihydrochloride salt (E80)

The title compound was prepared in 16% yield according to the general procedure for the preparation of ureas from arylbromides (Method A) starting from 5-{4-[2-(3-bromophenyl)ethyl]-1-piperazinyl}-2-methylquinoline (D14) and 1-[4-(methyloxy)phenyl]-2-imidazolidinone using 6.0 equiv. of CuI and N,N'-dimethylethylenediamine, which were added in two different portions of 3.0 equiv.

MS: (ES/+) m/z: 522 [MH$^+$]. C$_{23}$H$_{35}$N$_5$O$_2$ requires 521.
$^1$H-NMR (400 MHz, d$_6$-DMSO) δ(ppm): 10.57 (1H, br s), 8.76 (2H, br s), 7.84 (2H, br s), 7.69 (1H, br s), 7.68 (1H, s), 7.52 (d, 2H), 7.46 (d, 1H), 7.37 (br s, 1H), 7.36 (t, 1H), 7.01 (1H, d), 6.94 (2H, d), 3.95 (4H, s), 3.74 (3H, s), 3.72-3.13 (12H, m), 2.82 (3H, br s).

Example 81

1-[2-(Methyloxy)phenyl]-3-(3-{2-[4-(2-methyl-5-quinolinyl)-1-piperazinyl]ethyl}phenyl)-2-imidazolidinone dihydrochloride salt (E81)

The title compound was prepared in 65% yield according to the general procedure for the preparation of ureas from arylbromides (Method A) starting from 5-{4-[2-(3-bromophenyl)ethyl]-1-piperazinyl}-2-methylquinoline (D14) and 1-[2-(methyloxy)phenyl]-2-imidazolidinone using 6.0 equiv. of CuI and N,N'-dimethylethylenediamine, which were added in two different portions of 3.0 equiv.

MS: (ES/+) m/z: 522 [MH$^+$]. C$_{23}$H$_{35}$N$_5$O$_2$ requires 521.
$^1$H-NMR (400 MHz, d$_6$-DMSO) δ(ppm): 10.93 (1H, br s), 8.88 (1H, br s), 7.93 (2H, br s), 7.79 (1H, br s), 7.67 (1H, br s), 7.48 (1H, dd), 7.44 (1H, br s), 7.37 (1H, t), 7.32 (2H, m), 7.14 (1H, br d), 7.01 (2H, m), 4.00 (2H, dd), 3.86 (2H, m), 3.84 (3H, s), 3.75 (2H, br d), 3.70-3.20 (8H, m), 3.15 (2H, dd), 2.89 (3H, br s).

Example 82

1-(2-Methyl phenyl)-3-(3-{2-[4-(2-methyl-5-quinolinyl)-1-piperazinyl]ethyl}phenyl)-2-imidazolidinone dihydrochloride salt (E82)

The title compound was prepared in 65% yield according to the general procedure for the preparation of ureas from arylbromides (Method A) starting from 5-{4-[2-(3-bromophenyl)ethyl]-1-piperazinyl}-2-methylquinoline (D14) and 1-(2-methylphenyl)-2-imidazolidinone using 3.0 equiv. of CuI and N,N'-dimethylethylenediamine.

MS: (ES/+) m/z: 506 [MH$^+$]. C$_{32}$H$_{35}$N$_5$O requires 505.
$^1$H-NMR (400 MHz, d$_6$-DMSO) δ(ppm): 10.90 (1H, br s), 8.90 (1H, br s), 7.93 (br s, 2H), 7.80 (1H, br s), 7.67 (1H, s), 7.49 (dd, 1H), 7.44 (1H, br s), 7.40-7.20 (m, 5H), 7.02 (1H, dd), 4.03 (2H, t), 3.88 (2H, t), 3.74 (2H, br d), 3.70-3.20 (8H, m), 3.15 (2H, dd), 2.89 (3H, br s), 2.26 (3H, s).

Example 83

1-(3-Methyl phenyl)-3-(3-{2-[4-(2-methyl-5-quinolinyl)-1-piperazinyl]ethyl}phenyl)-2-imidazolidinone dihydrochloride salt (E83)

The title compound was prepared in 55% yield according to the general procedure for the preparation of ureas from arylbromides (Method A) starting from 5-{4-[2-(3-bromophenyl)ethyl]-1-piperazinyl}-2-methylquinoline (D14) and 1-(3-methylphenyl)-2-imidazolidinone using 10 mol % of CuI and N,N'-dimethylethylenediamine.

MS: (ES/+) m/z: 506 [MH$^+$]. C$_{32}$H$_{35}$N$_5$O requires 505.
$^1$H-NMR (400 MHz, d$_6$-DMSO) δ(ppm): 10.80 (1H, br s), 8.85 (1H, br s), 7.89 (2H, br s), 7.76 (1H, br s), 7.70 (1H, s), 7.48 (1H, s), 7.45 (1H, d), 7.42 (2H, br m), 7.37 (1H, t), 7.24 (1H, t), 7.02 (1H, d), 6.89 (1H, d), 3.98 (4H, s), 3.74 (2H, br d), 3.60-3.30 (8H, m), 3.14 (2H, dd), 2.86 (3H, br s), 2.32 (3H, s).

Example 84

1-(4-Methyl phenyl)-3-(3-{2-[4-(2-methyl-5-quinolinyl)-1-piperazinyl]ethyl}phenyl)-2-imidazolidinone dihydrochloride salt (E84)

The title compound was prepared in 65% yield according to the general procedure for the preparation of ureas from arylbromides (Method A) starting from 5-{4-[2-(3-bromophenyl)ethyl]-1-piperazinyl}-2-methylquinoline (D14) and 1-(4-methylphenyl)-2-imidazolidinone using 3.0 equiv. of CuI and N,N'-dimethylethylenediamine.

MS: (ES/+) m/z: 506 [MH$^+$]. $C_{32}H_{35}N_5O$ requires 505.

$^1$H-NMR (400 MHz, d$_6$-DMSO) δ(ppm):10.94 (1H, br s), 8.90 (1H, br s), 7.94 (2H, br s), 7.80 (1H, br s), 7.71 (1H, br s), 7.53 (2H, d), 7.49 (22H, d), 7.45 (1H, br s), 7.38 (1H, t), 7.19 (2H, d), 7.04 (1H, d), 3.99 (4H, s), 3.75 (2H, br d), 3.70-3.30 (8H, m), 3.16 (2H, dd), 2.90 (3H, br s), 2.00 (3H, s).

General Procedure for the Synthesis of Cyclic Ureas and Carbamates and their Corresponding Dihydrochloride Salts Starting from 3-{2-[4-(2-methyl-5-quinolinyl)-1-piperazinyl]ethyl}aniline (D3): Method G Diisopropylethylamine (1.5 eq) and a chloroformate or isocyanate (1.2 eq) were added sequentially to a stirred solution of 3-{2-[4-(2-methyl-5-quinolinyl)-1-piperazinyl]ethyl}aniline (1 eq) in dichloromethane at 0° C. The solution was stirred for 1 hr at room temperature, then diluted with dichloromethane and washed with a saturated aqueous solution of NH$_4$Cl and brine and then dried over Na$_2$SO$_4$. The solution was concentrated under reduced pressure. The crude material was dissolved in dimethylformamide, cooled to 0° C., and NaH (1.1 eq) was added portionwise under an inert atmosphere. The mixture was stirred for 2 hrs at room temperature, then the solvent was removed by means of an SCX cartridge. The crude material was purified on SPE cartridge (Silica) eluting with a gradient from dichloromethane/MeOH 99/1 to dichloromethane/MeOH 98/2 affording the final compound (yields ranged from 22 to 87%). The free base could be converted into its dihydrochloride salt by dissolving the compound in Et$_2$O and MeOH and adding an 1M ethereal solution of HCl (2.1 eq) dropwise. A yellow solid precipitated and the suspension was stirred for 15 min. The solvent was removed under reduced pressure affording a crude material which was triturated with Et$_2$O. The final compound was then recovered by filtration (yield quantitative).

Example 85

1-(3-{2-[4-(2-Methyl-5-quinolinyl)-1-piperazinyl]ethyl}phenyl)-2-imidazolidinone dihydrochloride (E85)

The title compound was prepared in 22% yield according to the general procedure for the synthesis of cyclic ureas and carbamates (Method G) starting from 3-{2-[4-(2-methyl-5-quinolinyl)-1-piperazinyl]ethyl}aniline (D3) and 1-chloro-2-isocyanatoethane, via the free base 1-(3-{2-[4-(2-Methyl-5-quinolinyl)-1-piperazinyl]ethyl}phenyl)-2-imidazolidinone.

MS: (ES) m/z: 416 [MH$^+$]. $C_{25}H_{29}N_5O$ requires 415.

$^1$H-NMR (400 MHz, d$_6$-DMSO) δ(ppm): 10.60 (bs, 1H), 8.77 (s, 1H), 7.85 (s, 2H), 7.71 (s, 1H), 7.59 (s, 1H), 7.38 (dd, 1H), 7.28 (t, 1H), 6.96 (bs, 1H), 6.92 (d, 1H), 3.83 (m, 2H), 3.71 (d, 2H), 3.7-3.2 (m, 10H), 3.08 (m, 2H), 2.82 (bs, 3H).

Alternative Preparation of 1-(3-{2-[4-(2-Methyl-5-quinolinyl)-1-piperazinyl]ethyl}phenyl)-2-imidazolidinone Methyl (3-aminophenyl)acetate hydrochloride 3-Aminophenylacetic acid (1 wt) was suspended in methanol (5 vol) under nitrogen at 20° C. Chlorotrimethylsilane (1.26 vol) was added over 60 minutes at 20° C. The reaction mixture was stirred at 20° C. for one hour, then concentrated under reduced pressure to 3 vol. Methyl-t-butyl ether (4 vol) was added and the resulting suspension was stirred at room temperature for 18 hours. The solid was collected by filtration, washing with methyl-t-butyl ether (4×1 vol). The material was dried in oven at 40° C. for 5 hours to give the title compound.

MS: (ES) m/z: 166 [MH$^+$]. $C_9H_{11}NO_2$ requires 165.

$^1$H-NMR (300 MHz, d$_6$-DMSO) δ(ppm): 7.40 (m, 1H), 7.19 (m, 3H), 3.74 (s, 2H), 3.58 (s, 3H).

Methyl [3-(2-oxo-1-imidazolidinyl)phenyl]acetate

Methyl (3-aminophenyl)acetate hydrochloride was suspended in dichloromethane (7 vol) under nitrogen. Diisopropylethylamine (1.04 vol) was added at 20° C. over 30 minutes, and the reaction mixture was stirred for 30 minutes at 20° C. 2-Chloroethyl isocyanate (0.44 vol) was added dropwise at 20° C. over 100 minutes. The reaction mixture was stirred at 20° C. for three hours. A saturated solution of ammonium chloride (5 vol) was added dropwise over 10 mins and the resultant mixture was stirred for ten minutes. The organic phase was separated and washed with water (5 vol). Tetrahydrofuran (2×3 vol) was added and the mixture was concentrated to 2 vol. Dry tetrahydrofuran (5 vol) was added, and the mixture was concentrated to 2 vol. Dry THF (3 vol) was added, under nitrogen at 20° C. The reaction mixture was cooled to 0° C., and potassium tert-butoxide (0.56 wt) was added portion-wise in 5 stages, allowing 20 minutes between two subsequent additions. The reaction mixture was stirred at 20° C. for one hour. Hydrochloric acid (0.5N, 2 vol) was added dropwise over 20 minutes. Ethyl acetate (10 vol) was added and the organic phase was separated. The organic layer was washed with aqueous sodium hydrogencarboante solution (4%, 2 vol) and brine (2 vol), and the organic layer was then evaporated to dryness under vacuum to give the title compound (overall yield: 90% w/w).

$^1$H-NMR (300 MHz, CDCl$_3$) δ(ppm): 7.50-7.45 (m, 2H), 7.30 (m, 1H), 7.00 (d, 1H), 4.98 (br. s, 1H), 4.95 (t, 2H), 3.68 (s, 3H), 3.62 (s, 2H), 3.54 (t, 2H).

1-[3-(2-Hydroxyethyl)phenyl]-2-imidazolidinone

Methyl [3-(2-oxo-1-imidazolidinyl)phenyl]acetate was dissolved in dry dichloromethane (10 vol). Lithium borohydride (2M solution in THF, 4.3 vol) was added dropwise over 1 hour at 20° C. The resulting suspension was stirred at 20° C. for 2.5 hours. Water (2 vol) is added dropwise at 20° C. over 60 minutes. The resulting suspension was concentrated to 2 vol and aqueous ammonium chloride solution (7%, acidity corrected with 10% hydrochloric acid to pH 3, 3 vol) was added. The suspension was stirred at 20° C. for 2 hours then filtered. The filter-cake was washed thoroughly with aqueous ammonium chloride solution (7%, acidity corrected with 10% hydrochloric acid to pH 3, 2 vol) and water (2 vol) until the filtrate had an acidity of pH 7. The filter-cake was dried at 80° C. to give the title compound (75% th.).

¹H-NMR (300 MHz, d₆-DMSO) δ(ppm): 7.36-7.27 (m, 2H), 7.19 (t, 1H), 7.86 (m, 1H), 7.81 (d, 1H), 4.58 (br. s, 1H), 3.60 (t, 2H), 3.52 (m, 2H), 3.35 (t, 2H), 2.64 (t, 2H).

2-[3-(2-Oxo-1-imidazolidinyl)phenyl]ethyl methanesulfonate

1-[3-(2-Hydroxyethyl)phenyl]-2-imidazolidinone was suspended in DMF (4 vol) and heated to 35° C. until a clear solution was obtained. Triethylamine (1 vol) was added dropwise at 30° C. over 15 minutes. The mixture was cooled to 20° C. and methanesulfonyl chloride (0.46 vol) was added 30 mins. The resulting suspension was stirred at 20° C. for 15 minutes. Dichloromethane (10 vol) was added, and the organic layer was washed with brine/water (1:1) (5 vol), and then water (3×5 vol). The organic phase was concentrated to 1 vol, and methanol was added (4 vol), if complete dissolution was not obtained, the mixture was heated to 35° C. in order to dissolve the solid. Methyl-t-butyl ether (10 vol) was added and the suspension was left to stand for 18 hours at room temperature. The suspension was filtered; the filter-cake was washed with methyl-t-butyl ether (2 vol). The solid was dried at 40° C. for 18 hours to give the title compound (70% th).

¹H-NMR (300 MHz, CDCl₃) δ(ppm): 7.54 (s, 1H), 7.40-7.25 (m, 2H), 6.92 (d, 1H), 4.72 (br. s, 1H), 4.41 (t, 2H), 3.92 (t, 2H), 3.60 (t, 2H), 3.09 (t, 2H), 2.87 (s, 3H).

Alternatively, 1-[3-(2-hydroxyethyl)phenyl]-2-imidazolidinone was suspended in acetonitrile (5 vol) at room temperature and under nitrogen. Triethylamine (1 vol) was added dropwise over 15 minutes. The mixture was cooled to 0° C. and methanesulfonyl chloride (0.73 vol) was added over 30 minutes. The reaction mixture was stirred at room temperature for 2 hours, then diluted with ethyl acetate (10 vol). The mixture was washed with a saturated solution of ammonium chloride (2×3 vol), followed by water-brine 1:1 (2×3 vol). The organic phase was concentrated to 5 vol, ethyl acetate (5 vol) was added and the solution was evaporated to dryness, yielding the title compound as a cream-coloured solid (yield: 90% th).

2-Methyl-5-quinolinyl trifluoromethanesulfonate

5-Hydroxy-2-methylquinoline hydrobromide (WO2002034754, Chem. Abstr. 136:355241, 1 wt, 1 eq) was suspended in ethyl acetate (20 vol) and a saturated solution of sodium hydrogen carbonate (7 vol) was added. The organic layer was washed with a saturated solution of sodium hydrogen carbonate (7 vol) and the two layers were separated. The organic layer was concentrated to 2 vol then ethyl acetate (2×3 vol) was added and the mixture was concentrated to 2 vol each time. Toluene was added (2×10 vol) and the mixture was concentrated to 2 vol each time to give a suspension of 5-hydroxy-2-methylquinoline. Toluene (9 vol) and pyridine (0.68 vol, 1.33 eq) were added under nitrogen at room temperature. The mixture was cooled to 0° C. and triflic anhydride (1.27 vol, 1.2 eq) was added dropwise maintaining the temperature at 0° C., then warming to 25° C. for 3 hours. A saturated aqueous solution of ammonium chloride (7 vol) was added and the mixture was stirred for 10 minutes. The two layers were separated and the organic layer was washed with water (7 vol), a 4% solution of sodium hydrogencarbonate (7 vol), water (7 vol), then concentrated to 3 volumes. Toluene (2×7 vol) was added and the mixture concentrated to 3 volumes to give a crude brown solution of the title compound (70% th), which was used without further purification.

1,1-Dimethylethyl 4-(2-methyl-5-quinolinyl)-1-piperazinecarboxylate

A solution of 2-methyl-5-quinolinyl trifluoromethanesulfonate (1wt, 1 eq) in toluene (7 vol) was degassed under reduced pressure then flushed with nitrogen. To the mixture were added N-Boc-piperazine (1.05 eq), milled cesium carbonate (1.5 eq), (+/−)-bis(diphenylphosphino)-1,1'-binaphthyl (BINAP, 0.15 eq) and palladium acetate (0.05 eq). The resulting mixture was stirred at 95° C. for 16 hours. The solution was cooled and concentrated to approx. 4 vol and 10 vol of cyclohexane were added giving a suspension. The suspension was stirred for 30 minutes and filtered over a pad of Silica Gel (approx 2.5 vol). The filtrate was washed with 10 vol of water and concentrated under reduced pressure to give the title compound as a brown solid, which was carried through directly to the next stage.

2-Methyl-5-(1-piperazinyl)quinoline

To a solution of 1,1-dimethylethyl 4-(2-methyl-5-quinolinyl)-1-piperazinecarboxylate in 2-propanol (3 vol) was added dropwise hydrochloric acid (37%, 3 vol). The mixture was stirred at 40° C. for 1.5 hours then concentrated. Water (30 vol) was added and the solution was extracted with ethyl acetate (3×20 vol). The aqueous layer was basified with an aqueous sodium carbonate solution then extracted with dichloromethane (5×40 vol). The combined organic extracts were dried and evaporated to give the title compound as an off-white solid (80% th, 2 steps).

1-(3-{2-[4-(2-Methyl-5-quinolinyl)-1-piperazinyl]ethyl}phenyl)-2-imidazolidinone (E85)

2-[3-(2-Oxo-1-imidazolidinyl)phenyl]ethyl methanesulfonate (1.32 wt) and 2-methyl-5-(1-piperazinyl)quinoline (1 wt.) were suspended in acetonitrile (5 vol) at room temperature under nitrogen. Diisopropylethylamine (1.53 vol) was added dropwise over 30 minutes, and the mixture was then stirred at 75° C. for 4 hours. The reaction mixture was cooled to room temperature, concentrated to 2 vol, and diluted with ethyl acetate (7 vol). The organic layer was washed with saturated aqueous ammonium chloride solution (2×3 vol), followed by water (1×3 vol). The organic layer was evaporated to dryness, yielding the title compound as a brown foam (70% th).

Sulfate salt of E85: 1-(3-{2-[4-(2-Methyl-5-quinolinyl)-1-piperazinyl]ethyl}phenyl)-2-imidazolidinone sulfate 1-(3-{2-[4-(2-Methyl-5-quinolinyl)-1-piperazinyl]ethyl}phenyl)-2-imidazolidinone (300 mg, 1 wt) is suspended in methanol (6.0 ml, 20 vol) at room temperature under nitrogen. A solution of sulfuric acid (71 mg, 1 eq) in methanol is dosed. The clear solution is seeded and solid crystallization is observed. The slurry is stirred 16 hrs at room temperature. The solid is filtered and dried at room temperature under vacuum to give the desired salt.

1-(3-{2-[4-(2-Methyl-5-quinolinyl)-1-piperazinyl]ethyl}phenyl)-2-imidazolidinone may exist as two different physical forms, form 1 or form 2.

1-(3-{2-[4-(2-Methyl-5-quinolinyl)-1-piperazinyl]
ethyl}phenyl)-2-imidazolidinone, form 1

The free-base was completely dissolved in DCM (10 volumes) at reflux. The mixture was concentrated under vacuum (rotary evaporator) at 40° C. (external temperature), until crystallisation initiated (mixture reduced to 2-3 volumes). The suspension was cooled to 25° C., then methyl tert-butyl ether (10 volumes) was added with stirring. The suspension was stirred at 25° C. for 18 hours. The precipitate was filtered off, washed with methyl tert-butyl ether (1 vol) and dried at 40° C. for 18 hours to give the title compound; m.p. 170° C.

1-(3-{2-[4-(2-Methyl-5-quinolinyl)-1-piperazinyl]
ethyl}phenyl)-2-imidazolidinone, form 2

The free-base was completely dissolved in DCM (10 volumes) at reflux. The solution was cooled to 25° C., then methyl tert-butyl ether (10 volumes) was added with stirring. The suspension was stirred at 25° C. overnight. The precipitate thus formed was filtered off, washed with methyl tert-butyl ether-DCM (1:1, 2×1 volume) and dried at 40° C. for 18 hours to give the title compound; m.p. 164° C.

Example 86

3-(3-{2-[4-(2-Methyl-5-quinolinyl)-1-piperazinyl]
ethyl}phenyl)-1,3-oxazolidin-2-one dihydrochloride
(E86)

The title compound was prepared in 81% yield according to the general procedure for the synthesis of cyclic ureas and carbamates (Method G) starting from 3-{2-[4-(2-methyl-5-quinolinyl)-1-piperazinyl]ethyl}aniline (D3) and (2-bromoethyl)carbamic chloride.

MS: (ES) m/z: 417 [MH$^+$]. $C_{25}H_{28}N_4O_2$ requires 416.
$^1$H-NMR (400 MHz, d$_6$-DMSO) δ(ppm): 10.99 (bs, 1H), 8.87 (bm, 1H), 7.91 (bm, 2H), 7.79 (bm, 1H), 7.57 (s, 1H), 7.40 (m, 3H), 7.08 (d, 1H), 4.43 (t, 2H), 4.07 (t, 2H), 3.72-3.3 (m, 10H), 3.15 (m, 2H), 2.87 (bs, 3H).

Example 87

1-(3-{2-[4-(2-Methyl-5-quinolinyl)-1-piperazinyl]
ethyl}phenyl)tetrahydro-2(1H)-pyrimidinone dihydrochloride (E87)

The title compound was prepared in 87% yield according to the general procedure for the synthesis of cyclic ureas and carbamates (Method G) starting from 3-{2-[4-(2-methyl-5-quinolinyl)-1-piperazinyl]ethyl}aniline (D3) and 1-chloro-3-isocyanatopropane.

MS: (ES) m/z: 430 [MH$^+$]. $C_{26}H_{31}N_5O$ requires 429.
$^1$H-NMR (400 MHz, d$_6$-DMSO) δ(ppm): 11.05 (bs, 1H), 8.94 (s, 1H), 7.97 (s, 2H), 7.84 (d, 1H), 7.46 (bs, 1H), 7.30 (m, 2H), 7.19 (dd, 1H), 7.08 (d, 1H), 6.58 (s, 1H), 3.70 (bm, 4H), 3.63 (t, 2H), 3.6-3.3 (bm, 6H), 3.24 (t, 2H), 3.12 (m, 2H), 2.91 (s, 3H), 1.95 (t, 2H).

Example 88

3-(3-{2-[4-(2-Methyl-5-quinolinyl)-1-piperazinyl]
ethyl}phenyl)tetrahydro-2H-1,3-oxazin-2-one dihydrochloride (E88)

The title compound was prepared in 75% yield according to the general procedure for the synthesis of cyclic ureas and carbamates (Method G) starting from 3-{2-[4-(2-methyl-5-quinolinyl)-1-piperazinyl]ethyl}aniline (D3) and (3-chloropropyl)carbamic chloride. MS: (ES) m/z: 431 [MH$^+$]. $C_{26}H_{30}N_4O_2$ requires 430.

$^1$H-NMR (400 MHz, d$_6$-DMSO) δ(ppm): 10.89 (bs, 1H), 8.84 (bm, 1H), 7.89 (bm, 2H), 7.76 (bm, 1H), 7.40 (m, 4H), 7.31 (s, 1H), 4.32 (t, 2H), 3.72-3.3 (m, 10H), 3.66 (t, 2H), 3.13 (m, 2H), 2.85 (bs, 3H), 2.10 (m, 2H).

General Procedure for the Synthesis of Cyclic Amide, Urea, and Carbamate Derivatives of 1-(3-aminophenyl)-2-[4-(2-methyl-5-quinolinyl)-1-piperazinyl]ethanol (D8) and their Corresponding Dihydrochloride Salts Starting Form 1-(3-Acetylphenyl)-2-cyclic Amides, Ureas and Carbamates. Method H AlCl$_3$ (1% w/w) and then bromine (1 eq) was added dropwise to a stirred solution of a 1-(3-acetylphenyl)-2-cyclic amide, urea or carbamate (1 eq) in Et$_2$O or dichloromethane at 0° C. The solution was stirred for 1 hr at room temperature, then diluted with dichloromethane and washed with a saturated aqueous solution of NaHCO$_3$, a saturated aqueous solution of NH$_4$Cl and brine and then dried over Na$_2$SO$_4$. The solution was concentrated under reduced pressure. The crude material was dissolved in dimethylformamide and 2-methyl-5-(1-piperazinyl)quinoline (D3) (1 eq) and Na$_2$CO$_3$ (1.5 eq) were added. The solution was stirred for 2-4 hrs at room temperature. MeOH was then added in equal volume with respect to dimethylformamide, followed by NaBH$_4$ (2 eq) and the solution was stirred for 15 min at room temperature. The solvent was removed by means of an SCX cartridge. The crude material was purified on SPE cartridge (Silica) eluting with a gradient from dichloromethane/MeOH 99/1 to dichloromethane/MeOH 98/2 affording the final compound (yields ranged from 39 to 71%).

The free base could be converted into its dihydrochloride salt by dissolving the compound in Et$_2$O and MeOH and adding an 1M ethereal solution of HCl (2.1 eq) dropwise. A yellow solid precipitated and the suspension was stirred for 15 min. The solvent was removed under reduced pressure affording a crude material which was triturated with Et$_2$O. The final compound was then recovered by filtration (yield quantitative).

Example 89

1-(3-{1-Hydroxy-2-[4-(2-methyl-5-quinolinyl)-1-piperazinyl]ethyl}phenyl)-2-pyrrolidinone dihydrochloride (E89)

The title compound was prepared in 25% yield according to the general procedure for the synthesis of cyclic amide, urea and carbamate derivatives of 1-(3-aminophenyl)-2-[4-(2-methyl-5-quinolinyl)-1-piperazinyl]ethanol (Method H) starting from 1-(3-acetylphenyl)-2-pyrrolidinone (D9) and 2-methyl-5-(1-piperazinyl)quinoline (D3).

MS: (ES) m/z: 431 [MH$^+$]. $C_{26}H_{30}N_4O_2$ requires 430.
$^1$H-NMR (400 MHz, d$_6$-DMSO) δ(ppm): 10.2 (bs, 1H), 8.8 (bs, 1H), 7.86 (bs, 2H), 7.81 (s, 1H), 7.73 (bs, 1H), 7.54 (dd, 1H), 7.40 (t, 1H), 7.38 (bs, 1H), 7.20 (d, 1H), 6.36 (bs, 1H), 5.18 (dd, 1H), 3.83 (t, 2H), 3.76 (bt, 2H), 3.7-3.2 (m, 8H), 2.83 (bs, 3H), 2.5 (m, 2H), 2.07 (q, 2H).

Example 90

1-(3-{1-Hydroxy-2-[4-(2-methyl-5-quinolinyl)-1-piperazinyl]ethyl}phenyl)-2-azetidinone dihydrochloride (E90)

The title compound was prepared in 39% yield according to the general procedure for the synthesis of cyclic amide, urea and carbamate derivatives of 1-(3-aminophenyl)-2-[4-(2-methyl-5-quinolinyl)-1-piperazinyl]ethanol (Method H) starting from 1-(3-acetylphenyl)-2-azetidinone (D10) and 2-methyl-5-(1-piperazinyl)quinoline (D3).

MS: (ES) m/z: 417 [MH$^+$]. $C_{25}H_{28}N_4O_2$ requires 416.

$^1$H-NMR (400 MHz, d$_6$-DMSO) δ(ppm): 10.35 (bs, 1H), 8.84 (bs, 1H), 7.91 (bs, 2H), 7.77 (bs, 1H), 7.51 (s, 1H), 7.40 (t+bs, 2H), 7.23 (d, 1H), 7.15 (d, 1H), 6.38 (bs, 1H), 5.19 (d, 1H), 3.8-3.2 (m, 12H), 3.09 (t, 2H), 2.86 (bs, 3H).

Example 91

3-(3-{1-Hydroxy-2-[4-(2-methyl-5-quinolinyl)-1-piperazinyl]ethyl}phenyl)-1,3-oxazolidin-2-one dihydrochloride (E91)

The title compound was prepared in 34% yield according to the general procedure for the synthesis of cyclic amide, urea and carbamate derivatives of 1-(3-aminophenyl)-2-[4-(2-methyl-5-quinolinyl)-1-piperazinyl]ethanol (Method H) starting from 1-(3-acetylphenyl)-1,3-oxazolidin-2-one (D11) and 2-methyl-5-(1-piperazinyl)quinoline (D3).

MS: (ES) m/z: 433 [MH$^+$]. $C_{25}H_{28}N_4O_3$ requires 432.

$^1$H-NMR (400 MHz, d$_6$-DMSO) δ(ppm): 10.3 (bs, 1H), 8.8 (bs, 1H), 7.89 (bs, 2H), 7.76 (bs, 2H), 7.44 (m, 3H), 7.20 (d, 1H), 6.4 (bs, 1H), 5.21 (dd, 1H), 4.45 (t, 2H), 4.06 (t, 2H), 3.76 (bt, 2H), 3.7-3.2 (m, 8H), 2.85 (bs, 3H).

Example 92

1-(3-{1-Hydroxy-2-[4-(2-methyl-5-quinolinyl)-1-piperazinyl]ethyl}phenyl)-2-imidazolidinone dihydrochloride (E92)

The title compound was prepared in 26% yield according to the general procedure for the synthesis of cyclic amide, urea and carbamate derivatives of 1-(3-aminophenyl)-2-[4-(2-methyl-5-quinolinyl)-1-piperazinyl]ethanol (Method H) starting from 1-(3-acetylphenyl)-2-imidazolidinone (D12) and 2-methyl-5-(1-piperazinyl)quinoline (D3).

MS: (ES) m/z: 432 [MH$^+$]. $C_{25}H_{29}N_5O_2$ requires 431.

$^1$H-NMR (400 MHz, d$_6$-DMSO) δ(ppm): 10.2 (bs, 1H), 8.8 (bs, 1H), 7.87 (bs, 2H), 7.74 (bs, 2H), 7.43 (dd, 1H), 7.40 (bs, 1H), 7.33 (t, 1H), 7.06 (d, 1H), 6.98 (bs, 1H), 6.3 (bs, 1H), 5.14 (dd, 1H), 3.84 (t, 2H), 3.78 (bt, 2H), 3.7-3.0 (m, 10H), 2.84 (bs, 3H).

Example 93

1-(3-{2-[4-(2-Methyl-5-quinolinyl)-1-piperazinyl]ethyl}phenyl)-2,5-pyrrolidinedione (E93)

Dihydro-2,5-furandione (2 eq) was added to a stirred solution of 3-{2-[4-(2-methyl-5-quinolinyl)-1-piperazinyl]ethyl}aniline (D6) (1 eq) in toluene/pyridine (3:2) at room temperature under an inert atmosphere. The solution was stirred for 30 min at room temperature, then irradiated in a microwave reactor (PersonalChemistry Emrys™ Optimiser, 300 W, 170° C., 20 min, 4 cycles), diluted with dichloromethane and washed with a saturated aqueous solution of NH$_4$Cl and brine and then dried over Na$_2$SO$_4$. The solution was concentrated under reduced pressure. The crude material was purified on SPE cartridge (Silica) eluting with a gradient from dichloromethane/MeOH 99/1 to dichloromethane/MeOH 98/2 affording the final compound in 76% yield.

The free base was converted into its dihydrochloride salt by dissolving the compound in Et$_2$O and MeOH and adding an 1M ethereal solution of HCl (2.1 eq) dropwise. A yellow solid precipitated and the suspension was stirred for 15 min. The solvent was removed under reduced pressure affording a crude material which was triturated with Et$_2$O to give the title compound.

MS: (ES) m/z: 429 [MH$^+$]. $C_{26}H_{28}N_4O_2$ requires 428.

$^1$H-NMR (400 MHz, d$_6$-DMSO) δ(ppm): 11.1 (bs, 1H), 8.91 (bs, 1H), 7.94 (bs, 2H), 7.81 (bs, 1H), 7.49 (t, 1H), 7.44 (bs, 1H), 7.37 (d, 1H), 7.22 (s, 1H), 7.18 (d, 1H), 3.73 (bm, 2H), 3.59 (bm, 2H), 3.48 (bm, 4H), 3.33 (m, 2H), 3.19 (m, 2H), 2.89 (bs, 3H), 2.80 (bs, 4H).

Example 94

N-(3-{2-[4-(7-Chloro-2-methyl-5-quinolinyl)-1-piperazinyl]ethyl}phenyl)acetamide dihydrochloride (E94)

The title compound was prepared in 65% yield according to the general procedure for the preparation of the amides (Method B) starting from 3-{2-[4-(7-Chloro-2-methyl-5-quinolinyl)-1-piperazinyl]ethyl}aniline (D18) and acetyl chloride.

MS: (ES) m/z: 423 [MH$^+$]. $C_{24}H_{27}ClN_4O$ requires 422.

$^1$H-NMR (400 MHz, d$_6$-DMSO) δ(ppm): 10.68 (bs, 1H), 9.99 (s, 1H), 8.53 (bs, 1H), 7.80 (s, 1H), 7.65 (s, 1H), 7.58 (d, 1H), 7.37 (d, 1H), 7.28 (m, 2H), 6.97 (d, 1H), 4-3.2 (bm, 10H), 3.07 (dd, 1H), 2.74 (s, 3H), 2.04 (s, 3H).

Example 95

N-(3-{2-[4-(7-chloro-2-methyl-5-quinolinyl)-1-piperazinyl]ethyl}phenyl)methanesulfonamide dihydrochloride (E95)

The title compound was prepared in 65% yield using a similar procedure to example E43 starting from 3-{2-[4-(7-Chloro-2-methyl-5-quinolinyl)-1-piperazinyl]ethyl}aniline (D18) and methanesulfonyl chloride.

MS: (ES) m/z: 459 [MH$^+$]. $C_{23}H_{27}ClN_4O_2S$.2HCl requires 458.

$^1$H-NMR (400 MHz, d$_6$-DMSO) δ(ppm): 10.69 (bs, 1H), 9.80 (s, 1H), 8.53 (d, 1H), 7.79 (s, 1H), 7.58 (d, 1H), 7.33 (t, 1H), 7.27 (s, 1H), 7.15 (d, 1H), 7.11 (d, 1H), 7.05 (d, 1H), 3.7-3.2 (bm, 10H), 3.09 (dd, 2H), 3.01 (s, 3H), 2.73 (s, 3H).

Example 96

N$^1$,N$^1$-Dimethyl-N$^2$-(3-{2-[4-(2-methyl-5-quinolinyl)-1-piperazinyl]ethyl}phenyl)glycinamide dihydrochloride (E96)

Diisopropylethylamine (2 eq), NaI (2 eq) and 2-chloro-N,N-dimethylacetamide (1.1 eq) were added sequentially to a stirred solution of 3-{2-[4-(7-chloro-2-methyl-5-quinolinyl)-1-piperazinyl]ethyl}aniline (1 eq) in dimethylformamide at room temperature under an inert atmosphere. The solution was stirred for 2 hrs at 60° C., then the solvent was removed by means of an SCX cartridge. The crude material was purified on SPE cartridge (Silica) eluting with a gradient of dichloromethane/MeOH 99/1 to dichloromethane/MeOH 98/2 affording the final compound in 38% yield.

The free base was converted into its dihydrochloride salt by dissolving the compound in Et$_2$O and MeOH and adding an 1M ethereal solution of HCl (2.1 eq) dropwise. A yellow solid precipitated and the suspension was stirred for 15 min. The solvent was removed under reduced pressure affording a crude material which was triturated with Et$_2$O to give the title compound.

MS: (ES) m/z: 466 [MH$^+$]. C$_{26}$H$_{32}$ClN$_5$O requires 465.

$^1$H-NMR (500 MHz, CD$_3$OD) δ(ppm): 9.19 (d, 1H), 7.95 (d, 1H), 7.90 (d, 1H), 7.62 (d, 1H), 7.45 (t, 1H), 7.32 (bs, 1H), 7.25 (bd, 1H), 7.19 (bd, 1H), 4.37 (bs, 2H), 3.85 (bd, 2H), 3.65 (bm, 4H), 3.60 (dd, 2H), 3.45 (bt, 2H), 3.25 (dd, 2H), 3.06 (s, 3H), 3.02 (s, 3H), 3.01 (s, 3H).

Example 97

2-Methyl-5-(4-{[3-(1H-pyrazol-1-yl)phenyl]acetyl}-1-piperazinyl)quinoline (E97)

EDC•HCl (1.5 eq), HOBt (2 eq) and 2-methyl-5-(1-piperazinyl)quinoline (D3) (1 eq) were added sequentially to a stirred solution of [3-(1H-pyrazol-1-yl)phenyl]acetic acid (D19) (1.1 eq) in dimethylformamide at room temperature under an inert atmosphere. The solvent was removed by means of an SCX cartridge. The crude material was purified on SPE cartridge (Silica) eluting with a gradient from dichloromethane/MeOH 99/1 to dichloromethane/MeOH 98/2 affording the title compound in 74% yield.

MS: (ES) m/z: 412 [MH$^+$]. C$_{25}$H$_{25}$N$_5$O requires 411.

$^1$H-NMR (400 MHz, CDCl$_3$) δ(ppm): 8.36 (d, 1H), 7.93 (d, 1H), 7.75 (d, 1H), 7.71 (s, 1H), 7.69 (s, 1H), 7.58 (d, 1H), 7.55 (t, 1H), 7.42 (t, 1H), 7.25 (m, 2H), 7.00 (d, 1H), 6.46 (s, 1H), 3.87 (s, 2H), 4.0-3.7 (m, 4H), 3.1-2.9 (m, 4H), 2.72 (s, 3H).

Example 98

2-Methyl-5-(4-{2-[3-(1H-pyrazol-1-yl)phenyl]ethyl}-1-piperazinyl)quinoline (E98)

A 1M tetrahydrofuran solution of borane-tetrahydrofuran complex (3 eq) was added to a stirred solution of 2-methyl-5-(4-{[3-(1H-pyrazol-1-yl)phenyl]acetyl}-1-piperazinyl)quinoline (E97) (1 eq) in tetrahydrofuran at room temperature under an inert atmosphere. The solution was heated to 60° C. for 3 hrs. An aqueous 3N solution of HCl was added and the solution was stirred at room temperature for 12 hrs. The solvent was removed under reduced pressure. The crude material was purified by SCX cartridge affording the title compound in 52% yield.

MS: (ES) m/z: 398 [MH$^+$]. C$_{25}$H$_{27}$N$_5$ requires 397.

$^1$H-NMR (300 MHz, CDCl$_3$) δ(ppm): 8.35 (d, 1H), 7.90 (d, 1H), 7.70 (d, 1H), 7.70 (s, 1H), 7.65 (t, 1H), 7.60 (t, 1H), 7.50 (dd, 1H), 7.35 (t, 1H), 7.25 (d, 1H), 7.15 (d, 1H), 7.05 (d, 1H), 6.45 (t, 1H), 3.20 (m, 4H), 3.0-2.7 (m, 8), 2.70 (s, 3H).

Example 99

N-(3-{2-[4-(6-Fluoro-2-methyl-5-quinolinyl)-1-piperazinyl]ethyl}phenyl)acetamide (E99)

1,1-dimethylethyl 4-(6-fluoro-2-methyl-5-quinolinyl)-1-piperazinecarboxylate

A mixture of 5-bromo-6-fluoro-2-methylquinoline (Chem. Pharm. Bull., 1989, 37(8), 2103-8, 0.285 g), 1,1-dimethyl-ethyl 1-piperazinecarboxylate (0.265 g, 1.2 equiv.), Pd(OA)$_2$ (15 mol %, 0.04 g), bis(diphenylphosphino)-1,1'-binaphthyl (BINAP, 30 mol %, 0.221 g), cesium carbonate (1.5 equiv. 0.580 g) and toluene (3.5 mL) were stirred at 120° C. for 20 h in a sealed tube. The mixture was cooled to room temperature and partitioned between ethyl acetate and brine. The organic layer was dried over sodium sulfate, filtered and concentrated. This crude product was purified by flash chromatography [SiO$_2$; DCM-MeOH (99:1)→(90:10)] to afford the title compound as colourless solid (0.270 g, 65% yield).

MS: (ES/+) m/z: 346 [MH$^+$]. C$_{19}$H$_{24}$FN$_3$O$_2$ requires 345.

1H-NMR (300 MHz, CDCl$_3$) (ppm): 8.55 (d, 1H), 7.80 (dd, 1H), 7.40-7.2 (m, 2H), 3.5-2.9 (m, 8H), 2.65 (s, 3H), 1.5 (s, 9H).

6-Fluoro-2-methyl-5-(1-piperazinyl)quinoline

A solution of hydrogen chloride in dioxane (4M, 4 mL) was added to a solution of 1,1-dimethylethyl-4-(6-fluoro-2-methyl-5-quinolinyl)-1-piperazinecarboxylate (0.178 g) in dioxane (4 mL) at 0° C. The resulting mixture was warmed to room temperature and stirred for 15 h. The mixture was concentrated in vacuo and partitioned between aqueous sodium hydroxide solution and DCM. The combined organic phases were washed with brine, dried over sodium sulfate and concentrated to afford the title compound (198 mg, 100% yield).

MS: (ES/+) m/z: 246 [MH$^+$]. C$_{14}$H$_{16}$FN$_3$ requires 245.

1H-NMR (300 MHz, CDCl$_3$) δ(ppm): 8.55 (d, 1H), 7.80 (dd, 1H), 7.40-7.2 (m, 2H), 3.5-2.9 (m, 8H), 2.65 (s, 3H).

6-Fluoro-2-methyl-5-{4-[2-(3-nitrophenyl)ethyl]-1-piperazinyl}quinoline

N,N-Diisopropylethylamine (0.15 mL; 3 eq) was added to a solution of 2-methyl-5-(1-piperazinyl)-6-fluoro quinoline (0.075 g; 1 eq) and 2-(3-nitrophenyl)ethyl methanesulfonate (D4) (0.08; 1.1 eq) in dimethylformamide (3.0 mL). The reaction mixture was heated to 100° C. for 10 hours. The dark solution was concentrated under reduced pressure, diluted with water (3 mL) and brine (1 mL) and extracted into ethyl acetate (3×3 mL). The organic layers were combined, dried over sodium sulfate and concentrated under reduced pressure. The crude was purified by flash chromatography on silica gel, eluting with a gradient from dichloromethane to dichloromethane-methanol (98:2) affording the title compound in 42% yield (0.05 g).

MS; (ES) m/z: 395.2 [MH]$^+$. C$_{22}$H$_{23}$FN$_4$O$_2$ requires 394.

3-{2-[4-(6-Fluoro-2-methyl-5-quinolinyl)-1-piperazinyl]ethyl}aniline

A solution of 6-fluoro-2-methyl-5-{4-[2-(3-nitrophenyl)ethyl]-1-piperazinyl}quinoline (0.05 g; 1 eq) in methanol (3 mL) was added dropwise to a suspension of iron powder (0.05 g; 7 eq) and ammonium chloride (0.05 g; 7 eq) in water (3 mL). The reactants were heated at reflux for 8 hours, with additional amounts of iron powder (total 0.05 g; 7 eq) and ammonium chloride (0.05 g; 7 eq) added in 3 portions during the reaction. The reaction mixture was cooled to room temperature and filtered using a Millipore filter. The filtrate was concentrated under reduced pressure, diluted with water (5 mL) and a saturated aqueous solution of sodium hydrogen carbonate (2 mL) and extracted into ethyl acetate (3×5 mL). The combined organic layers were dried over sodium sulfate and concentrated under reduced pressure to give the title compound in 91% yield (0.04 g).

MS; (ES) m/z: 365 [MH]$^+$. $C_{22}H_{26}N_4$ requires 346.

1H-NMR (300 MHz, d$_6$-DMSO) (ppm): 8.50 (d, 1H), 7.80 (m, 1H), 7.75 (m, 1H), 7.60 (d, 1H), 6.80 (t, 1H), 6.65 (bs, 1H), 6.60 (m, 2H), 3.3-2.8 (bm, 12H), 3.15 (t, 4H), 2.75 (s, 3H).

N-(3-{2-[4-(6-Fluoro-2-methyl-5-quinolinyl)-1 piperazinyl]ethyl}phenyl)acetamide (E99)

The title compound was prepared in 78% yield according to Method B for the preparation of amides starting from 3-{2-[4-(6-fluoro-2-methyl-5-quinolinyl)-1-piperazinyl]ethyl}aniline and acetyl chloride.

MS: (ES) m/z: 407.5 [MH]$^+$. $C_{24}H_{27}FN_4O$ requires 406.

1H-NMR (300 MHz, d$_6$-DMSO) δ(ppm): 9.67 (bs, 1H), 8.50 (d, 1H), 7.73 (dd, 1H), 7.53 (dd, 1H), 7.44 (d, 1H), 7.46 (bs, 1H), 7.39 (d, 1H), 7.19 (t, 1H), 6.93 (d, 1H), 3.17 (bs, 4H), 2.8-2.5 (bm, 8H), 2.64 (s, 3H), 2.03 (s, 3H).

Example 100

N-(3-{2-[4-(8-Fluoro-2-methyl-5-quinolinyl)-1 piperazinyl]ethyl}phenyl)acetamide (E100)

8-Fluoro-2-Methyl-5-quinolinyl trifluoromethanesulfonate

A solution of 8-fluoro-2-methyl-quinolin-5-ol (WO/2002034754) (103 mg, 0.58 mmol) and pyridine (1 mL) in dichloromethane (4 mL) was cooled to 0° C. and trifluoromethanesulfonic anhydride (144 µL) was added. The reaction mixture was stirred under an inert atmosphere at room temperature for 1 h, then poured into water and extracted into ethyl acetate. The organic layers were combined, dried (sodium sulfate) and concentrated under reduced pressure. The crude was purified by flash chromatography on silica gel, eluting with ethyl acetate-cyclohexane (4:6) affording the title compound (134 mg, 74% yield).

1H-NMR (300 MHz, d$_6$-DMSO) δ(ppm): 8.31 (m, 1H), 7.85 (m, 1H), 7.60 (m, 2H), 2.82 (s, 3H).

4-(8-Fluoro-2-methyl-5-quinolin-5-yl)-piperazine-1-carboxylic acid tert-butyl ester 1,1-Dimethylethyl 1-piperazinecarboxylate (96 mg, 0.52 mmol), cesium carbonate (211 mg, 0.65 mmol), palladium acetate (14 mg, 0.06 mmol) and 2,2'-bis(diphenylphosphino)-1,1'-binaphthyl (80 mg, 0.13 mmol) were added to a solution of 8-fluoro-2-methyl-5-quinolinyl trifluoromethanesulfonate (134 mg, 0.43 mmol) in toluene (1.5 mL) under an inert atmosphere. The reaction mixture was stirred at reflux for 6 hours. The reaction was then cooled to room temperature and quenched using a saturated aqueous solution of ammonium chloride and extracted into ethyl acetate. The organic layers were combined, dried (sodium sulfate) and concentrated under reduced pressure. The crude was purified by flash chromatography on silica gel, eluting with ethyl acetate-cyclohexane (1:9) affording the title compound (50 mg, 34% yield).

MS; (ES) m/z: 346 [MH]$^+$. $C_{19}H_{14}FN_3O_2$ requires 345.

8-Fluoro-2-Methyl-5-piperazin-1-yl-quinoline 4-(8-Fluoro-2-Methyl-5-quinolin-5-yl)-piperazine-1-carboxylic acid tert-butyl ester (50 mg, 0.14 mmol) was dissolved in 1,4-dioxane (0.5 mL) and HCl (2.5 mL of a 4N solution in dioxane) was added under stirring. After stirring for 4 hours, the solvent was evaporated to yield a white solid that was dissolved in water, basified with solid sodium hydroxide (pH>10) and extracted with dichloromethane. The organic layer was dried (sodium sulfate) and then evaporated under reduced pressure to afford the title compound (50 mg, 70% yield).

MS; (ES) m/z: 246 [MH]$^+$. $C_{14}H_{16}FN_3$ requires 245.

8-Fluoro-2-methyl-5-{4-[2-(3-nitrophenyl)ethyl]-1-piperazinyl}quinoline

N,N-Diisopropylethylamine (0.25 mL; 3 eq) was added to a solution of 2-methyl-5-(1-piperazinyl)-8-fluoro quinoline (0.170 g; 1 eq) and 2-(3-nitrophenyl)ethyl methanesulfonate (D4) (0.17 g; 1 eq) in dimethylformamide (4.0 mL). The reaction mixture was heated to 100° C. for 10 hours. The dark solution was cooled to room temperature and concentrated under reduced pressure. The residue was diluted with water (3 mL) and brine (1 mL) and extracted into ethyl acetate (3×3 mL). The combined organic layers were dried over sodium sulfate and concentrated under reduced pressure. The crude was purified by flash chromatography on silica gel, eluting with a gradient from dichloromethane to dichloromethane-methanol (98:2) affording the title compound in 46% yield (0.126 g).

MS; (ES) m/z: 395.5 [MH]$^+$. $C_{22}H_{23}FN_4O_2$ requires 394.

1H-NMR (300 MHz, CDCl$_3$) δ(ppm): 8.38 (d, 1H), 8.10 (s, 1H), 8.05 (m, 1H), 7.56 (m, 1H), 7.50 (t, 1H), 7.35 (m, 2H), 6.95 (m, 1H), 3.15 (m, 4H), 2.95 (m, 2H), 2.80-2.70 (m, 7H), 2.75 (s, 3H).

3-{2-[4-(8-Fluoro-2-methyl-5-quinolinyl)-1-piperazinyl]ethyl}aniline

A solution of 8-fluoro-2-methyl-5-{4-[2-(3-nitrophenyl)ethyl]-1-piperazinyl}quinoline (0.126 g; 1 eq) in methanol (4 mL) was added dropwise to a suspension of iron powder (0.125 g; 7 eq) and ammonium chloride (0.119 g; 7 eq) in water (4 mL). The reactants were heated at reflux for 8 hours, with additional amounts of iron powder (total 0.125 g; 7 eq) and ammonium chloride (0.119 g; 7 eq) added in 3 portions during the reaction. The reaction mixture was cooled to room temperature and filtered using a Millipore filter. The filtrate was concentrated under reduced pressure, diluted with water (5 mL) and a saturated aqueous solution of sodium hydrogen carbonate (2 mL) and extracted into ethyl acetate (3×5 mL). The combined organic extracts were dried over sodium sulfate and concentrated under reduced pressure to give the title compound in 77% yield (0.090 g).

MS; (ES) m/z: 365.3 [MH]$^+$. $C_{22}H_{25}FN_4$ requires 364.

1H-NMR (300 MHz, CDCl$_3$) δ(ppm): 8.36 (d, 1H), 7.31 (m, 1H), 7.05 (t, 1H), 7.00 (m, 1H), 6.70 (m, 1H), 6.55 (m, 2H), 3.70 (bs, 2H), 3.15 (bm, 4H), 2.80-2.70 (m, 7H), 2.75 (s, 3H).

N-(3-{2-[4-(8-Fluoro-2-methyl-5-quinolinyl)-1 piperazinyl]ethyl}phenyl)acetamide (E100)

The title compound was prepared in 26% yield according to the general procedure for the preparation of amides (Method B) starting from 3-{2-[4-(8-fluoro-2-methyl-5-quinolinyl)-1-piperazinyl]ethyl}aniline and acetyl chloride.

MS: (ES) m/z: 407.5 [MH]$^+$. $C_{24}H_{27}FN_4O$ requires 406.

1H-NMR (300 MHz, d$_6$-DMSO) δ(ppm): 10.74 (bs, 1H), 10.00 (s, 1H), 8.46 (dd, 1H), 7.63 (bs, 1H), 7.55 (d, 1H), 7.49 (dd, 1H), 7.39 (d, 1H), 7.23 (t, 1H), 7.18 (dd, 1H), 6.97 (d, 1H), 3.69 (bd, 2H), 3.44 (m, 2H), 3.83 (m, 2H), 3.21 (m, 2H), 3.32 (m, 2H), 3.08 (m, 2H), 2.69 (s, 3H), 2.04 (s, 3H).

Example 101

O-Methyl (2-{2-[4-(2-methyl-5-quinolinyl)-1-piperazinyl]ethyl}phenyl)thiocarbamate dihydrochloride (E101)

The title compound was prepared in 55% yield according to the general procedure for the preparation of carbamates (Method D) starting from 3-{2-[4-(2-methyl-5-quinolinyl)-1-piperazinyl]ethyl}aniline (D6) and phenyl chlorothionoformate. The crude obtained was hydrolysed with 1N aqueous NaOH in THF/MeOH 4:1 and purified according to the general procedure indicated above.

MS: (ES/+) m/z: 421 [MH$^+$] $C_{25}H_{30}N_4O_2$ requires 420.

1H-NMR (400 MHz, d$_6$-DMSO) δ(ppm): 11 (2H, s), 8.90 (1H, bs), 7.94 (2H, bs), 7.81 (1H, bs), 7.43 (1H, m), 7.33 (2H, t), 7.19 (1H, d), 4.0-3.2 (15H, m), 2.96 (3H, s).

Example 102

N-(3-{1-Hydroxy-2-[4-(2-methyl-5-quinolinyl)-1-piperazinyl]ethyl}phenyl)acetamide (E102)

N-(3-{2-[4-(2-methyl-5-quinolinyl)-1-piperazinyl]acetyl}phenyl)acetamide

To a stirred solution of 2-methyl-5-(1-piperazinyl)quinoline (D6, 0.14 g, 1 eq) in dry DMF (5 mL) were added potassium carbonate (0.11 g, 1.2 eq) and a solution of N-[3-(2-chloroacetyl)phenyl]acetamide (J. Chem. Soc., 1949, 552, 553, 0.17 g, 1.2 eq) in DMF (3 mL) under an inert atmosphere. The reaction was stirred for 1.5 hrs. The mixture was diluted with water (8 mL) and extracted with DCM (3×15 mL). The organic phase was washed with brine (25 mL), dried over sodium sulfate and the solvent was removed under reduced pressure. The crude material was purified on SPE cartridge (Silica) using as eluant DCM-methanol (95:5), affording the title compound in 42% yield (0.104 g).

MS; (ES) m/z: 403.2 [MH$^+$]. $C_{24}H_{26}N_4O_2$ requires 402.

1H-NMR (500 MHz, CDCl$_3$) δ(ppm): 8.40 (d, 1H), 8.13 (s, 1H), 7.84 (d, 1H), 7.79 (d, 1H), 7.73 (d, 1H), 7.59 (t, 2H), 7.45 (t, 1H), 7.39 (bs, 1H), 7.27 (d, 1H), 7.09 (d, 1H), 3.95 (s, 2H), 3.18 (t, 4H), 2.91 (bs, 4H), 2.74 (s, 3H), 2.23 (s, 3H).

N-(3-{1-Hydroxy-2-[4-(2-methyl-5-quinolinyl)-1-piperazinyl]ethyl}phenyl)acetamide (E102)

Sodium borohydride (0.015 g, 1.6 eq) was added to a stirred solution of N-(3-{2-[4-(2-methyl-5-quinolinyl)-1-piperazinyl]acetyl}phenyl)acetamide (0.102 g, 1 eq) in dry DCM (2 mL) cooled to 0° C. under an inert atmosphere. The reaction was warmed to room temperature and stirred for 18 hours. The mixture was diluted with DCM (10 mL) and washed with water (2×10 mL). The organic phase was dried over sodium sulfate and the solvent was removed under reduced pressure. The crude material was purified on SPE cartridge (Silica) using as eluant DCM-methanol (97:3), affording the title compound in 42% yield (0.104 g).

MS; (ES) m/z: 405.3 [MH$^+$]. $C_{24}H_{28}N_4O_2$ requires 404.

1H-NMR (500 MHz, CDCl$_3$) δ(ppm): 8.35 (d, 1H), 7.70 (d, 1H), 7.60 (s+d, 2H), 7.40 (d, 1H), 7.30 (t, 1H), 7.30-7.2 (d+s, 2H), 7.20-7.10 (t, 1H), 7.05 (d, 1H), 4.8 (dd, 1H), 3.10 (bs, 4H), 3.0 (bs, 2H), 2.7 (m, 4H), 2.7 (s, 3H), 2.1 (s, 3H).

Example 103

N-(5-Chloro-1,3-benzoxazol-2-yl)-N'-(3-{2-[4-(2-methyl-5-quinolinyl)-1-piperazinyl]ethyl}phenyl)urea (E103)

Triethylamine (6 eq) and then triphosgene (0.5 eq) were added portionwise to a stirred solution of 3-{2-[4-(2-methyl-5-quinolinyl)-1-piperazinyl]ethyl}aniline (D6) (1 eq) in dichloromethane at 0° C. under an inert atmosphere. The reaction was stirred for 1 h. To the mixture were added acetonitrile, diisopropylethylamine (2 eq) and 5-chloro-1,3-benzoxazol-2-amine (1.1 eq). The reaction was stirred for 16 h.

The mixture was extracted with dichloromethane and washed with saturated aqueous sodium hydrogencarbonate solution and brine, dried over sodium sulfate and the solvent was removed under reduced pressure. The crude material was purified by chromatography on SPE cartridge (Silica), using as eluent a gradient from dichloromethane-MeOH 99:1 to dichloromethane-MeOH 98:2, affording the title compound (yield 47%).

1H-NMR (400 MHz, CDCl$_3$) δ(ppm): 8.35 (1H, d), 7.8 (1H, d), 7.6 (1H, t), 7.55 (2H, m), 7.45 (1H, d), 7.35-7.20 (4H, m), 7.15 (1H, d), 7.05 (1H, d), 3.35 (4H, m), 3.2 (4H, m), 3.1 (4H, s), 2.75 (3H, s).

Example 104

(R or S) N-(3-{1-hydroxy-2-[4-(2-methyl-5-quinolinyl)-1-piperazinyl]ethyl}phenyl)-2,4-dimethyl-1,3-thiazole-5-carboxamide dihydrochloride (E104)

Racemic N-(3-{1-hydroxy-2-[4-(2-methyl-5-quinolinyl)-1-piperazinyl]ethyl}phenyl)-2,4-dimethyl-1,3-thiazole-5-carboxamide (E40) was separated preparative chiral HPLC using a Daicel Chiralcel OJ column and a mixture of n-hexane and ethanol (75:25) as eluent to afford the title compound as the first-eluting enantiomer.

MS: (ES/+) m/z: 502 [MH$^+$]. $C_{28}H_{31}N_5O_2S$ requires 501.65.

1H-NMR (400 MHz, d$_6$-DMSO) δ(ppm): 10.18 (2H, br s), 8.85 (1H, br s), 7.89 (3H, s), 7.77 (1H, br s), 7.53 (1H, d), 7.37 (2H, m), 7.18 (1H, d), 6.36 (1H, br s), 5.17 (1H, dd), 3.80-3.20 (10H, m), 2.85 (3H, s), 2.64 (3H, s), 2.53 (3H, s).

Example 105

(S or R) N-(3-{1-hydroxy-2-[4-(2-methyl-5-quinolinyl)-1-piperazinyl]ethyl}phenyl)-2,4-dimethyl-1,3-thiazole-5-carboxamide dihydrochloride (E105)

Racemic N-(3-{1-hydroxy-2-[4-(2-methyl-5-quinolinyl)-1-piperazinyl]ethyl}phenyl)-2,4-dimethyl-1,3-thiazole-5-carboxamide was separated using preparative chiral HPLC using a Daicel Chiralcel OJ column and a mixture of n-hexane and ethanol (75:25) as eluent to afford the title compound as the second-eluting enantiomer.

MS: (ES/+) m/z: 502 [MH$^+$]. $C_{28}H_{31}N_5O_2S$ requires 501.65.

1H-NMR (400 MHz, d$_6$-DMSO) δ(ppm): 10.18 (2H, br s), 8.85 (1H, br s), 7.89 (3H, s), 7.77 (1H, br s), 7.53 (1H, d), 7.37 (2H, m), 7.18 (1H, d), 6.36 (1H, br s), 5.17 (1H, dd), 3.80-3.20 (10H, m), 2.85 (3H, s), 2.64 (3H, s), 2.53 (3H, s).

General Procedure for the Preparation of Imides Starting from 3-{2-[4-(2-methyl-5-quinolinyl)-1-piperazinyl]ethyl}aniline (D6): Method I A solution of 3-{2-[4-(2-methyl-5-quinolinyl)-1-piperazinyl]aniline (D6), the phthalic anhydride (2 eq) in dry pyridine and dry toluene (2/3 ratio) was heated in a microwave apparatus at 160° C. for 20 minutes under an inert atmosphere. The mixture was then cooled to room temperature, diluted with DCM and washed with saturated aqueous ammonium chloride solution, dried over sodium sulfate and the solvent was removed under reduced pressure. The crude material was purified by chromatography, using a SPE cartridge (Silica) and gradient elution from dichloromethane/MeOH 99/1 to dichloromethane-MeOH 95:5, affording the final compounds (yields ranged from 55 to 94%).

Example 106

2-(3-{2-[4-(2-methyl-5-quinolinyl)-1-piperazinyl]ethyl}phenyl)-1H-isoindole-1,3(2H)-dione (E106)

Prepared from 3-{2-[4-(2-methyl-5-quinolinyl)-1-piperazinyl]ethyl}aniline (D6) and 2-benzofuran-1,3-dione according to Method I.

MS; (ES) m/z: 477.3 [MH]+. $C_{30}H_{28}N_4O_2$ requires 476.

1H-NMR (300 MHz, CDCl$_3$) δ(ppm): 8.37 (d, 1H), 7.94 (m, 2H), 7.79 (m, 2H), 7.70 (d, 1H), 7.56 (t, 1H), 7.43 (t, 1H), 7.31-7.22 (m, 4H), 7.06 (d, 1H), 3.10 (m, 4H), 2.90 (m, 2H), 2.80 (m, 6H), 2.70 (s, 3H).

Example 107

2-(3-{2-[4-(2-methyl-5-quinolinyl)-1-piperazinyl]ethyl}phenyl)-2,3-dihydro-1H-isoindol-1-one (E107)

A solution of trimethylaluminium (2.0 M in hexane, 1 eq) was added slowly to a stirred solution of 3-{2-[4-(2-methyl-5-quinolinyl)-1-piperazinyl]ethyl}aniline (D6, 1 eq) in dichloromethane (0.1 M) at 0° C. The reaction mixture was stirred for 15 min then a solution of phthalide (1 eq) in dichloromethane was added dropwise. The solution was stirred for 2 h at 0° C. then partitioned between saturated aqueous ammonium chloride solution and ethyl acetate. The organic phase was dried over sodium sulfate and the solution was concentrated under reduced pressure. The crude 2-(hydroxymethyl)-N-(3-{2-[4-(2-methyl-5-quinolinyl)-1-piperazinyl]ethyl}phenyl)benzamide was dissolved in dichloromethane then N,N-diisopropylethylamine (1 eq.) and methanesulfonyl chloride (1 eq.) were added successively. The reaction mixture was stirred for 2 hours at room temperature then partitioned between saturated aqueous ammonium chloride solution and dichloromethane. The organic phase was dried over sodium sulfate and concentrated under reduced pressure. The residue was purified by chromatography (SPE cartridge, Silica) eluting with a gradient from dichloromethane-methanol (100:2) to (98:2) affording the title compound (yield 45%).

MS; (ES) m/z: 463.3 [MH]+. $C_{30}H_{30}N_4O$ requires 462.

1H-NMR (400 MHz, CDCl$_3$) δ(ppm): 8.41 (d, 1H), 8.01 (d, 1H), 7.73 (d, 1H), 7.62-7.48 (m, 3H), 7.44 (d, 1H), 7.34-7.22 (m, 2H), 7.17 (m, 2H), 7.09 (d, 1H), 7.02 (d, 1H), 5.42 (s, 2H), 3.17 (t, 4H), 2.94-2.74 (m, 8H), 2.74 (s, 3H).

Example 108

4-fluoro-2-(3-{2-[4-(2-methyl-5-quinolinyl)-1-piperazinyl]ethyl}phenyl)-1H-isoindole-1,3(2H)-dione (E108)

Prepared from 3-{2-[4-(2-methyl-5-quinolinyl)-1-piperazinyl]ethyl}aniline (D6) and 4-fluoro-2-benzofuran-1,3-dione according to Method I.

MS; (ES) m/z: 495.3 [MH]+. $C_{30}H_{27}FN_4O_2$ requires 494.

1H-NMR (400 MHz, CDCl$_3$) δ(ppm): 8.42 (d, 1H), 7.84-7.82 (m, 2H), 7.75 (d, 1H), 7.62 (t, 1H), 7.51-7.47 (m, 2H), 7.35-7.28 (m, 4H), 7.12 (d, 1H), 3.19 (bs, 4H), 3.10-2.70 (m, 8H), 2.76 (s, 3H).

Example 109

5,6-dichloro-2-(3-{2-[4-(2-methyl-5-quinolinyl)-1-piperazinyl]ethyl}phenyl)-1H-isoindole-1,3(2H)-dione Prepared from 3-{2-[4-(2-methyl-5-quinolinyl)-1-piperazinyl]ethyl}aniline (D6) and 5,6-dichloro-2-benzofuran-1,3-dione according to Method I.

MS; (ES) m/z: 545.2 [MH]+. $C_{30}H_{26}Cl_2N_4O_2$ requires 544.

1H-NMR (400 MHz, CDCl$_3$) δ(ppm): 8.42 (d, 1H), 8.07 (s, 2H), 7.75 (d, 1H), 7.62 (t, 1H), 7.49 (t, 1H), 7.36-7.28 (m, 4H), 7.11 (d, 1H), 3.18 (bs, 4H), 3.10-2.70 (m, 6H), 2.99 (t, 2H), 2.76 (s, 3H).

Example 110

5-methyl-2-(3-{2-[4-(2-methyl-5-quinolinyl)-1-piperazinyl]ethyl}phenyl)-1H-isoindole-1,3(2H)-dione (E110)

Prepared from 3-{2-[4-(2-methyl-5-quinolinyl)-1-piperazinyl]ethyl}aniline (D6) and 5-methyl-2-benzofuran-1,3-dione according to Method I.

MS; (ES) m/z: 491.3 [MH]+. $C_{31}H_{30}N_4O_2$ requires 490.

1H-NMR (400 MHz, CDCl$_3$) δ(ppm): 8.42 (d, 1H), 7.87 (d, 1H), 7.79 (s, 1H), 7.76 (d, 1H), 7.64-7.60 (m, 2H), 7.48 (t, 1H), 7.35-7.29 (m, 4H), 7.13 (d, 1H), 3.21 (bs, 4H), 3.10-2.80 (m, 8H), 2.77 (s, 3H), 2.59 (s, 3H).

Example 111

4-(Methoxy)-N-(3-{2-[4-(2-methyl-5-quinolinyl)-1-piperazinyl]propyl}phenyl)benzamide (E111)

5-{4-[2-(3-bromophenyl)propyl]-1-piperazinyl}-2-methylquinoline (D20)

A solution of zinc(II) chloride (0.5 M, THF, 0.5 eq., 234 uL) was added to a stirred solution of 1-(3-bromophenyl)-2-propanone (50 mg) and 2-methyl-5-(1-piperazinyl)quinoline (D3) (2.0 eq., 107 mg) in methanol (1 ml). The mixture was stirred 10 minutes then a solution of sodium cyanoborohydride (1M, THF, 1.0 eq., 234 uL) was added. The resulting white mixture was stirred at room temperature until hplc showed the complete disappearance of starting material. The mixture was concentrated under reduced pressure, diluted with aqueous sodium hydroxide solution (1M), and extracted with DCM. The combined organic phases were washed with brine, dried over sodium sulfate and concentrated. The crude was purified by chromatography using a SPE cartridge (SiO$_2$) with DCM-methanol (98:2) as eluent to afford the title compound (50 mg, 50% yield).

MS: (ES/+) m/z: 424, 426 [MH$^+$]. C$_{23}$H$_{26}$BrN$_3$ requires 423, 425.

1H-NMR (300 MHz, CDCl$_3$) δ(ppm): 8.30 (d, 1H), 7.80 (d, 1H), 7.70 (t, 1H), 7.50-7.30 (m, 6H), 3.25-2.95 (m, 10H), 2.80 (s, 3H), 2.55 (m, 1H), 1.15 (d, 3H).

4-(Methoxy)-N-(3-{2-[4-(2-methyl-5-quinolinyl)-1-piperazinyl]propyl}phenyl)benzamide (E111)

The title compound was prepared in 21% yield according to the general procedure for the preparation of amides, ureas and carbamates (Method A) starting from 5-{4-[2-(3-bromophenyl)propyl]-1-piperazinyl}-2-methylquinoline (D20) and 4-methoxybenzamide.

MS: (ES/+) m/z: 495 [MH$^+$]. C$_{31}$H$_{34}$N$_4$O$_2$ requires 494.

1H-NMR (400 MHz, DMSO) δ(ppm): 10.63 (br s, 1H), 10.16 (s, 1H), 8.91 (br s, 1H), 7.99 (d, 2H), 7.86 (m, 3H), 7.74 (br s, 1H), 7.61 (d, 1H), 7.41 (br s, 1H), 7.37 (t, 1H), 7.08 (d, 3H), 3.86 (s, 3H), 3.66 (br s, 4H), 3.80-2.70 (m, 10H), 1.28 (d, 3H).

Example 112

2-Fluoro-N-(3-{2-[4-(2-methyl-5-quinolinyl)-1-piperazinyl]propyl}phenyl)benzamide (E112)

The title compound was prepared in 40% yield according to the general procedure for the preparation of amides, ureas and carbamates (Method A) starting from 5-{4-[2-(3-bromophenyl)propyl]-1-piperazinyl}-2-methylquinoline (D20) and 2-fluorobenzamide.

MS: (ES/+) m/z: 483 [MH$^+$]. C$_{30}$H$_{31}$FN$_4$O requires 482.

1H-NMR (400 MHz, d$_6$-DMSO) δ(ppm): 10.85 (br s, 1H), 10.48 (s, 1H), 8.97 (br s, 1H), 7.92 (br s, 2H), 7.83 (s, 1H), 7.78 (br s, 1H), 7.68 (td, 1H), 7.61 (qd, 1H), 7.55 (d, 1H), 7.43 (br s, 1H), 7.40-7.34 (m, 3H), 7.11 (d, 1H), 4.0-2.7 (m, 11H), 2.88 (s, 3H), 1.28 (d, 3H).

Example 113

3-Fluoro-N-(3-{2-[4-(2-methyl-5-quinolinyl)-1-piperazinyl]propyl}phenyl)benzamide (E113)

The title compound was prepared in 55% yield according to the general procedure for the preparation of amides, ureas and carbamates (Method A) starting from 5-{4-[2-(3-bromophenyl)propyl]-1-piperazinyl}-2-methylquinoline (D20) and 3-fluorobenzamide.

MS: (ES/+) m/z: 483 [MH$^+$]. C$_{30}$H$_{31}$FN$_4$O requires 482.

1H-NMR (400 MHz, d$_6$-DMSO) δ(ppm): 10.39 (s, 1H), 10.30 (br s, 1H), 8.77 (br s, 1H), 7.90-7.82 (m, 5H), 7.70-7.52 (m, 3H), 7.48 (td, 1H), 7.40-7.35 (m, 2H), 7.12 (d, 1H), 3.8-2.7 (m, 14H), 1.28 (d, 3H).

Example 114

3-(Methoxy)-N-(3-{2-[4-(2-methyl-5-quinolinyl)-1-piperazinyl]propyl}phenyl)benzamide (E114)

The title compound was prepared in 35% yield according to the general procedure for the preparation of the amides, ureas and carbamates (Method A) starting from 5-{4-[2-(3-bromophenyl)propyl]-1-piperazinyl}-2-methylquinoline (D20) and 3-methoxybenzamide.

MS: (ES/+) m/z: 495 [MH$^+$]. C$_{31}$H$_{34}$N$_4$O$_2$ requires 494.

1H-NMR (400 MHz, d$_6$-DMSO) δ(ppm): 10.7 (br s, 1H), 10.29 (s, 1H), 8.90 (Br s, 1H), 7.89 (br s, 2H), 7.86 (s, 1H), 7.75 (br s, 1H), 7.62 (d, 1H), 7.57 (d, 1H), 7.51 (t, 1H), 7.45 (br s, 1H), 7.38 (t, 1H), 7.19 (dd, 1H), 7.11 (dd, 1H), 3.86 (s, 3H), 3.75 (m, 1H), 3.66-2.86 (m, 14H), 2.78 (t, 1H), 1.28 (d, 3H).

Example 115

N-(3-{2-[4-(2-methyl-5-quinolinyl)-1-piperazinyl]propyl}phenyl)acetamide (E115)

The title compound was prepared in 64% yield according to the general procedure for the preparation of the amides, ureas and carbamates (Method A) starting from 5-{4-[2-(3-bromophenyl)propyl]-1-piperazinyl}-2-methylquinoline (D20) and acetamide.

MS: (ES/+) m/z: 403 [MH$^+$]. C$_{25}$H$_{30}$N$_4$O requires 402.

1H-NMR (400 MHz, d$_6$-DMSO) δ(ppm): 10.74 (br s, 1H), 10.01 (s, 1H), 8.93 (br s, 1H), 7.90 (br s, 2H), 7.76 (br s, 1H), 7.65 (s, 1H), 7.41 (br d, 2H), 7.31 (t, 1H), 7.02 (d, 1H), 3.80-2.73 (m, 11H), 2.87 (s, 3H), 2.06 (s, 3H), 1.24 (d, 3H).

Example 116

1-(3-{2-[4-(2-methyl-5-quinolinyl)-1-piperazinyl]propyl}phenyl)-3-phenyl-2-imidazolidinone (E116)

The title compound was prepared in 55% yield according to the general procedure for the preparation of the amides, ureas and carbamates (Method A) starting from 5-{4-[2-(3-bromophenyl)propyl]-1-piperazinyl}-2-methylquinoline (D20) and 1-phenyl-2-imidazolidinone.

MS: (ES/+) m/z: 506 [MH$^+$]. C$_{32}$H$_{35}$N$_5$O requires 505.

1H-NMR (400 MHz, DMSO) δ(ppm): 10.4 (br s, 1H), 8.80 (br s, 1H), 7.83 (br s, 2H), 7.71 (s, 1H), 7.66 (d, 1H), 7.70-7.60 (m, 1H), 7.51 (br d, 1H), 7.40 (m, 4H), 7.10-7.05 (m, 2H), 4.01 (br s, 4H), 3.78 (br m, 1H), 3.66 (br m, 4H), 3.5 (br m, 5H), 2.87 (br m, 4H), 1.24 (d, 3H).

Example 117

3-(3-{2-[4-(2-methyl-5-quinolinyl)-1-piperazinyl]propyl}phenyl)-1,3-oxazolidin-2-one (E117)

The title compound was prepared in 73% yield according to the general procedure for the preparation of the amides, ureas and carbamates (Method A) starting from 5-{4-[2-(3-bromophenyl)propyl]-1-piperazinyl}-2-methylquinoline (D20) and 2-oxazolidone. MS: (ES/+) m/z: 431 [MH$^+$]. C$_{26}$H$_{30}$N$_4$O$_2$ requires 430.

1H-NMR (400 MHz, d$_6$-DMSO) δ(ppm): 10.6 (br s, 1H), 8.90 (br s, 1H), 7.87 (br s, 2H), 7.73 (s, 1H), 7.61 (s, 1H), 7.46 (d, 1H), 7.42 (t, 1H), 7.40 (br s, 1H), 7.12 (d, 1H), 4.47 (t, 2H), 4.10 (2H), 3.77 (br m, 1H), 3.65 (br s, 4H), 3.50-3.40 (br m, 5H), 2.84 (br s, 4H), 2.80 (m, 1H), 1.25 (d, 3H).

Example 118

N-(3-{1-methyl-2-[4-(2-methyl-5-quinolinyl)-1-piperazinyl]ethyl}phenyl)acetamide (E118)

Methyl (3-nitrophenyl)acetate

Trimethylsilyl chloride (5.6 mL, 2.0 equiv.) was added to a stirred solution of (3-nitrophenyl)acetic acid (4.0 g) in methanol (60 ml). The resulting solution was stirred at room temperature for 18 hours, then concentrated at reduced pressure and partitioned between DCM and aqueous sodium hydrogencarbonate solution. The organic phase was dried over sodium sulfate, filtered and concentrated under vacuum to give the title compound as a colourless liquid (4.2 g, 100%).

1H-NMR (300 MHz, CDCl$_3$) δ(ppm): 8.15 (s, 1H), 8.07 (d, 1H), 7.60 (d, 1H), 7.47 (t, 1H), 3.85 (s, 2H), 3.80 (s, 3H).

Methyl 2-(3-nitrophenyl)propanoate

A solution of lithium hexamethyldisilazide (1M, hexane, 1.0 eq., 21.5 ml) was added dropwise to a stirred solution of methyl (3-nitrophenyl)acetate (4.2 g) in THF (30 ml) at −30 C. The mixture was warmed to 0 C and re-cooled to −30 C then iodomethane (1.0 equiv., 3.0 g.) was added. The solution was warmed to room temperature and poured into aqueous ammonium chloride solution and extracted with ethyl acetate. The combined organic phases were washed with brine, dried over sodium sulfate and concentrated. The crude was purified using chromatography (SiO$_2$, SPE) using cyclohexane/ethyl acetate (80/20) as eluent to afford the title compound as yellow liquid (1.50 g, 30% yield).

1H-NMR (300 MHz, CDCl$_3$) δ(ppm): 8.15 (s, 1H), 8.10 (d, 1H), 7.60 (d, 1H), 7.45 (t, 1H), 3.85 (q, 1H), 3.65 (s, 3H), 1.50 (d, 3H).

(3-Nitrophenyl)-1-propanol

A solution of lithium borohydride (2M, THF, 2.0 equiv. 3.4 ml) was added to a solution of methyl 2-(3-nitrophenyl)propanoate (0.7 g) in THF. The resulting mixture was stirred for 18 hours then concentrated and poured into hydrochloric acid (10%) at 0 C. The mixture was extracted with ether. The combined organic phases were dried over sodium sulfate, filtered and concentrated to afford the title compound as yellow oil (0.610 g, 100% yield).

1H-NMR (300 MHz, CDCl$_3$) δ(ppm): 8.10 (s, 1H), 8.05 (d, 1H), 7.60 (d, 1H), 7.45 (t, 1H), 3.75 (d, 2H), 3.05 (sext, 1H), 1.30 (d, 3H).

2-(3-Nitrophenyl)propanal

To a stirred suspension of 1,1,1-tris(acetyloxy)-1,1-dihydro-1,2-benziodoxol-3(1H)-one (Dess-Martin periodinane, 1.1 eq., 1.52 g) in DCM (4 mL) was added 2-(3-nitrophenyl)-1-propanol (0.610 g). The resulting solution was stirred for 1 h then poured into water and extracted with DCM. The combined organic phases were washed with aqueous sodium hydrogencarbonate solution and brine, dried over sodium sulfate then concentrated to afford a brown solid (1.4 g). This solid was dissolved in ether and filtered. The filtrate was concentrated under vacuum to give the title compound as yellow liquid (0.57 g, 94% yield).

1H-NMR (300 MHz, CDCl$_3$) δ(ppm): 9.70 (s, 1H), 8.15 (d, 2H), 8.10 (s, 1H), 7.6 (m, 2H), 3.75 (q, 1H), 1.50 (d, 3H).

2-Methyl-5-{4-[2-(3-nitrophenyl)propyl]-1-piperazinyl}quinoline

A mixture of 2-(3-nitrophenyl)propanal (1.2 equiv. 50 mg), 2-methyl-5-(1-piperazinyl)quinoline (D3) (52 mg) and DCM (2 mL) was stirred for 1 h. Sodium triacetoxyborohydride (1.2 equiv., 58 mg) was added and the resulting mixture was stirred for 18 h. The reaction mixture was concentrated in vacuo and purified using ion-exchange chromatography (SCX-2), eluting with methanol followed by ammonia in methanol (1M). The basic fractions were concentrated under vacuum and purified by chromatography (SPE, SiO$_2$) using DCM-methanol (98:2) as eluent to afford the title compound as yellow liquid (78 mg, 78% yield).

MS; (ES) m/z: 391 [MH]$^+$. C$_{23}$H$_{26}$N$_4$O$_2$ requires 390.

1H-NMR (300 MHz, CDCl$_3$) δ(ppm): 8.35 (d, 1H), 8.15 (br s, 1H), 8.05 (d, 1H), 7.68 (d, 1H), 7.55 (m, 2H), 7.45 (t, 1H), 7.22 (d, 1H), 7.05 (d, 1H), 3.25-3.00 (m, 5H), 2.75-2.50 (m, 9H), 1.30 (d, 3H).

3-{1-Methyl-2-[4-(2-methyl-5-quinolinyl)-1-piperazinyl]ethyl}aniline (D21)

A solution of 2-methyl-5-{4-[2-(3-nitrophenyl)propyl]-1-piperazinyl}quinoline (70 mg) in methanol (1 mL) was added dropwise to a stirred suspension of iron powder (3.0 equiv., 30 mg) and ammonium chloride (5.0 equiv., 48 mg) in water (1 mL). The reactants were heated at reflux for 18 hours. The reaction mixture was cooled to room temperature then filtered using a Millipore filter. The filtrate was concentrated under reduced pressure and purified using chromatography (SiO$_2$, SPE) eluting with DCM-methanol (95:5) to afford the title compound (40 mg, 60% yield).

MS; (ES) m/z: 361 [MH]$^+$. C$_{23}$H$_{28}$N$_4$ requires 360.

1H-NMR (300 MHz, CDCl$_3$) δ(ppm): 8.30 (d, 1H), 87.70 (d, 1H), 7.55 (t, 1H), 7.68 (d, 1H), 7.25-7.00 (m, 2H), 6.60-6.50 (m, 3H), 3.10-2.50 (m, 14H), 1.30 (d, 3H).

N-(3-{1-Methyl-2-[4-(2-methyl-5-quinolinyl)-1-piperazinyl]ethyl}phenyl)acetamide (E118)

The title compound was prepared in 75% yield according to the general procedure for the preparation of amides (Method C) starting from 3-{1-methyl-2-[4-(2-methyl-5-quinolinyl)-1-piperazinyl]ethyl}aniline (D21) and acetic acid.

MS: (ES/+) m/z: 403 [MH$^+$]. C$_{26}$H$_{30}$N$_6$O$_2$ requires 402.

1H-NMR (400 MHz, d$_6$-DMSO) δ(ppm): 10.18 (bs, 1H), 10.02 (bs, 1H), 8.78 (bs, 1H), 7.88 (bs, 2H), 7.74 (bs, 1H), 7.67 (s. 1H), 7.44 (d, 1H), 7.38 (bs, 1H), 7.32 (t, 1H), 7.09 (d, 1H), 3.70-3.20 (m, 1H), 2.85 (bs, 3H), 2.06 (s, 3H), 1.35 (d, 3H).

Example 119

2-Fluoro-N-(3-{1-methyl-2-[4-(2-methyl-5-quinolinyl)-1-piperazinyl]ethyl}phenyl)benzamide (E119)

The title compound was prepared in 64% yield according to the general procedure for the preparation of amides (Method C) starting from 3-{1-methyl-2-[4-(2-methyl-5-quinolinyl)-1-piperazinyl]ethyl}aniline (D21) and 2-fluorobenzoic acid.

MS: (ES/+) m/z: 483 [MH$^+$]. C$_{30}$H$_{31}$FN$_4$O requires 482.

1H-NMR (400 MHz, d$_6$-DMSO) δ(ppm): 10.48 (s, 1H), 10.08 (bs, 1H), 8.76 (bs, 1H), 7.87 (bs, 3H), 7.72 (bs, 1H), 7.70-7.50 (m, 3H), 7.40-7.20 (m, 5H), 3.70-3.20 (br m, 10H), 2.84 (br s, 3H), 1.39 (d, 3H).

Example 120

2,4-Dimethyl-N-(3-{1-methyl-2-[4-(2-methyl-5-quinolinyl)-1-piperazinyl]ethyl}phenyl)-1,3-thiazole-5-carboxamide (E120)

The title compound was prepared in 87% yield according to the general procedure for the preparation of amides (Method C) starting from 3-{1-methyl-2-[4-(2-methyl-5-quinolinyl)-1-piperazinyl]ethyl}aniline (D21) and 2,4-dimethyl-1,3-thiazole-5-carboxylic acid.

MS: (ES/+) m/z: 501 [MH$^+$]. $C_{29}H_{33}N_5OS$ requires 500.

1H-NMR (400 MHz, DMSO) δ(ppm): 10.63 (br s, 1H), 10.16 (s, 1H), 8.97 (br d, 1H), 8.01 (m, 2H), 7.87 (d, 1H), 7.77 (s, 1H), 7.54 (d, 1H), 7.46 (d, 1H), 7.37 (t, 1H), 7.18 (d, 1H), 3.5 (m, 11H), 2.95 (s, 3H), 2.68 (s, 3H), 2.56 (s, 3H), 1.39 (d, 3H).

Example 121

7-Fluoro-2-(3-{2-[4-(2-methyl-5-quinolinyl)-1-piperazinyl]ethyl}phenyl)-2,3-dihydro-1H-isoindol-1-one A solution of trimethylaluminium (2.0 M in hexane, 1 eq) was added slowly to a stirred solution of 3-{2-[4-(2-methyl-5-quinolinyl)-1-piperazinyl]ethyl}aniline (D6) (1 eq) in dichloromethane (0.1 M) at 0° C. The reaction mixture was stirred for 15 min then a solution of 7-fluoro-2-benzofuran-1(3H)-one (1 eq, Chem. Pharm. Bull., 1985, 33(7), 2809-2820) in DCM was added dropwise. The solution was stirred for 2 h at 0° C. then partitioned between saturated aqueous ammonium chloride solution and ethyl acetate. The organic phase was dried over sodium sulfate and concentrated under reduced pressure. The crude 2-fluoro-6-(hydroxymethyl)-N-(3-{2-[4-(2-methyl-5-quinolinyl)-1-piperazinyl]ethyl}phenyl)benzamide was dissolved in DCM and to 0° C. To the stirred solution was added dropwise thionyl chloride (1 eq.). The reaction mixture was warmed to room temperature, stirred for 1 hour then partitioned between saturated aqueous sodium hydrogencarbonate solution and DCM. The organic phase was dried over sodium sulfate, filtered and the solvent removed under reduced pressure. The crude 2-(chloromethyl)-6-fluoro-N-(3-{2-[4-(2-methyl-5-quinolinyl)-1-piperazinyl]ethyl}phenyl)benzamide thus obtained was dissolved in methanol and cooled to 0° C. To the stirred solution was added sodium methoxide (1.2 eq.) portionwise. The solution was warmed to room temperature and stirred for 18 hours. The solution was concentrated and partitioned between water and dichloromethane. The organic phase was dried over sodium sulfate, filtered and concentrated under reduced pressure. The residue was purified by chromatography on SPE cartridge (Silica) eluting with DCM-methanol (96:4) affording the title compound (yield 24%).

The free base could be converted into its dihydrochloride salt by dissolving the compound in dichloromethane and adding a 1M ethereal solution of HCl (2.1 eq) dropwise. A yellow solid precipitated and the suspension was stirred for 15 min. The solvent was removed under reduced pressure affording a crude material which was triturated with ether. The final compound was then recovered by filtration (yield quantitative).

MS; (ES) m/z: 481.3 [MH]$^+$. $C_{30}H_{29}FN_4O$ requires 480.

1H-NMR (400 MHz, d$_6$-DMSO) δ(ppm): 10.4 (vbs, 1H), 8.60 (vbs, 1H), 7.95 (s, 1H), 7.79-7.72 (m, 4H), 7.60 (vbs, 1H), 7.53-7.46 (d+t, 2H), 7.34 (t+vbs, 2H), 7.18 (d, 1H), 5.08 (s, 2H), 3.80-3.10 (m, 12H), 2.77 (s, 3H).

Example 122

(R or S) 3-(3-{2-[4-(2-Methyl-5-quinolinyl)-1-piperazinyl]propyl}phenyl)-1,3-oxazolidin-2-one (E122)

3-(3-{2-[4-(2-Methyl-5-quinolinyl)-1-piperazinyl]propyl}phenyl)-1,3-oxazolidin-2-one (E 118) was separated using preparative chiral HPLC [Daicel Chiralcel OD column; n-hexane-ethanol (55:45)] to afford the title compound as the first-eluting enantiomer.

(ES/+) m/z: 431 [MH$^+$]. $C_{26}H_{30}N_4O_2$ requires 430.

1H-NMR (400 MHz, d$_6$-DMSO) δ(ppm): 10.6 (br s, 1H), 8.90 (br s, 1H), 7.87 (br s, 2H), 7.73 (s, 1H), 7.61 (s, 1H), 7.46 (d, 1H), 7.42 (t, 1H), 7.40 (br s, 1H), 7.12 (d, 1H), 4.47 (t, 2H), 4.10 (2H), 3.77 (br m, 1H), 3.65 (br s, 4H), 3.50-3.40 (br m, 5H), 2.84 (br s, 4H), 2.80 (m, 1H), 1.25 (d, 3H).

Example 123

(S or R) 3-(3-{2-[4-(2-Methyl-5-quinolinyl)-1-piperazinyl]propyl}phenyl)-1,3-oxazolidin-2-one (E123)

3-(3-{2-[4-(2-Methyl-5-quinolinyl)-1-piperazinyl]propyl}phenyl)-1,3-oxazolidin-2-one (E 118) was separated using preparative chiral HPLC [Daicel Chiralcel OD column; n-hexane-ethanol (55:45)] to afford the title compound as the second-eluting enantiomer.

(ES/+) m/z: 431 [MH$^+$]. $C_{26}H_{30}N_4O_2$ requires 430.

1H-NMR (400 MHz, d$_6$-DMSO) δ(ppm): 10.6 (br s, 1H), 8.90 (br s, 1H), 7.87 (br s, 2H), 7.73 (s, 1H), 7.61 (s, 1H), 7.46 (d, 1H), 7.42 (t, 1H), 7.40 (br s, 1H), 7.12 (d, 1H), 4.47 (t, 2H), 4.10 (2H), 3.77 (br m, 1H), 3.65 (br s, 4H), 3.50-3.40 (br m, 5H), 2.84 (br s, 4H), 2.80 (m, 1H), 1.25 (d, 3H).

Example 124

1-(3-{2-[(2R)-2-methyl-4-(2-methyl-5-quinolinyl)-1-piperazinyl]ethyl}phenyl)-2-imidazolidinone dihydrochloride (E124)

2-Methyl-5-[(3R)-3-methyl-1-piperazinyl]quinoline (2R)-2-Methylpiperazine (0.550 g; 2 eq), caesium carbonate (1.78 g; 2 eq), palladium acetate (0.123 g; 0.2 eq) and 2,2'-bis(diphenylphosphino)-1,1'-binaphthyl (0.513 g; 0.3 eq) were added to a solution of 2-methyl-5-quinolinyl trifluoromethanesulfonate (D1) (0.8 g; 1 eq) in toluene (30 mL) under an inert atmosphere. The reaction mixture was stirred at reflux under nitrogen for 3 hours. The reaction cooled to room temperature, quenched using saturated aqueous ammonium chloride solution (15 mL) and extracted with ethyl acetate (3×20 mL). The organic layers were combined, dried over sodium sulfate and concentrated under reduced pressure. The crude was purified by flash chromatography on silica gel, eluting with dichloromethane-methanol (95:5) affording the title compound in 58% yield (0.383 g).

MS; (ES) m/z: 242.3 [MH]$^+$. $C_{15}H_{19}N_3$ requires 241.

$^1$H-NMR (300 MHz, CDCl$_3$) δ(ppm): 8.40 (d, 1H), 7.76 (d, 1H), 7.61 (t, 1H), 7.29 (d, 1H), 7.06 (d, 1H), 3.2 (m, 5H), 2.85 (t, 1H), 2.74 (s, 3H), 2.5 (t, 1H) 1.25 (d, 3H).

1-(3-{2-[(2R)-2-methyl-4-(2-methyl-5-quinolinyl)-1-piperazinyl]ethyl}phenyl)-2-imidazolidinone dihydrochloride (E124)

A mixture of N,N-diisopropylethylamine (0.072 mL; 2 eq), 2-methyl-5-[(3R)-3-methyl-1-piperazinyl]quinoline (0.05 g; 1 eq), 2-[3-(2-oxo-1-imidazolidinyl)phenyl]ethyl methanesulfonate (0.07 g; 1.2 eq) and acetonitrile (0.5 mL) was irradiated in a microwave reactor (PersonalChemistry Emrys™ Optimiser, 300 W, 180° C., 15 min). The dark solution was loaded on SCX ion-exchange cartridge (5 g) and eluted with methanol followed by a solution of ammonia in methanol (1M). The basic fractions were concentrated under reduced pressure and further purified by flash chromatography on silica gel, eluting with a gradient from dichloromethane to dichloromethane-methanol (98:2) affording the desired free base intermediate in 67% yield. The related dihydrochloride salt was formed according to the description given in the general procedure for the preparation of amides and their corresponding dihydrochloride salts starting from 3-{2-[4-(2-methyl-5-quinolinyl)-1-piperazinyl]ethyl}aniline (D6) to give the title compound in 57% yield (0.03 g).

MS; (ES) m/z: 430.4 [MH]$^+$. $C_{26}H_{31}N_5O$ requires 429.

$^1$H-NMR (500 MHz, DMSO) δ(ppm): 10.8-10.66 (2bs, 1H); 8.54 (bs, 1H); 7.72 (bs, 1H); 7.61 (s, 1H); 7.49 (m, 2H); 7.41 (t, 1H); 7.26 (m, 1H); 7.14 (m, 1H); 3.8 (t, 3H); 3.2 (t, 5H); 3.15/2.65 (bd-m, 7H); 2.5 (s, 3H); 1.3 (d, 3H).

Example 125

3-(3-{2-[(2R)-2-Methyl-4-(2-methyl-5-quinolinyl)-1-piperazinyl]ethyl}phenyl)-1,3-oxazolidin-2-one (E125)

3-[3-(2-Hydroxyethyl)phenyl]-1,3-oxazolidin-2-one

The title compound was prepared in 48% yield according to the general procedure for the preparation of amides, ureas and carbamates (Method A) starting from 2-(3-bromophenyl)ethanol and 1,3-oxazolidin-2-one.

MS: (ES) m/z: 208 [MH$^+$]. $C_{11}H_{13}NO_3$ requires 207.

1H-NMR (300 MHz, CDCl$_3$) δ(ppm): 7.45 (s, 1H), 7.32 (m, 2H), 7.03 (d, 1H), 4.48 (t, 2H), 4.05 (t, 2H), 3.85 (bm, 2H), 2.87 (t, 2H), 1.58 (s, 1H).

2-[3-(2-Oxo-1,3-oxazolidin-3-yl)phenyl]ethyl methanesulfonate

The title compound was prepared in 93% yield according to the general procedure for the preparation of amides (Method B) starting from starting from 3-[3-(2-hydroxyethyl)phenyl]-1,3-oxazolidin-2-one and methanesulfonyl chloride. The crude material was purified on SPE cartridge (Silica) using as eluent a gradient from cyclohexane (100%) to cyclohexane-ethyl acetate (8:2) affording the final compound.

MS: (ES) m/z: 286 [MH$^+$]. $C_{12}H_{15}NO_5S$ requires 285.

1H-NMR (300 MHz, CDCl$_3$) δ(ppm): 7.5 (s, 1H), 7.3 (m, 2H), 6.95 (d, 1H), 4.3 (m, 4H), 4 (t, 2H), 3 (t, 2H), 2.8 (s, 3H).

3-(3-{2-[(2R)-2-Methyl-4-(2-methyl-5-quinolinyl)-1-piperazinyl]ethyl}phenyl)-1,3-oxazolidin-2-one (E125)

The title compound was prepared in 33% yield using a similar procedure to E124 starting from 2-methyl-5-[(3R)-3-methyl-1-piperazinyl]quinoline and 2-[3-(2-oxo-1,3-oxazolidin-3-yl)phenyl]ethyl methanesulfonate.

MS; (ES) m/z: 431.4 [MH]$^+$. $C_{26}H_{30}N_4O_2$ requires 430.

1H-NMR (500 MHz, d$_6$-DMSO) δ(ppm): 10.8-10.66 (2bs, 1H); 8.54 (bs, 1H); 7.72 (bs, 1H); 7.61 (s, 1H); 7.49 (m, 2H); 7.41 (t, 1H); 7.26 (m, 1H); 7.14 (m, 1H); 3.8 (t, 2H) 3.4 (m, 3H); 3.2-2.8 (bd-m, 9H), 2.71 (bm, 2H); 2.5 (s, 3H) 1.41 (d, 3H).

Example 126

1-(3-{2-[(2S)-2-Methyl-4-(2-methyl-5-quinolinyl)-1-piperazinyl]ethyl}phenyl)-2-imidazolidinone dihydrochloride (E126)

2-Methyl-5-[(3S)-3-methyl-1-piperazinyl]quinoline

The title compound was prepared in 27% yield using a similar procedure to Example 127 starting from (2S)-2-methylpiperazine and 2-methyl-5-quinolinyl trifluoromethanesulfonate (D1).

MS; (ES) m/z: 242.3 [MH]$^+$. $C_{15}H_{19}N_3$ requires 241.

$^1$H-NMR (300 MHz, CDCl$_3$) δ(ppm): 8.40 (d, 1H), 7.76 (d, 1H), 7.61 (t, 1H), 7.29 (d, 1H), 7.06 (d, 1H), 3.2 (m, 5H), 2.85 (t, 1H), 2.74 (s, 3H), 2.5 (t, 1H) 1.1 (d, 3H).

1-(3-{2-[(2S)-2-methyl-4-(2-methyl-5-quinolinyl)-1-piperazinyl]ethyl}phenyl)-2-imidazolidinone dihydrochloride (E126)

The title compound was prepared in 47% yield using a similar procedure to Example 127 starting from 2-methyl-5-[(3S)-3-methyl-1-piperazinyl]quinoline and 2-[3-(2-oxo-1-imidazolidinyl)phenyl]ethyl methanesulfonate.

MS; (ES) m/z: 430.4 [MH]$^+$. $C_{26}H_{31}N_5O$ requires 429.

$^1$H-NMR (500 MHz, DMSO) δ(ppm): 10.8-10.66 (2bs, 1H); 8.54 (bs, 1H); 7.72 (bs, 1H); 7.61 (s, 1H); 7.49 (m, 2H); 7.41 (t, 1H); 7.26 (m, 1H); 7.14 (m, 1H); 3.8 (t, 3H); 3.2 (t, 5H); 3.15/2.65 (bd-m, 7H); 2.5 (s, 3H); 1.3 (d, 3H).

Example 127

3-(3-{2-[(2S)-2-methyl-4-(2-methyl-5-quinolinyl)-1-piperazinyl]ethyl}phenyl)-1,3-oxazolidin-2-one (E127)

The title compound was prepared in 33% yield using a similar procedure to E124 starting from 2-methyl-5-[(3S)-3-methyl-1-piperazinyl]quinoline (D2) and 2-[3-(2-oxo-1,3-oxazolidin-3-yl)phenyl]ethyl methanesulfonate (Ex).

MS; (ES) m/z: 431.4 [MH]$^+$. $C_{26}H_{30}N_4O_2$ requires 430.

1H-NMR (500 MHz, d$_6$-DMSO) δ(ppm): 10.8-10.66 (2bs, 1H); 8.54 (bs, 1H); 7.72 (bs, 1H); 7.61 (s, 1H); 7.49 (m, 2H); 7.41 (t, 1H); 7.26 (m, 1H); 7.14 (m, 1H); 4.48 (t, 2H); 4.1 (t, 2H); 3.8/3.7-3 (bd-m, 11H); 2.71 (bm, 2H); 1.41 (d, 3H).

Example 128

3-(3-{(1R,2S)-2-[4-(2-Methyl-5-quinolinyl)-1-piperazinyl]cyclopropyl}phenyl)-1,3-oxazolidin-2-one dihydrochloride and 3-(3-{(1S,2R)-2-[4-(2-methyl-5-quinolinyl)-1-piperazinyl]cyclopropyl}phenyl)-1,3-oxazolidin-2-one dihydrochloride (E128)

3-[3-(2-Hydroxyethyl)phenyl]-1,3-oxazolidin-2-one

A solution 2-(3-bromophenyl)ethanol (1.00 g, 5.00 mmol), 2-oxazolidin-2-one (874 mg, 10.04 mmol), copper(I)iodide (96 mg, 0.50 mmol), N,N'-dimethyl-1,2-ethanediamine (60 μL, 49 mg, 0.56 mmol) and potassium carbonate (1.04 g, 7.50 mmol) were suspended in dioxane (6 mL). The mixture was stirred under nitrogen for 2.5 h at 100° C. After addition of copper(I)iodide (96 mg, 0.50 mmol) and N,N'-dimethyl-1,2-ethanediamine (60 μl, 49 mg, 0.56 mmol) stirring was continued for another 2 h at 100° C. After cooling down to room temperature, the mixture was poured into saturated aqueous ammonium chloride solution and extracted with dichloromethane. The organic layer was dried over magnesium sulfate and concentrated under reduced pressure. The crude compound was purified by flash chromatography on silica gel, eluting with ethyl acetate-cyclohexane (1:1 to 1:0) affording the title compound in 64% yield (664 mg).

1H-NMR (300 MHz, CDCl$_3$) δ(ppm): 7.4 (s, 1H), 7.0-7.3 (m, 2H), 7.85 (m, 1H), 4.25 (t, 2H), 3.85 (t, 2H), 3.65 (t, 2H), 2.65 (t, 2H), 1.50 (s, 1H).

[3-(2-oxo-1,3-oxazolidin-3-yl)phenyl]acetaldehyde 1,1,1-Tris(acetyloxy)-1,1-dihydro-1,2-benziodoxol-3 (1H)-one (Dess-Martin periodinane, 709 mg, 1.67 mmol) was added to a solution of 3-[3-(2-hydroxyethyl)phenyl]-1, 3-oxazolidin-2-one (315 mg, 1.52 mmol) in dichloromethane (10 mL). The mixture was stirred at room temperature for 30 min, then washed with aqueous sodium hydroxide solution (1M, 10 mL). The separated organic layer the latter was dried over magnesium sulfate and concentrated under reduced pressure affording the title compound in 89% yield (278 mg). The compound was used without further purification in the next step.

1H-NMR (300 MHz, CDCl$_3$) δ(ppm): 9.73 (s, 1H), 7.49 (s, 1H), 7.3-7.4 (m, 2H), 6.96 (m, 1H), 4.47 (t, 2H), 4.05 (t, 2H), 3.70 (s, 2H).

3-(3-{(1R,2S)-2-[4-(2-methyl-5-quinolinyl)-1-piperazinyl]cyclopropyl}phenyl)-1,3-oxazolidin-2-one dihydrochloride and 3-(3-{(1S,2R)-2-[4-(2-methyl-5-quinolinyl)-1-piperazinyl]cyclopropyl}phenyl)-1, 3-oxazolidin-2-one dihydrochloride (E128)

[3-(2-oxo-1,3-oxazolidin-3-yl)phenyl]acetaldehyde (275 mg, 1.34 mmol), para-toluenesulfonic acid hydrate (13 mg, 0.07 mmol) and 2-methyl-5-(1-piperazinyl)quinoline (304 mg, 1.340 mmol) were dissolved in toluene (30 mL) and heated for 2 h in a Dean-Stark-apparatus until the formation of the imine was complete (monitored by basic Al$_2$O$_3$-TLC-plates). After cooling to room temperature and evaporation of the solvent under reduced pressure, the crude imine was used without further purification.

Diiodomethane (0.22 mL, 718 mg, 2.68 mmol) was added to a solution of diethylzinc (1M in Hexanes, 2.0 mL, 2.00 mmol) in dry dichloromethane (5 mL) at 0° C. under nitrogen and stirred for 10 min. The crude imine was dissolved in dichloromethane (5 mL, dry) and added dropwise to the reaction mixture at 0° C. The reaction was warmed to room temperature and stirring was continued for another 2 h. The mixture was quenched with methanol, then loaded onto an ion exchange cartridge (SCX-2) and eluted with methanol followed by ammonia in methanol (1M). The basic fractions were concentrated under vacuum and purified by flash chromatography on silica gel, eluting with cyclohexane-ethyl acetate (1:1 to 1:2) and finally isolated via mass-directed HPLC (Fraction LYNX) affording the title compound in 2% yield (10 mg). The free base could be converted into its dihydrochloride salt by dissolving the compound in dichloromethane and adding a 1M ethereal solution of HCl (2.1 eq) dropwise. A yellow solid precipitated and the suspension was stirred for 15 min. The solvent was removed under reduced pressure affording a crude material which was triturated with ether. The title compound was then recovered by filtration (yield quantitative).

MS; (ES) m/z: 429 [MH$^+$]. C$_{26}$H$_{28}$N$_4$O$_2$ requires 428.

1H-NMR (500 MHz, d$_6$-DMSO) δ(ppm): 11.39 (bs, 1H), 8.84 (bs, 1H), 7.89 (bs, 2H), 7.77 (bs, 1H), 7.45 (d, 1H), 7.44 (s, 1H), 7.39 (bs, 1H), 7.34 (t, 1H), 6.96 (d, 1H), 4.44 (t, 2H), 4.07 (t, 2H), 3.8-3.0 (bm, 9H), 2.86 (bs, 3H), 1.87 (bs, 1H), 1.42 (bs, 1H).

Example 129

2,4-Dimethyl-N-(4-{(1R,2S)-2-[4-(2-methyl-5-quinolinyl)-1-piperazinyl]cyclopropyl}phenyl)-1,3-thiazole-5-carboxamide dihydrochloride and 2,4-dimethyl-N-(4-{(1R,2S)-2-[4-(2-methyl-5-quinolinyl)-1-piperazinyl]cyclopropyl}phenyl)-1,3-thiazole-5-carboxamide dihydrochloride (E129)

2-(3-Aminophenyl)ethanol 2-(3-Nitrophenyl)ethanol (836 mg, 5.00 mmol) and Pd (10% on charcoal, 200 mg) were suspended in dry methanol (10 mL). After the addition of ammonium formate (1.450 g, 23 mmol) a slightly exothermic and effervescent reaction was observed. After stirring for 1 h at room temperature the mixture was filtered over celite. The filtrate was evaporated and the residue dissolved in ethyl acetate. After washing with saturated aqueous sodium hydrogencarboante solution, water and brine the organic layer was dried (magnesium sulfate) and the solvent removed under reduced pressure affording the title compound in 54% yield (373 mg) as a white solid.

MS; (ES) m/z: 138 [MH$^+$]. C$_8$H$_{11}$NO requires 137.

1H-NMR (300 MHz, d$_6$-DMSO) δ(ppm): 6.80 (t, 1H), 6.25-6.35 (m, 3H), 4.85 (s, 2H), 4.50 (t, 1H), 3.45 (dt, 2H), 2.45 (t, 2H).

N-[3-(2-hydroxyethyl)phenyl]-2,4-dimethyl-1,3-thiazole-5-carboxamide 2-(3-Aminophenyl)ethanol (1.202 g, 8.76 mmol) was added to a solution of 2,4-dimethyl-1,3-thiazole-5-carboxylic acid (1.652 g, 10.51 mmol), 1-(3-dimethylaminopropyl)-3-ethylcarbodiimide hydrochloride (2.015 g, 10.51 mmol) and 1-hydroxybenzotriazole (1.420 g, 10.51 mmol) in dry DMF (20 mL). The mixture was stirred for 14 h then the DMF was removed under reduced pressure and the residue was partitioned between DCM and saturated aqueous sodium hydrogencarbonate solution. The organic layer was dried over magnesium sulfate and concentrated under reduced pressure. The crude compound was purified by flash chromatography on silica gel, eluting with ethyl acetate-cyclohexane (1:1 to 1:0) affording the title compound in 73% yield (1.772 g).

MS; (ES) m/z: 277 [MH$^+$]. C$_{14}$H$_{16}$N$_2$O$_2$S requires 276.

1H-NMR (300 MHz, d$_6$-DMSO) δ(ppm): 9.95 (s, 1H), 7.40-7.50 (m, 2H), 7.19 (t, 1H), 6.92 (d, 1H), 4.60 (t, 1H), 5.57 (dd, 2H), 2.66 (t, 2H), 2.61 (s, 3H), 2.49 (s, 3H).

2,4-Dimethyl-N-[3-(2-oxoethyl)phenyl]-1,3-thiazole-5-carboxamide

The title compound was synthesised according to the procedure described for E128 using N-[3-(2-hydroxyethyl)phenyl]-2,4-dimethyl-1,3-thiazole-5-carboxamide (800 mg, 2.895 mmol) and purified by flash chromatography on silica gel eluting with DCM-methanol (95:5) affording 519 mg (65%).

MS; (ES) m/z: 275 [MH$^+$]. C$_{14}$H$_{14}$N$_2$O$_2$S requires 274.

1H-NMR (300 MHz, CDCl$_3$) δ(ppm): 9.85 (s, 1H), 7.60 (m, 1H), 7.3-7.5 (m, 3H), 7.00 (d, 1H), 3.70 (s, 2H), 3.65 (s, 6H).

2,4-Dimethyl-N-(4-{(1R,2S)-2-[4-(2-methyl-5-quinolinyl)-1-piperazinyl]cyclopropyl}phenyl)-1,3-thiazole-5-carboxamide dihydrochloride and 2,4-dimethyl-N-(4-{(1R,2S)-2-[4-(2-methyl-5-quinolinyl)-1-piperazinyl]cyclopropyl}phenyl)-1,3-thiazole-5-carboxamide dihydrochloride (Example 129)

The title compound was synthesised according to the procedure described for E128 using 2,4-dimethyl-N-[3-(2-oxoethyl)phenyl]-1,3-thiazole-5-carboxamide (D6, 85 mg, 0.30 mmol) affording the enantiomeric mixture (5 mg, 3%).

MS; (ES) m/z: 498 [MH$^+$]. $C_{29}H_{31}N_5OS$ requires 497.

1H-NMR (500 MHz, $d_6$-DMSO) δ(ppm): 11.11 (bs, 1H), 10.09 (s, 1H), 8.78 (bs, 1H), 7.85 (bs, 2H), 7.73 (bs, 1H), 7.6 (s, 1H), 7.47 (d, 1H), 7.38 (bs, 1H), 7.29 (t, 1H), 6.97 (d, 1H), 3.8-3.0 (bm, 9H), 2.7-2.9 (bs, 4H), 2.65 (s, 3H), 2.53 (s, 3H), 1.85 (bs, 1H), 1.4 (bs, 1H).

Example 130

1-Methyl-3-(3-{2-[4-(2-methyl-5-quinolinyl)-1-piperazinyl]ethyl}phenyl)-2-imidazolidinone (E130)

To a stirred solution of 1-(3-{2-[4-(2-methyl-5-quinolinyl)-1-piperazinyl]ethyl}phenyl)-2-imidazolidinone (E85) in THF was added methyl iodide (1 eq.), followed by sodium hydride (1.2 eq), and the reaction was stirred for 60 minutes. The mixture was loaded onto an ion-exchange cartridge (SCX-2) and eluted with methanol followed by ammonia in methanol (1M). The basic fractions were concentrated under vacuum and purified by column chromatography (SPE cartridge, Silica) using as eluent a gradient from DCM-methanol (99:1) to DCM-methanol (98:2) affording the final compound (45% yield).

MS: (ES/+) m/z: 430 [MH$^+$] $C_{26}H_{31}N_5O_2$ requires 429.

1H-NMR (400 MHz, $d_6$-DMSO) δ(ppm): 11.19 (1H, bs), 8.94 (1H, bs), 7.99 (2H, bs), 7.84 (1H, bd), 7.6 (1H, bs), 7.48 (1H, bs), 7.45 (1H, d), 7.32 (1H, t), 6.96 (1H, d), 3.81 (2H, t), 3.73 (2H, bd), 3.7-3.2 (10H, m), 3.13 (2H, m), 2.93 (3H, bs), 2.79 (3H, s).

Example 131

N-(2-(Methoxy)-3-{2-[4-(2-methyl-5-quinolinyl)-1-piperazinyl]ethyl}phenyl)acetamide dihydrochloride (E131)

2-(Methoxy)-3-nitrobenzaldehyde

To a solution of 2-hydroxy-3-nitrobenzaldehyde in DMF was added portionwise cesium carbonate (3 eq), followed by iodomethane (1.2 eq.). The solution was warmed to 60° C. for 2 hours, then cooled to room temperature and filtered. The filtrate was concentrated under vacuum and purified by column chromatography on SPE cartridge (Silica) using as eluent cyclohexane-ethyl acetate (8:2) to give the product in 72% yield.

1H-NMR (300 MHz, CDCl$_3$) δ(ppm): 10.28 (1H, s), 7.95 (2H, m), 7.23 (1H, m), 3.97 (3H, s).

[2-(Methoxy)-3-nitrophenyl]acetaldehyde

To a stirred solution of 2-(methoxy)-3-nitrobenzaldehyde in THF were added 18-Crown-6 (0.2 eq), (methoxymethyl)triphenylphosphonium chloride (2 eq) and potassium carbonate (6.5 eq). The resulting suspension was warmed to 60° C. for 2 hours then cooled to room temperature and filtered. The filtrate was concentrated under vacuum and purified by chromatography on a silica cartridge (eluent cyclohexane-ethyl acetate, 9:1) to give a mixture of 2-(methoxy)-1-[(E)-2-(methoxy)ethenyl]-3-nitrobenzene and 2-(methyloxy)-1-[(Z)-2-(methyloxy)ethenyl]-3-nitrobenzene. The alkene mixture was dissolved in THF and 6N hydrochloric acid (1:1), and stirred for 1 hour. The solution was made basic with aqueous sodium carbonate solution and extracted with DCM. The organic layer was washed (water, brine), dried (sodium sulfate) and concentrated under vacuum to give the title compound (54% overall yield).

1H-NMR (300 MHz, CDCl$_3$) δ(ppm): 9.75 (1H, s), 7.8 (1H, d), 7.4 (1H, d), 7.2 (1H, m), 3.85 (3H, s), 3.8 (2H, s).

2-(Methoxy)-3-{2-[4-(2-methyl-5-quinolinyl)-1-piperazinyl]ethyl}aniline

To a stirred solution of [2-(methoxy)-3-nitrophenyl] in acetonitrile was added 2-methyl-5-(1-piperazinyl)quinoline and the solution was stirred at room temperature for 15 minutes. Sodium triacetoxyborohydride was added and the suspension was stirred for 75 minutes. The intermediate, 2-methyl-5-(4-{2-[2-(methoxy)-3-nitrophenyl]ethyl}-1-piperazinyl)quinoline, was recovered by ion-exchange chromatography [SCX-2 cartridge; methanol-ammonia/methanol (1M), (1:0)→(0:1)].

The title compound was obtained in 71% overall yield from 2-methyl-5-(4-{2-[2-(methoxy)-3-nitrophenyl]ethyl}-1-piperazinyl)quinoline according to the procedure contained within Description 6 (D6).

MS: (ES/+) m/z: 377 [MH$^+$] $C_{23}H_{28}N_4O$ requires 376.

1H-NMR (300 MHz, CDCl$_3$) δ(ppm): 8.37 (1H, d), 7.68 (1H, d), 7.57 (1H, t), 7.22 (1H, d), 7.07 (1H, d), 6.88 (1H, t), 6.63 (2H, d), 3.76 (4H, bs), 3.13 (4H, bs), 2.95-2.6 (10H, vbm).

N-(2-(Methoxy)-3-{2-[4-(2-methyl-5-quinolinyl)-1-piperazinyl]ethyl}phenyl)acetamide dihydrochloride (E131)

The title compound was prepared in 42% yield according to the general procedure for the preparation of amides (Method B) starting from starting from 2-(methoxy)-3-{2-[4-(2-methyl-5-quinolinyl)-1-piperazinyl]ethyl}aniline and acetyl chloride.

MS: (ES/+) m/z: 419 [MH$^+$] $C_{25}H_{30}N_4O_2$ requires 418.

1H-NMR (400 MHz, $d_6$-DMSO) δ(ppm): 10.64 (1H, b), 9.38 (1H, s), 8.77 (1H, bs), 7.84 (3H, m), 7.72 (1H, bs), 7.39 (1H, s), 7.09 (2H, m), 3.77 (3H, s), 3.52 (2H, m), 3.6-3.3 (8H, m), 3.15 (2H, m), 2.83 (3H, s), 2.14 (3H, s).

Example 132

N-(2-(Methoxy)-3-{2-[4-(2-methyl-5-quinolinyl)-1-piperazinyl]ethyl}phenyl)methanesulfonamide dihydrochloride (E132)

The title compound was prepared in 72% yield according to the general procedure for the preparation of amides (Method B) starting from 2-(methoxy)-3-{2-[4-(2-methyl-5-quinolinyl)-1-piperazinyl]ethyl}aniline and methanesulfonyl chloride.

MS: (ES/+) m/z: 455 [MH$^+$] $C_{25}H_{30}N_4O_2$ requires 454.

1H-NMR (400 MHz, $d_6$-DMSO) δ(ppm): 10.68 (1H, b), 9.19 (1H, s), 8.8 (1H, bs), 7.87 (2H, bs), 7.72 (1H, bs), 7.39

(1H, s), 7.33 (1H, m), 7.16 (2H, m), 3.82 (3H, s), 3.77 (2H, m), 3.6-3.3 (8H, m), 3.15 (2H, m), 3.11 (3H, s), 2.83 (3H, s).

Example 133

3-(2-(Methoxy)-3-{2-[4-(2-methyl-5-quinolinyl)-1-piperazinyl]ethyl}phenyl)-1,3-oxazolidin-2-one dihydrochloride (E133)

The title compound was prepared in 63% yield according to the general procedure for the synthesis of cyclic ureas and carbamates (Method G) starting from 2-(methoxy)-3-{2-[4-(2-methyl-5-quinolinyl)-1-piperazinyl]ethyl}aniline and (2-bromoethyl)carbamyl chloride.

MS: (ES/+) m/z: 447 [MH$^+$] $C_{26}H_{30}N_4O_3$ requires 446.

1H-NMR (400 MHz, d$_6$-DMSO) δ(ppm): 10.73 (1H, b), 8.82 (1H, bs), 7.88 (2H, bs), 7.75 (1H, bs), 7.42 (1H, s), 7.38 (1H, dd), 7.31 (1H, dd), 7.21 (1H, t), 4.51 (2H, t), 3.97 (2H, t), 3.81 (3H, s), 3.77 (2H, m), 3.6-3.3 (8H, m), 3.17 (2H, m), 2.85 (3H, s).

Example 134

1-(2-(Methoxy)-3-{2-[4-(2-methyl-5-quinolinyl)-1-piperazinyl]ethyl}phenyl)-2-imidazolidinone dihydrochloride (E134)

The title compound was prepared in 38% yield according to the general procedure for the synthesis of cyclic ureas and carbamates (Method G) starting from 2-(methoxy)-3-{2-[4-(2-methyl-5-quinolinyl)-1-piperazinyl]ethyl}aniline and 1-chloro-2-isocyanatoethane.

MS: (ES/+) m/z: 446 [MH$^+$] $C_{26}H_{31}N_5O_2$ requires 445.

1H-NMR (400 MHz, d$_6$-DMSO) δ(ppm): 10.78 (1H, b), 8.85 (1H, bs), 7.9 (2H, bs), 7.76 (1H, bs), 7.42 (1H, s), 7.3 (1H, dd), 7.21 (1H, dd), 7.13 (1H, t), 6.79 (1H, bs), 3.79 (3H, s), 3.78 (2H, t), 3.6-3.3 (12H, m), 3.15 (2H, m), 2.87 (3H, s).

Example 135

1-Methyl-3-(2-(methoxy)-3-{2-[4-(2-methyl-5-quinolinyl)-1-piperazinyl]ethyl}phenyl)-2-imidazolidinone dihydrochloride (E135)

The title compound was prepared in 20% yield according to procedure described for Example 130 starting from 1-(2-(methoxy)-3-{2-[4-(2-methyl-5-quinolinyl)-1-piperazinyl]ethyl}phenyl)-2-imidazolidinone and iodomethane.

MS: (ES/+) m/z: 460 [MH$^+$] $C_{26}H_{31}N_5O_2$ requires 459.

1H-NMR (400 MHz, d$_6$-DMSO) δ(ppm): 10.95 (1H, b), 10.7-10.5 (1H, b), 8.88 (1H, bs), 7.93 (2H, bs), 7.8 (1H, bs), 7.44 (1H, s), 7.27 (1H, dd), 7.21 (1H, dd), 7.14 (1H, t), 3.77 (2H, m), 3.76 (3H, s), 3.7 (2H, t), 3.6-3.3 (8H, m), 3.17 (2H, m), 2.9 (5H, m), 2.87 (3H, s).

Example 136

N-(4-Fluoro-3-{2-[4-(2-methyl-5-quinolinyl)-1-piperazinyl]ethyl}phenyl)acetamide (E136)

The title compound was prepared in 66% yield according to the general procedure for the preparation of the amides, ureas and carbamates (Method A) starting from 5-{4-[2-(5-bromo-2-fluorophenyl)ethyl]-1-piperazinyl}-2-methylquinoline and acetamide.

MS: (ES/+) m/z: 407 [MH$^+$]. $C_{24}H_{27}FN_4O$ requires 406.

1H-NMR (400 MHz, d$_6$-DMSO) δ(ppm): 10.69 (br s, 1H), 10.08 (s, 1H), 8.82 (br s, 1H), 7.88 (br s, 2H), 7.75 (br s, 1H), 7.74 (dd, 1H), 7.41 (m, 1H), 7.19 (t, 1H), 3.77 (dd, 2H), 3.61-3.30 (m, 8H), 3.14 (m, 2H), 2.85 (s, 3H), 2.06 (s, 6H).

5-{4-[2-(5-Bromo-2-fluorophenyl)ethyl]-1-piperazinyl}-2-methylquinoline

The title compound was prepared in 95% yield from (5-bromo-2-fluorophenyl)acetaldehyde (0.98 g), 2-methyl-5-(1-piperazinyl)quinoline (0.51 g) and sodium triacetoxyborohydride (0.95 g) according to the procedure described for Example 131.

MS: (ES/+) m/z: 428, 430 [MH$^+$]. $C_{22}H_{23}BrFN_3$ requires 427, 429.

1H-NMR (300 MHz, CDCl$_3$) δ(ppm): 8.37 (d, 1H), 7.69 (d, 1H), 7.52 (t, 1H), 7.40 (dd, 1H), 7.26-7.18 (m, 2H), 7.07 (dd, 1H), 6.88 (t, 1H), 3.11 (m, 4H), 2.90-2.75 (m, 6H), 2.69 (s, 3H) and 2.68 (m, 2H).

(5-Bromo-2-fluorophenyl)acetaldehyde

The title compound was prepared from (E/Z)-2-(5-bromo-2-fluorophenyl)ethenyl methyl ether according to the procedure described for Example 131 and used without further purification or characterisation.

(E/Z)-2-(5-Bromo-2-fluorophenyl)ethenyl methyl ether

The title compound was prepared in 48% yield from 5-bromo-2-fluorobenzaldehyde (2.00 g) and (methoxymethyl)triphenylphosphonium chloride (4.05 g) according to the procedure described for Example 131.

1H-NMR (300 MHz, CDCl$_3$) δ(ppm): 8.07 (d, 0.5H), 7.30-7.00 (m, 2H), 6.72 (m, 1H), 6.17 (d, 0.5H), 5.65 (d, 0.5H), 5.32 (d, 0.5H), 3.68 (s, 1.5H) and 3.59 (s, 1.5H).

Example 137

N-(4-Fluoro-3-{2-[4-(2-methyl-5-quinolinyl)-1-piperazinyl]ethyl}phenyl)-2,2-dimethylpropanamide (E137)

The title compound was prepared in 52% yield according to the general procedure for the preparation of amides, ureas and carbamates (Method A) starting from 5-{4-[2-(5-bromo-2-fluorophenyl)ethyl]-1-piperazinyl}-2-methylquinoline and 2,2-dimethylpropanamide.

MS: (ES/+) m/z: 449 [MH$^+$]. $C_{27}H_{33}FN_4O$ requires 448.

1H-NMR (400 MHz, d$_6$-DMSO) δ(ppm): 10.56 (br s, 1H), 9.33 (s, 1H), 8.77 (br s, 1H), 7.84 (br s, 2H), 7.8 (dd, 1H), 7.71 (br s, 1H), 7.51 (m, 1H), 7.39 (br s, 1H), 7.19 (t, 1H), 3.77 (dd, 2H), 3.61-3.30 (m, 8H), 3.14 (m, 2H), 2.83 (s, 3H), 1.24 (s, 9H).

Example 138

N-(4-Fluoro-3-{2-[4-(2-methyl-5-quinolinyl)-1-piperazinyl]ethyl}phenyl)methanesulfonamide (E138)

The title compound was prepared in 69% yield according to the general procedure for the preparation of amides, ureas and carbamates (Method A) starting from 5-{4-[2-(5-bromo-2-fluorophenyl)ethyl]-1-piperazinyl}-2-methylquinoline and methanesulfonamide.

MS: (ES/+) m/z: 434 [MH$^+$]. $C_{23}H_{28}FN_5O$ requires 433.

1H-NMR (400 MHz, d$_6$-DMSO) δ(ppm): 10.92 (br s, 1H), 9.78 (s, 1H), 8.77 (br s, 1H), 7.92 (br s, 2H), 7.78 (br s, 1H), 7.43 (br s, 1H), 7.3-7.15 (m, 3H), 3.76 (dd, 2H), 3.6-3.3 (m, 8H), 3.17 (m, 2H), 3.01 (s, 3H), 2.85 (s, 3H).

Example 139

1-(4-Fluoro-3-{2-[4-(2-methyl-5-quinolinyl)-1-piperazinyl]ethyl}phenyl)-2-imidazolidinone (E139)

The title compound was prepared in 35% yield according to the general procedure for the preparation of amides, ureas and carbamates (Method A) starting from 5-{4-[2-(5-bromo-2-fluorophenyl)ethyl]-1-piperazinyl}-2-methylquinoline and 2-imidazolidone.

MS: (ES/+) m/z: 434 [MH$^+$]. C$_{23}$H$_{27}$FN$_4$OS requires 433.

1H-NMR (400 MHz, d$_6$-DMSO) δ(ppm): 10.64 (br s, 1H), 8.33 (br s, 1H), 7.88 (br s, 2H), 7.74 (br s, 1H), 7.67 (dd, 1H), 7.45 (dd, 1H), 7.4 (br s, 1H), 7.21 (t, 1H), 7.02 (s, 1H), 3.86 (t, 2H), 3.77 (dd, 2H), 3.6-3.3 (m, 10H), 3.16 (m, 2H), 2.85 (s, 3H).

Example 140

3-(4-Fluoro-3-{2-[4-(2-methyl-5-quinolinyl)-1-piperazinyl]ethyl}phenyl)-1,3-oxazolidin-2-one (E140)

The title compound was prepared in 95% yield according to the general procedure for the preparation of the amides, ureas and carbamates (Method A) starting from 5-{4-[2-(5-bromo-2-fluorophenyl)ethyl]-1-piperazinyl}-2-methylquinoline and 2-imidazolidone.

MS: (ES/+) m/z: 435 [MH$^+$]. C$_{25}$H$_{28}$FN$_5$O requires 434.

1H-NMR (400 MHz, d$_6$-DMSO) δ(ppm): 10.73 (br s, 1H), 8.85 (br s, 1H), 7.89 (br s, 2H), 7.77 (br s, 1H), 7.68 (dd, 1H), 7.5 (dd, 1H), 7.43 (br s, 1H), 7.39 (t, 1H), 4.47 (dd, 2H), 4.09 (dd, 2H), 3.77 (dd, 2H), 3.6-3.3 (m, 8H), 3.19 (m, 2H), 2.87 (s, 3H).

Example 141

1-(3-{2-[4-(2-methyl-5-quinolinyl)-1-piperazinyl]ethyl}phenyl)-2,4-imidazolidinedione dihydrochloride (E141)

5-{4-[2-(3-Iodophenyl)ethyl]-1-piperazinyl}-2-methylquinoline (46 mg, 0.100 mmol), hydantoin (44.8 mg, 0.444 mmol), potassium carbonate (23.1 mg, 0.167 mmol), copper (I)iodide (107 mg, 0.561 mmol) and N,N'-dimethyl-1,2-ethanediamine (60 L, 50 mg, 0.563 mmol) were dissolved in dioxane (2 mL) and heated at 150 C for 75 min via microwave irradiation. The mixture was cooled to room temperature and partitioned between water and ethyl acetate. The organic layer was dried over magnesium sulfate and concentrated under reduced pressure. The crude compound was purified by flash chromatography on silica gel, eluting with dichloromethane-methanol (97:3 to 95:5) afforded the title compound in 23% yield (10 mg) as the first-eluting hydantoin regioisomer.

MS: (ES/+) m/z: 430 [MH$^+$] C$_{25}$H$_{27}$N$_5$O$_2$ requires 429.

1H-NMR (400 MHz, d$_6$-DMSO) δ (ppm): 11.12 (1H, bs), 8.3 (1H, d), 7.55 (2H, m), 7.48 (1H, bs), 7.4 (1H, bd), 7.35 (1H, d), 7.24 (1H, t), 7.06 (1H, dd), 6.97 (1H, bd), 4.4 (2H, s), 3(4H, bs), 2.8-2.5 (8H, bm), 2.59 (3H, s).

Example 142

3-(3-{2-[4-(2-Methyl-5-quinolinyl)-1-piperazinyl]ethyl}phenyl)-2,4-imidazolidinedione dihydrochloride (E142)

The title compound was prepared according to the method described for Example 144 and isolated in 18% yield (8 mg) as the second-eluting hydantoin regioisomer.

MS: (ES/+) m/z: 430 [MH$^+$] C$_{25}$H$_{27}$N$_5$O$_2$ requires 429.

1H-NMR (400 MHz, d$_6$-DMSO) (ppm): 8.23 (1H, bd), 8.24 (1H, bs), 7.55 (2H, bs), 7.34 (1H, bd), 7.4-7.0 (5H, m), 4.02 (2H, s), 3 (4H, bs), 2.81-2.59 (8H, bm), 2.59 (3H, s).

Example 143

(R or S) 3-(3-{2-[(2R)-2-Methyl-4-(2-methyl-5-quinolinyl)-1-piperazinyl]propyl}phenyl)-1,3-oxazolidin-2-one dihydrochloride (E143)

A mixture of 3-[3-(2-oxopropyl)phenyl]-1,3-oxazolidin-2-one and 2-methyl-5-[(3R)-3-methyl-1-piperazinyl]quinoline (1.2 eq) was suspended in titanium(IV) isopropoxide (2 eq), and stirred for 12 hours. The solution was gently warmed to 60° C. and stirred for 1 hour, then methanol was added, followed by sodium borohydride (9 eq) and the mixture was stirred for a further 4 hours. The solution was poured into aqueous ammonium chloride solution and extracted with DCM. The organic phase was concentrated under vacuum and purified by chromatography (SPE cartridge, silica) using as eluent a gradient from dichloromethane-methanol (99:1) to (98:2) affording the diastereomeric mixture (34% yield). Separation using preparative HPLC (Chiralpak AD 10 m, 250×20 mm; mobile phase: A: n-Hexane, B: isopropanol+ 0.1% 2-propanol; gradient: isocratic 20% B; flow rate: 7 mL/min; UV wavelength range: 220 nm; analysis time: 60 min) produced the title compound free base as the first-eluting diastereoisomer. The free base was dissolved in dichloromethane and treated with 1M ethereal hydrogen chloride solution (2.1 eq). A yellow solid precipitated and the suspensions were stirred for 15 min. The solvent was removed under reduced pressure affording a solid, which was triturated with ether. The title compound was then recovered by filtration (yield quantitative).

MS: (ES/+) m/z: 445 [MH$^+$] C$_{27}$H$_{32}$N$_4$O$_2$ requires 444.

1H-NMR (400 MHz, d$_6$-DMSO) δ(ppm): 10.96 (1H, vbs), 8.96 (1H, vbs), 7.9 (2H, bs), 7.76 (1H, bs), 7.62 (1H, s), 7.4 (3H, m), 7.15 (1H, d), 4.47 (2H, t), 4.1 (2H, m), 4-3.2 (10H, vbm), 2.87 (3H, bs), 1.42 (3H, d), 1.24 (3H, d).

Example 144

(S or R) 3-(3-{2-[(2R)-2-methyl-4-(2-methyl-5-quinolinyl)-1-piperazinyl]propyl}phenyl)-1,3-oxazolidin-2-one dihydrochloride (E144)

The title compound was isolated as the second-eluting diastereoisomer from the procedure described for Example 143.

MS: (ES/+) m/z: 445 [MH$^+$] C$_{27}$H$_{32}$N$_4$O$_2$ requires 444.

1H-NMR (400 MHz, d$_6$-DMSO) δ(ppm): 10.82 (1H, vbs), 8.97 (1H, vbs), 7.92 (2H, bs), 7.78 (1H, bs), 7.64 (1H, s), 7.4 (3H, m), 7.14 (1H, d), 4.47 (2H, t), 4.11 (2H, m), 4-2.7 (10H, vbm), 2.89 (3H, bs), 1.5 (3H, d), 1.32 (3H, d).

Example 145

1-(3-{2-[4-(2-Methyl-5-quinolinyl)-1-piperazinyl]ethyl}phenyl)-1,3-dihydro-2H-imidazol-2-one dihydrochloride (E145)

A mixture of 5-{4-[2-(3-iodophenyl)ethyl]-1-piperazinyl}-2-methylquinoline (117 mg, 0.256 mmol), 1,3-dihydro-2H-imidazol-2-one (84 mg, 1.023 mmol, Whitney, R. A., Tet. Lett. 1981, 22, 2063-2066), potassium carbonate (53 mg, 0.384 mmol), copper(I)iodide (244 mg, 1.28 mmol) and N,N'-dimethyl-1,2-ethanediamine (163 L, 135 mg, 1.536 mmol) and dioxane (2.5 mL) was heated at 150° C. for 90 min under microwave irradiation. The mixture was cooled to room temperature and partitioned between water and ethyl acetate. The organic layer was dried over magnesium sulfate and concentrated under reduced pressure. The crude compound was purified by flash chromatography on silica gel, eluting with dichloromethane-methanol (97:3) affording the title compound in 20% yield (23 mg). The free base was converted into its dihydrochloride salt by dissolving the compound in dichloromethane and adding a 1M ethereal solution of HCl (2.1 eq) dropwise. A yellow solid precipitated and the suspension was stirred for 15 min. The solvent was removed under reduced pressure; the residue was triturated with ether. The title compound was then recovered by filtration (yield quantitative).

MS: (ES/+) m/z: 414 [MH$^+$] $C_{25}H_{27}N_5O$ requires 413.

1H-NMR (400 MHz, $d_6$-DMSO) δ (ppm): 10.75 (1H, bs), 10.28 (s, 1H), 8.78 (bs, 1H), 7.84 (bs, 2H), 7.7 (bs, 1H), 7.69 (t, 1H), 7.56 (dd, 1H), 7.38 (t, 1H), 7.36 (bs, 1H), 7.13 (d, 1H), 6.92 (dd, 1H), 6.58 (dd, 1H), 3.69 (bd, 2H), 3.5-3.2 (8H), 3.12 (m, 2H), 2.81 (bs, 3H).

Example 146

1-Methyl-3-(3-{2-[4-(2-methyl-5-quinolinyl)-1-piperazinyl]ethyl}phenyl)-1,3-dihydro-2H-imidazol-2-one dihydrochloride (E146)

To a solution of 1-(3-{2-[4-(2-methyl-5-quinolinyl)-1-piperazinyl]ethyl}phenyl)-1,3-dihydro-2H-imidazol-2-one (E145 free-base, 23 mg, 0.056 mmol) in dry DMF (1 mL) at 0° C. was added sodium hydride (3.5 mg, 0.084 mmol, 60% suspension in mineral oil). After stirring for 30 min methyl iodide was added (4 μL, 9.5 mg, 0.067 mmol) and stirring was continued for 6 h. Methanol was added, the mixture was loaded onto an ion-exchange cartridge (SCX-2) and the crude product liberated by elution with ammonia in methanol solution (1N). The crude compound was purified by flash chromatography on silica gel, eluting with dichloromethane-methanol (99:1 to 97:3) affording the title compound in 23% yield (5.5 mg). The free base was converted into its dihydrochloride salt by dissolving the compound in dichloromethane and adding a 1M ethereal solution of HCl (2.1 eq) dropwise. A yellow solid precipitated and the suspension was stirred for 15 min. The solvent was removed under reduced pressure; the residue was triturated with ether. The title compound was then recovered by filtration (yield quantitative).

MS: (ES/+) m/z: 428 [MH$^+$] $C_{26}H_{29}N_5O$ requires 427.

1H-NMR (400 MHz, $d_6$-DMSO) (ppm): 11.5 (2vbs, 1H), 8.79 (vbs, 1H), 7.87 (bs, 2H), 7.74 (bs, 2H), 7.63 (d, 1H), 7.46 (t, 1H), 7.4 (bs, 1H), 7.21 (d, 1H), 7.04 (d, 1H), 6.78 (d, 1H), 3.8-2.9 (vbm, 12H), 3.21 (s, 3H), 2.85 (bs, 3H).

Example 147

N-(3-{2-[4-(2-methyl-5-quinazolinyl)-1-piperazinyl]ethyl}phenyl)methanesulfonamide (E147)

A mixture of 2-methyl-5-(1-piperazinyl)quinazoline (50 mg), 2-{3-[(methylsulfonyl)amino]phenyl}ethyl methanesulfonate (65 mg), diisopropylethylamine (192 μL) and DMF (0.5 mL) was heated to 100° C. in a sealed tube and stirred for 24 hours. The mixture was cooled to room temperature and partitioned between aqueous ammonium chloride solution and ethyl acetate. The organic layer was washed (water, brine), dried (sodium sulfate) and concentrated in vacuo. The residue was purified by column chromatography [SiO$_2$; DCM-MeOH: (100:0)→(95:5)] to give the title compound as a beige foam (35 mg).

MS; (ES) m/z: 426 [MH$^+$]. $C_{22}H_{27}N_5O_2S$ requires 425.

1H-NMR (400 MHz, $d_6$-DMSO) δ(ppm): 9.65 (s, 1H), 9.48 (s, 1H), 7.82 (t, 1H), 7.50 (d, 1H), 7.24 (t, 1H), 7.15 (d, 1H), 7.11 (s, 1H), 7.04 (d, 1H), 7.01 (d, 1H), 3.12 (m, 4H), 2.97 (s, 3H), 2.75 (m, 6H), 2.73 (s, 3H) and 2.63 (m, 2H).

2-{3-[(Methylsulfonyl)amino]phenyl}ethyl methanesulfonate

The title compound was prepared from 3-aminophenethyl alcohol (U.S. Pat. No. 2,641,602) and methanesulfonyl chloride (2 eq.) according to the procedure contained within description 4. The product was used immediately without further purification or characterisation.

2-Methyl-5-(1-piperazinyl)quinazoline

To a stirred solution of 2-methyl-5-fluoro-quinazoline (WO2003068772, Chem. Abstr. 139:197493, 2 g; 12.3 mmol) in dry dimethylformamide (10 mL) were added triethylamine (3.4 mL; 2 eq) and piperazine (11 g; 10 eq). The reaction mixture was stirred under nitrogen at 120° C. for 4 h, then cooled to room temperature, poured into water (10 mL) and extracted with ethyl acetate (5×15 mL). The organic layers were combined, dried over sodium sulfate and concentrated in vacuo. The crude product was purified by ion-exchange chromatography [SCX-2; MeOH-1M NH$_3$/MeOH (1:0)→(0:1)] to afford the title compound as a yellow solid (1.8 g; yield 64%).

MS; (ES) m/z: 229.2 [MH$^+$]. $C_{11}H_8F_3NO_3S$ requires 228.

1H-NMR (300 MHz, CDCl$_3$) δ (ppm): 9.58 (s, 1H), 7.89 (t, 1H), 7.62 (d, 1H), 7.27 (d, 1H), 3.25 (m, 8H); 2.91 (s, 3H).

Example 148

N-(3-{2-[4-(2-methyl-5-quinolinyl)-1-piperazinyl]ethyl}phenyl)-N-(methylsulfonyl)methanesulfonamide (E148)

To a stirred solution of 3-{2-[4-(2-methyl-5-quinolinyl)-1-piperazinyl]ethyl}aniline (370 mg) and triethylamine (178 μL) in DCM (3 mL) was added methanesulfonyl chloride (33 L). The mixture was stirred for 18 h, then partitioned between saturated aqueous sodium hydrogencarbonate solution and DCM. The organic layer was washed with water, dried and concentrated in vacuo. The residue was purified by column chromatography [SiO$_2$; DCM-MeOH, (20:0)→(20:1)] to give the title compound (342 mg).

MS; (ES) m/z: 503 [MH$^+$]. $C_{24}H_{30}N_4O_4S_2$ requires 502.

1H-NMR (400 MHz, d$_6$-DMSO) δ(ppm): 8.33 (d, 1H), 7.6-7.5 (m, 2H), 7.42-7.30 (m, 5H), 7.09 (dd, 1H), 3.52 (s, 6H), 3.02 (bm, 4H), 2.86 (t, 2H), 2.8-2.6 (m, 6H) and 2.62 (s, 3H).

Example 149

N-methyl-N-(3-{2-[4-(2-methyl-5-quinolinyl)-1-piperazinyl]ethyl}phenyl)acetamide (E149)

A solution of N-(3-{2-[4-(2-methyl-5-quinolinyl)-1-piperazinyl]ethyl}phenyl)acetamide (50 mg) was dissolved in THF (2.5 mL) and sodium hydride (60% w/w oil dispersion, 0.005 g, 1 eq.) was added at 0° C. After 5 minutes iodomethane was added (5 uL, 1.0 eq.) and the mixture was warmed to room temperature. After 10 h the solution was partitioned between water (3 mL) and ethyl acetate (3×5 mL). The combined organic extracts were washed with brine, dried over sodium sulfate and concentrated under vacuum. The crude was purified by flash chromatography on silica gel, eluting with a gradient from dichloromethane to dichloromethane-methanol (98:2) affording the title compound in 61% yield (0.02 g).

MS: (ES) m/z: 403.4 [MH$^+$]. C$_{25}$H$_{31}$ClNO$_4$ requires 402.
1H-NMR (300 MHz, D6-DMSO) δ(ppm): 10.85 (bs, 1H), 8.79 (bs, 1H), 8-7 (bm, 16H), 3.8-3.0 (bm, 15H), 2.84 (bs, 3H), 1.79 (bs, 3H).

Example 150

N-(1-Methylethyl)-N'-(3-{2-[4-(2-methyl-5-quinolinyl)-1-piperazinyl]ethyl}phenyl)urea (E150)

The title compound was prepared from 3-{2-[4-(2-methyl-5-quinolinyl)-1-piperazinyl]ethyl}aniline (D6, 30 mg), isopropyl isocyanate (10.2 μL) using toluene (1 mL) as solvent according to Method E. Yield 23 mg.

MS: (ES) m/z: 432 [MH$^+$]. C$_{26}$H$_{33}$N$_5$O requires 431.
1H-NMR (400 MHz, CDCl$_3$) δ(ppm): 8.40 (d, 1H), 7.73 (d, 1H), 7.60 (t, 1H), 7.3-7.2 (m, 3H), 7.09 (d, 2H), 6.99 (d, 1H), 6.15 (s, 1H), 4.49 (d, 1H), 4.02 (m, 1H), 3.16-2.83 (m, 12H) and 1.2, (d, 6H).

Example 151

N-methyl-N-(3-{2-[4-(2-methyl-5-quinolinyl)-1-piperazinyl]ethyl}phenyl)methanesulfonamide (E151)

A sample of N-(3-{2-[4-(2-methyl-5-quinolinyl)-1-piperazinyl]ethyl}phenyl)methanesulfonamide, hydrochloride salt (E43, 25 mg) was partitioned between saturated aqueous sodium hydrogencarbonate solution and DCM. The organic phase was dried over sodium sulfate and concentrated in vacuo to give the free-base (18.5 mg), which was dissolved in THF (1.5 mL) and cooled to 0° C. To the stirred solution was added sodium hydride (60%, 5 mg). The mixture was stirred for 30 minutes then iodomethane (5 μL) was added. The mixture was warmed to room temperature and stirred for 18 h. The mixture was cooled to 0° C. and further portions of sodium hydride (60%, 5 mg) and iodomethane (5 μL) were added. The mixture was warmed to room temperature and stirred for 24 h, then partitioned between aqueous ammonium chloride solution and DCM. The organic layer was washed (water), dried (sodium sulfate) and concentrated in vacuo. The residue was purified using column chromatography (SiO$_2$; DCM-MeOH, 97:3) to give the title compound (5 mg).

MS; (ES) m/z: 439 [MH$^+$]. C$_{24}$H$_{30}$N$_4$O$_2$S requires 438.
1H-NMR (300 MHz, CDCl$_3$) δ(ppm): 8.32 (d, 1H), 7.70 (d, 1H), 7.58 (t, 1H), 7.30-7.20 (m, 3H), 7.17 (s, 1H), 7.10-7.00 (m, 3H), 3.78 (t, 2H), 3.37 (t, 2H), 3.12 (m, 4H), 2.87 (m, 2H), 2.80 (m, 4H), 2.72 (m, 2H), 2.71 (s, 3H) and 2.52 (quint., 2H).

Example 152

1-(3-{2-[4-(2-Methyl-5-quinolinyl)-1-piperazinyl]ethyl}phenyl)-2-pyrrolidinone (E152)

1-[3-(2-Hydroxyethyl)phenyl]-2-pyrrolidinone

The title compound was prepared in 15% yield according to the general procedure for the preparation of the amides, ureas and carbamates (Method A) starting from 2-(3-bromophenyl)ethanol and 2-pyrrolidinone. Purification was achieved by flash chromatography on silica gel eluting with ethyl acetate.

1H-NMR (300 MHz, CDCl$_3$) δ(ppm): 7.60 (s, 1H), 7.40 (d, 1H), 7.30 (t, 1H), 7.00 (d, 1H), 4.40 (t, 2H), 3.85 (m, 4H), 2.85 (t, 2H), 2.60 (t, 2H), 2.10 (q, 2H).

2-[3-(2-oxo-1-pyrrolidinyl)phenyl]ethyl methanesulfonate

Methanesulfonyl chloride (0.124 mL) was added dropwise to a stirred solution of 1-[3-(2-hydroxyethyl)phenyl]-2-pyrrolidinone (0.30 g) and triethylamine (0.42 mL) in dichloromethane (10 mL) at room temperature under an inert atmosphere. The solution was stirred for 2 hours. The reaction mixture was diluted with ethyl acetate (50 mL) and washed with water (50 mL), aqueous hydrochloric acid (1N, 2×50 mL), a saturated aqueous solution of sodium hydrogencarbonate (50 mL) and brine (50 mL). The organic layer was dried over sodium sulfate and concentrated under reduced pressure. The crude was purified by flash chromatography on silica gel, eluting with ethyl acetate-cyclohexane (50:50) to afford the title compound in 93% yield (0.384 g).

1H-NMR (300 MHz, CDCl$_3$) δ(ppm): 7.60 (s, 1H), 7.40 (d, 1H), 7.30 (t, 1H), 7.00 (d, 1H), 4.40 (t, 2H), 3.85 (t, 2H), 3.05 (t, 2H), 2.85 (s, 3H), 2.60 (t, 2H), 2.15 (q, 2H).

1-(3-{2-[4-(2-methyl-5-quinolinyl)-1-piperazinyl]ethyl}phenyl)-2-pyrrolidinone (E152)

N,N-Diisopropylethylamine (0.23 mL) was added to a solution of 2-methyl-5-(1-piperazinyl)quinoline (D3) (0.05 g) and 2-[3-(2-oxo-1-pyrrolidinyl)phenyl]ethyl methanesulfonate (0.071 g) in dimethylformamide (1 mL) and the resulting mixture was heated to 100° C. for 18 hours, then cooled to room temperature. The reaction mixture was diluted with ethyl acetate (50 mL) and washed with water (50 mL), a mixture of water and brine (1:1, 2×50 mL) and brine (50 mL). The organic layer was dried over sodium sulfate and concentrated under reduced pressure. The crude was purified by flash chromatography on silica gel, eluting with methanol-ethyl acetate (90:10) affording the title compound in 77% yield (0.07 g).

MS; (ES) m/z: 415.3 [MH]$^+$, 208.4 [M+2H]$^{2+}$. C$_{26}$H$_{30}$N$_4$O requires 414.
1H-NMR (300 MHz, CDCl$_3$) δ(ppm): 8.37 (d, 1H), 7.70 (d, 1H), 7.57 (m, 2H), 7.37 (m, 1H), 7.25 (m, 2H), 7.07 (d, 1H), 7.03 (bd, 1H), 3.85 (t, 2H), 3.13 (bm, 2H), 2.9-2.75 (bm, 8H), 2.70 (s, 3H), 2.60 (t, 2H), 2.15 (q, 2H).

Example 153

5-(4-{2-[3-(1,1-Dioxido-2-isothiazolidinyl)phenyl]ethyl}-1-piperazinyl)-2-methylquinoline (E153)

To a stirred solution of 3-{2-[4-(2-methyl-5-quinolinyl)-1-piperazinyl]ethyl}aniline (D6, 30 mg) in pyridine (0.5 mL) was added 2-chloroethylsulfonyl chloride (13 µL). The mixture was stirred 1 h then concentrated in vacuo and partitioned between saturated aqueous sodium hydrogencarbonate solution and DCM. The organic layer was washed (water), dried (sodium sulfate) and concentrated in vacuo. The residue was dissolved in THF (1 mL) and cooled to 0° C. with stirring. To the stirred solution was added sodium hydride (60%, 20 mg). The mixture was warmed to room temperature and left to stand for 4 days. The reaction was diluted with water and concentrated in vacuo. The residue was partitioned between DCM and water. The organic layer was washed (water), dried (sodium sulfate) and concentrated in vacuo. The residue was purified by column chromatography ($SiO_2$; EtOAc) to give the title compound (4.4 mg).

1H-NMR (400 MHz, $CDCl_3$) δ(ppm): 8.38 (d, 1H), 7.72 (d, 1H), 7.58 (t, 1H), 7.35-7.07 (m, 6H), 3.34 (s, 3H), 2.86 (s, 3H), 2.73 (s, 3H) and 3.3-2.7 (m, 12H).

Example 154

N-(3-{2-[4-(7-Fluoro-2-methyl-5-quinolinyl)-1 piperazinyl]ethyl}phenyl)acetamide (E154)

2-Methyl-5-(1-piperazinyl)-7-fluoro quinoline

A stirred mixture of piperazine (20 g), potassium carbonate (32 g), 5,7-difluoro-2-methylquinoline hydrochloride (WO2002034754, 20 g) and dimethylsulfoxide (390 mL) was heated to 120° C. for 15 hours. The mixture was cooled to room temperature, diluted with water (600 mL) and extracted with 6×500 mL portions of a mixture of DCM-ether (15:85). The combined organic extracts were washed with water (200 mL) and brine (200 mL), dried (sodium sulfate) and the solvent was partially evaporated under vacuum. The precipitate formed during the evaporation was filtered-off, washed with ether (50 mL) and dried under vacuum to give the title compound (4.7 g, 21%).

1H-NMR (300 MHz, $CDCl_3$) δ(ppm): 8.27 (d, 1H), 7.27 (dd, 1H), 7.17 (dd, 1H), 6.78 (dd, 2H), 3.10 (m, 4H), 3.01 (m, 4H), 2.67 (s, 3H).

7-Fluoro-2-methyl-5-{4-[2-(3-nitrophenyl)ethyl]-1-piperazinyl}quinoline

N,N-Diisopropylethylamine (0.07 mL; 3 eq) was added to a solution of 2-methyl-5-(1-piperazinyl)-7-fluoro quinoline (0.03 g; 1 eq) and 2-(3-nitrophenyl)ethyl methanesulfonate (D4) (0.033 g; 1.1 eq) in dimethylformamide (1.0 mL). The reaction mixture was heated to 90° C. for 10 hours. The dark solution was cooled to room temperature and concentrated under reduced pressure, diluted with water (3 mL) and brine (1 mL) and extracted into ethyl acetate (3×3 mL). The organic layers were combined, dried over sodium sulfate and concentrated under reduced pressure. The crude was purified by flash chromatography on silica, eluting with a gradient from dichloromethane to dichloromethane-MeOH (98:2) affording the title compound in 88% yield (0.04 g).

MS; (ES) m/z: 395.4 [MH]$^+$. $C_{22}H_{23}FN_4O_2$ requires 394.

3-{2-[4-(7-Fluoro-2-methyl-5-quinolinyl)-1-piperazinyl]ethyl}aniline

A solution of 7-fluoro-2-methyl-5-{4-[2-(3-nitrophenyl)ethyl]-1-piperazinyl}quinoline (0.046 g; 1 eq) in methanol (3 mL) was added dropwise to a suspension of iron powder (0.04 g; 7 eq) and ammonium chloride (0.04 g; 7 eq) in water (3 mL). The reactants were heated at reflux for 8 hours, with additional amounts of iron powder (total 0.04 g; 7 eq) and ammonium chloride (0.04 g; 7 eq) added in 3 portions during the reaction. The reaction mixture was cooled to room temperature and filtered using a Millipore filter. The filtrate was concentrated under reduced pressure, diluted with water (5 mL) and a saturated aqueous solution of sodium hydrogen carbonate (2 mL) and extracted into ethyl acetate (3×5 mL). The combined organic extracts were dried over sodium sulfate and concentrated under reduced pressure thus obtaining the title compound in 32% yield (0.012 g).

MS; (ES) m/z: 365.4 [MH]$^+$. $C_{22}H_{25}FN_4$ requires 364.

1H-NMR (300 MHz, $CDCl_3$) δ(ppm): 8.35 (d, 1H), 7.35 (d, 1H), 7.20 (m, 1H), 6.85 (m, 2H), 7.55 (m, 2H), 6.45 (m, 2H), 3.05 (bm, 4H), 2.8-2.7 (bm, 7H), 2.70 (s, 3H).

N-(3-{2-[4-(7-Fluoro-2-methyl-5-quinolinyl)-1piperazinyl]ethyl}phenyl)acetamide (E154)

The Title Compound was Prepared in 46% Yield According to the General Procedure for the preparation of amides (Method B) starting from 3-{2-[4-(7-fluoro-2-methyl-5-quinolinyl)-1-piperazinyl]ethyl}aniline and acetyl chloride:

MS: (ES) m/z: 407.3 [MH$^+$]. $C_{24}H_{28}N_4O$ requires 437.

1H-NMR (300 MHz, $d_6$-DMSO) δ(ppm): 10.48 (bs, 1H), 9.98 (s, 1H), 8.52 (bs, 1H), 7.65 (s, 1H), 7.53 (bs, 1H), 7.45 (bd, 1H), 7.36 (d, 1H), 7.28 (t, 1H), 7.23 (d, 1H), 6.97 (d, 1H), 3.8-3.2 (bm, 10H), 3.06 (dd, 2H), 2.72 (s, 3H), 2.04 (s, 3H).

Example 155

2,2'-[(3-{2-[4-(7-chloro-2-methyl-5-quinolinyl)-1-piperazinyl]ethyl}phenyl)imino]bis(N,N-dimethylacetamide) (E155)

The title compound was isolated in 16% yield following the procedure described for Example 96.

MS: (ES) m/z: 552 [MH$^+$]. $C_{30}H_{39}ClN_6O_2$ requires 551.

1H-NMR (500 MHz, $CD_3OD$) δ(ppm): 9.17 (d, 1H), 7.95 (d, 1H), 7.90 (s, 1H), 7.61 (s, 1H), 7.20 (t, 1H), 6.74 (d, 1H), 6.59 (s, 1H), 6.53 (d, 1H), 4.39 (s, 4H), 3.81-3.62-3.41 (d-t-t, 2-4-2), 3.55 (t, 2H), 3.16-3.03 (t, 2H), 3.01 (s, 3H).

Example 156

1-Ethyl-3-(3-{2-[4-(2-methyl-5-quinolinyl)-1-piperazinyl]ethyl}phenyl)-2-imidazolidinone hydrochloride (E156)

To a stirred solution of 1-(3-{2-[4-(2-methyl-5-quinolinyl)-1-piperazinyl]ethyl}phenyl)-2-imidazolidinone (Example 85, 50 mg) in DMF (1 mL) was added sodium hydride (60%, 10 mg). The mixture was stirred for 15 minutes, then iodoethane (11 L) was added. The mixture was stirred for 90 minutes then diluted with methanol (5 mL) and purified by ion exchange chromatography [SCX-2; MeOH-(1M $NH_3$/MeOH): (100:0)→(0:100)]. The basic washings were concentrated in vacuo and purified by column chromatography [$SiO_2$; cyclohexane-EtOAc-MeOH: (1:1:0)→(0:10:1)] and converted to the hydrochloride salt according to the description given in the general procedure (D6) to give the title compound (49 mg).

MS: (ES) m/z: 444 [MH$^+$]. $C_{27}H_{33}N_5O$ requires 443.

1H-NMR (300 MHz, d$_6$-DMSO) δ(ppm): 11.4 (m, 1H) 9.0 (d, 1H), 7.9 (m, 2H), 7.8 (d, 2H), 7.5 (d, 1H), 7.4 (m, 2H), 7.2 (t, 2H), 6.9 (d, 1H), 3.6 (m, 4H), 3.6-3.3 (m, 10H), 3.2-3.1 (m, 4H), 3.0 (s, 3H) and 1.2 (s, 3H).

Example 157

1-(1-Methylethyl)-3-(3-{2-[4-(2-methyl-5-quinolinyl)-1-piperazinyl]ethyl}phenyl)-2-imidazolidinone dihydrochloride (E157)

The title compound was prepared according to the procedure described for Example 156 using 1-(3-{2-[4-(2-methyl-5-quinolinyl)-1-piperazinyl]ethyl}phenyl)-2-imidazolidinone (Example 85, 50 mg), DMF (1 mL), sodium hydride (60%, 10 mg) and 2-iodopropane (13 μL). Yield 17 mg.

MS: (ES) m/z: 458 [MH$^+$]. $C_{28}H_{35}N_5O$ requires 457.

1H-NMR (300 MHz, d$_6$-DMSO) δ(ppm): 9.00 (d, 1H), 8.05-7.95 (m, 2H), 7.85 (d, 1H), 7.55 (s, 1H), 7.40 (dd, 1H), 7.32 (dd, 1H), 7.27 (t, 1H), 6.90 (d, 1H), 4.05 (sext., 1H), 4.85-4.70 (m, 4H), 3.55-3.25 (m, 10H), 3.15 (t, 2H), 2.95 (s, 3H) and 1.12 (d, 6H).

Example 158

1-(3-{2-[4-(2-Methyl-5-quinolinyl)-1-piperazinyl]ethyl}phenyl)-3-(4-pyridinylmethyl)-2-imidazolidinone dihydrochloride (E158)

The title compound was prepared according to the procedure described for Example 156 using 1-(3-{2-[4-(2-methyl-5-quinolinyl)-1-piperazinyl]ethyl}phenyl)-2-imidazolidinone (Example 85, 50 mg), DMF (1 mL), sodium hydride (60%, 14 mg) and 4-chloromethylpyridine hydrochloride (20 mg). Yield, 19 mg.

MS: (ES) m/z: 507 [MH$^+$]. $C_{31}H_{34}N_6O$ requires 506.

1H-NMR (300 MHz, d$_6$-DMSO) δ(ppm): 9.00 (d, 1H), 8.82 (d, 2H), 8.02-7.95 (m, 2H), 7.92-7.85 (m, 3H), 7.60 (s, 1H), 7.52 (d, 2H), 7.35 (t, 1H), 7.00 (d, 1H), 5.67 (s, 2H), 3.92 (t, 2H), 3.67 (t, 2H), 3.58-3.30 (m, 10H), 3.17 (m, 2H) and 2.92 (s, 3H).

Example 159

1-(3-{2-[4-(2-Methyl-5-quinolinyl)-1-piperazinyl]ethyl}phenyl)-3-(3-pyridinylmethyl)-2-imidazolidinone dihydrochloride (E159)

The title compound was prepared according to the procedure described for Example 156 using 1-(3-{2-[4-(2-methyl-5-quinolinyl)-1-piperazinyl]ethyl}phenyl)-2-imidazolidinone (Example 85, 50 mg), DMF (1 mL), sodium hydride (60%, 14 mg) and 3-chloromethylpyridine hydrochloride (20 mg). Yield, 20 mg.

MS: (ES) m/z: 507 [MH$^+$]. $C_{31}H_{34}N_6O$ requires 506.

1H-NMR (300 MHz, d$_6$-DMSO) δ(ppm): 8.98 (d, 1H), 8.78 (s, 1H), 8.75 (m, 1H), 8.27 (d, 1H), 8.05-7.95 (m, 2H), 7.90-7.82 (m, 2H), 7.62 (s, 1H), 7.50 (m, 2H), 7.35 (t, 1H), 6.98 (d, 1H), 4.57 (s, 2H), 3.87 (t, 2H), 3.71 (m, 2H), 3.57-3.30 (m, 10H), 3.20 (t, 2H) and 2.95 (s, 3H).

Example 160

1-(3-{2-[4-(2-methyl-5-quinolinyl)-1-piperazinyl]ethyl}phenyl)octahydro-2H-benzimidazol-2-one (E160)

The title compound was prepared in 100% yield according to the general procedure for the preparation of the amides, ureas and carbamates (Method A) starting from 5-{4-[2-(3-iodophenyl)ethyl]-1-piperazinyl}-2-methylquinoline and octahydro-2H-benzimidazol-2-one.

MS: (ES/+) m/z: 470 [MH$^+$]. $C_{29}H_{35}N_5O$ requires 469.

1H-NMR (300 MHz, CDCl$_3$) δ(ppm): 8.35 (d, 1H), 7.70 (d, 1H), 7.55 (t, 1H), 7.35-7.00 (m, 6H), 3.5-3.0 (m, 6H), 2.95-2.65 (m, 11H), 2.25-1.30 (m, 8H).

Example 161

(S)-2-(3-{2-[4-(2-Methyl-5-quinolinyl)-1-piperazinyl]ethyl}phenyl)hexahydro-3H-pyrrolo[1,2-c]imidazol-3-one (E161)

(S)-Hexahydro-3H-pyrrolo[1,2-c]imidazol-3-one (S)-2-(Aminomethyl)pyrrolidine (250 mg) and carbonyldiimidazole (400 mg, 1.0 equiv.) were dissolved in DCM (50 mL). The resulting mixture was stirred at room temperature for 18 hours, then concentrated under vacuum. The residue was purified by flash column chromatography (SPE cartridge, SiO$_2$), using DCM-methanol (95:5) as eluent to afford the title compound as colourless solid (150 mg, 50% yield).

MS: (ES/+) m/z: 127 [MH$^+$]. $C_6H_{10}N_2O$ requires 126.

1H-NMR (300 MHz, CDCl$_3$) δ(ppm): 4.3 (br s, 1H), 3.7-3.8 (m, 1H), 3.65-3.55 (m 2H), 3.25 (dd, 1H), 3.05 (m, 1H), 2.00-1.70 (m, 3H), 1.40 (m, 1H).

2-(3-Iodophenyl)ethanol

A solution of borane (1M, THF, 2.5 eq., 38.2 mL) was added dropwise to a stirred solution of (3-iodophenyl)acetic acid (4.0 g) in THF (100 mL) cooled to 0 C. The resulting mixture was stirred at 0 C for 1 h then warmed to room temperature and stirred for a further 3 h. The mixture was poured into aqueous ammonium chloride solution and extracted with ethyl acetate. The combined organic phases were washed with brine, dried (sodium sulfate) and concentrated. The crude was purified by column chromatography (SPE cartridge, SiO$_2$), using cyclohexane-ethyl acetate (70:30) as eluent to afford the title compound (3.5 g, 92% yield).

1H-NMR (400 MHz, CDCl$_3$) δ(ppm): 7.5-7 (m, 5H), 4.0 (m, 2H), 2.9 (m, 2H).

2-(3-Iodophenyl)ethyl methanesulfonate

Methanesulfonyl chloride (1.5 mL, 1.2 eq.) was added dropwise to a stirred solution of 2-(3-iodophenyl)ethanol (3.6 g) in dichloromethane (100 mL) and diisopropylethylamine (3.8 mL, 1.5 equiv.) at 0° C. The solution was warmed to room temperature and stirred for 18 h. The reaction mixture was diluted with aqueous ammonium chloride solution and extracted with dichloromethane. The organic layers were combined, washed with aqueous sodium hydrogencarbonate solution, brine, dried over sodium sulfate and concentrated under reduced pressure. The crude was purified using column chromatography (SiO$_2$ cartridge) using DCM-cyclohexane (70:30) to afford the title compound (3.2 g, 45% yield).

1H-NMR (400 MHz, CDCl$_3$) δ(ppm): 7.58 (m, 2H), 7.25-7.0 (m, 2H), 4.48 (t, 2H), 3.0 (t, 3H).

5-{4-[2-(3-Iodophenyl)ethyl]-1-piperazinyl}-2-methylquinoline

N,N-Diisopropylethylamine (1.7 mL; 1.5 eq) was added to a solution of 2-methyl-5-(1-piperazinyl)quinoline (D3) (1.31 g; 0.9 eq) and 2-(3-iodophenyl)ethyl methanesulfonate (2.1 g) in dimethylformamide (20 mL). The reaction mixture was heated to 90° C. for 5 hours. The dark solution was concentrated under reduced pressure, and purified by ion-exchange chromatography (SCX-2), eluting with methanol-ammonia/methanol (1M), (1:0) to (0:1). The combined basic fractions were concentrated under vacuum and purified by column chromatography (SPE cartridge, $SiO_2$) using dichloromethane-methanol (95:5) to afford the title compound (1.5 g, 60% yield).

MS; (ES) m/z: 457, 459 [MH]$^+$. $C_{22}H_{24}IN_3$ requires 457.
1H-NMR (300 MHz, CDCl$_3$) δ(ppm): 8.35 (d, 1H), 7.5 (d, 1H), 7.6-7.5 (m, 3H), 7.3-7.0 (m, 4H), 3.1 (m, 4H), 2.85-2.65 (m, 11H).

(S)-2-(3-{2-[4-(2-Methyl-5-quinolinyl)-1-piperazinyl]ethyl}phenyl)hexahydro-3H-pyrrolo[1,2-c]imidazol-3-one (E161)

The title compound was prepared in 60% yield according to the general procedure for the preparation of the amides, ureas and carbamates (Method A) starting from 5-{4-[2-(3-iodophenyl)ethyl]-1-piperazinyl}-2-methylquinoline and (S)-hexahydro-3H-pyrrolo[1,2-c]imidazol-3-one.

MS: (ES/+) m/z: 456 [MH$^+$]. $C_{28}H_{33}N_5O$ requires 455.
1H-NMR (400 MHz, CDCl$_3$) δ(ppm): 10.68 (v br s, 1H), 8.82 (v br s, 1H), 7.88 (br s, 2H), 7.76 (br s, 1H), 7.66 (s, 1H), 7.47 (d, 1H), 7.40 (br s, 1H), 7.34 (t, 3H), 7.00 (d, 1H), 4.10-3.0 (v br m, 17H), 2.86 (br s, 3H), 2.1-1.37 (m, 4H).

Example 162

(R)-2-(3-{2-[4-(2-Methyl-5-quinolinyl)-1-piperazinyl]ethyl}phenyl)hexahydro-3H-pyrrolo[1,2-c]imidazol-3-one (E162)

(R)-(1,1-Dimethylethyl 2-{[(3-{2-[4-(2-methyl-5-quinolinyl)-1-piperazinyl]ethyl}phenyl)amino]methyl}-1-pyrrolidinecarboxylate 3-{2-[4-(2-Methyl-5-quinolinyl)-1-piperazinyl]ethyl}aniline (D6, 115 mg) and N-(tert-butoxycarbonyl)-L-prolinal (1.2 equiv., 79 mg) were stirred in methanol (2 mL) until the mixture became a clear solution. Then, sodium triacetoxyborohydride (1.2 eq., 85 mg) was added. After 24 h the reaction mixture was loaded onto an ion-exchange cartridge (SCX-2) and eluted with methanol followed by ammonia/methanol (1M). The combined basic fractions were concentrated in vacuo and purified by column chromatography (SPE cartridge, silica) using DCM-methanol (95:5) as eluent to afford the title compound (70 mg, 40% yield).

MS: (ES/+) m/z: 530 [MH$^+$]. $C_{32}H_{43}N_5O_2$ requires 529.
1H-NMR (300 MHz, CDCl$_3$) δ(ppm): 8.35 (d, 1H), 7.70 (d, 1H), 7.2 (d, 1H), 7.15-7.00 (m, 2H), 6.5 (br m, 3H), 4.00-2.90 (v br m, 20H) (m, 4H), 2.00-1.50 (vr b m, 13H).

(R)-2-(3-{2-[4-(2-Methyl-5-quinolinyl)-1-piperazinyl]ethyl}phenyl)hexahydro-3H-pyrrolo[1,2-c]imidazol-3-one (E162)

A solution of (R)-(1,1-dimethylethyl 2-{[(3-{2-[4-(2-methyl-5-quinolinyl)-1-piperazinyl]ethyl}phenyl)amino]methyl}-1-pyrrolidinecarboxylate in methanol was treated with a solution of hydrogen chloride in ether (1M). The resulting mixture was stirred 30 minutes then concentrated under vacuum and then loaded onto an ion-exchange cartridge (SCX-2) and eluted with methanol followed by ammonia in methanol (1 M). The combined basic fractions were concentrated under vacuum. The residue, (10 mg) was then dissolved in DCM (1 mL) and treated with triphosgene (23 mg, 0.3 eq.), diisopropylamine (4 uL, 3 eq.). The mixture was stirred for 1 h then concentrated under vacuum and purified by preparative mass-directed hplc to afford the title compound (3.1 mg).

MS: (ES/+) m/z: 456 [MH$^+$]. $C_{28}H_{33}N_5O$ requires 455.
1H-NMR (300 MHz, CDCl$_3$) δ(ppm): 8.35 (d, 1H), 7.75 (d, 1H), 7.65 (s, 1H), 7.60 (d, 1H), 7.20-7.35 (m, 3H), 7.30 (d, 1H), 6.95 (d, 1H), 6.5 (br m, 3H), 4.00-2.90 (v br m, 12H) 2.85 (s, 3H), 2.00-1.50 (m, 4H).

Example 163

5,5-Dimethyl-1-(3-{2-[4-(2-methyl-5-quinolinyl)-1-piperazinyl]ethyl}phenyl)-2-imidazolidinone (E163)

4,4-Dimethyl-2-imidazolidinone

A solution of (2-amino-1,1-dimethylethyl)amine (1.0 g) and 1,1'-carbonylimidazole (1.9 g, 1.0 equiv.) in DCM (50 mL) was stirred for 18 hours then concentrated and purified using column chromatography (SPE cartridge, $SiO_2$), using DCM-methanol (95:5) as eluent to afford the title compound as colourless solid (1.0 g, 83% yield).

MS: (ES/+) m/z: 115 [MH$^+$]. $C_5H_{10}N_2O$ requires 114.
1H-NMR (300 MHz, CDCl$_3$) δ (ppm): 4.5 (br s, 1H), 3.25 (s, 2H), 1.25 (s, 6H).

5,5-Dimethyl-1-(3-{2-[4-(2-methyl-5-quinolinyl)-1-piperazinyl]ethyl}phenyl)-2-imidazolidinone (E163)

The title compound was prepared in 87% yield according to the general procedure for the preparation of the amides, ureas and carbamates (Method A) starting from 5-{4-[2-(3-iodophenyl)ethyl]-1-piperazinyl}-2-methylquinoline and 4,4-dimethyl-2-imidazolidinone.

MS: (ES/+) m/z: 444 [MH$^+$]. $C_{27}H_{33}N_5O$ requires 443.
1H-NMR (400 MHz, CDCl$_3$) δ(ppm): 10.89 (br s, 1H), 8.87 (br s, 1H), 7.92 (br s, 2H), 7.58 (dd, 1H), 7.4 (br s, 1H), 7.44 (dd, 1H), 7.3 (t, 1H), 7.21 (s, 1H), 6.95 (d, 1H), 3.74 (dd, 2H), 3.61 (s, 2H), 3.60-3.30 (m, 8H), 2.87 (s, 3H), 1.3 (s, 6H).

Example 164

(R or S) 1-(3-{2-[4-(2-Methyl-5-quinolinyl)-1-piperazinyl]propyl}phenyl)-2-imidazolidinone (E164)

Racemic 1-(3-{2-[4-(2-methyl-5-quinolinyl)-1-piperazinyl]propyl}phenyl)-2-imidazolidinone was prepared in 41% yield according to the general procedure for the preparation of the amides, ureas and carbamates (Method A) starting from 5-{4-[2-(3-bromophenyl)propyl]-1-piperazinyl}-2-methylquinoline (D20) and 2-imidazolidinone.

The racemate was separated using preparative chiral HPLC (Daicel Chiralcel OD column), eluting with n-hexane-ethanol (60:40) to afford the title compound as the first-eluting enantiomer.

MS: (ES/+) m/z: 430 [MH$^+$]. $C_{26}H_{31}N_5O$ requires 429.
1H-NMR (500 MHz, d$_6$-DMSO) δ (ppm): 10.62 (br s, 1H), 8.94 (br s, 1H), 7.88 (br s, 2H), 7.75 (br s, 1H), 7.58 (s, 1H), 7.50-6.90 (m, 4H), 6.08 (br s, 1H), 3.90-2.70 (br m, 15H), 2.85 (br s, 3H), 1.22 (d, 3H).

Example 165

(S or R) 1-(3-{2-[4-(2-Methyl-5-quinolinyl)-1-piperazinyl]propyl}phenyl)-2-imidazolidinone (E165)

The title compound was prepared according to the method described for Example 164, and was isolated as the second-eluting enantiomer.

MS: (ES/+) m/z: 430 [MH$^+$]. $C_{26}H_{31}N_5O$ requires 429.

1H-NMR (500 MHz, $d_6$-DMSO) δ (ppm): 10.62 (br s, 1H), 8.94 (br s, 1H), 7.88 (br s, 2H), 7.75 (br s, 1H), 7.58 (s, 1H), 7.50-6.90 (m, 4H), 6.08 (br s, 1H), 3.90-2.70 (br m, 15H), 2.85 (br s, 3H), 1.22 (d, 3H).

Example 166

N-(3-{3-[4-(2-Methyl-quinolin-5-yl)-piperazin-1-yl]-propyl}-phenyl)-methanesulfonamide (E166)

N-(3-Iodo-phenyl)-methanesulfonamide

To a stirred solution of 3-iodoaniline (1.99 g, 9.1 mmol) in anhydrous pyridine (20 mL) at 0° C. was added methanesulfonic anhydride (1.92 g, 11 mmol) in small portions. The resulting mixture was stirred while warming from 0° C. to room temperature until all the aniline was consumed. The pyridine was removed in vacuo. The residue was partitioned between dichloromethane (100 mL) and saturated aqueous sodium hydrogencarbonate solution (100 mL). The organic layer was dried (sodium sulfate) and evaporated in vacuo. The crude product was purified by silica gel chromatography (ethyl acetate in hexane, 10% to 30%) to give the title compound as a yellow solid (2.38 g, 89%).

Mass spectrum (API-): Found 296 ([M-H]$^-$). $C_7H_{81}NO_2S$ requires 297.

1H NMR (CDCl$_3$) δ (ppm): 3.04 (3H, s), 6.42 (1H, br. s), 7.08 (1H, m), 7.22 (1H, m), 7.53 (1H, m), 7.56 (1H, s).

N-[3-(3-Oxo-propyl)-phenyl]-methanesulfonamide

A mixture of N-(3-iodo-phenyl)-methanesulfonamide (2.4 g, 8 mmol), tetra-n-butyl-ammonium chloride (2.22 g, 8 mmol), allyl alcohol (0.7 g, 12 mmol), sodium hydrogencarbonate (1.6 g, 19 mmol) and palladium(II) chloride (0.36 g, 1.8 mmol) in anhydrous dimethylformamide (30 mL) was stirred at room temperature for 48 h under argon. The mixture was then diluted with 5% aqueous hydrochloric acid (100 mL) and extracted with ethyl acetate (2×100 mL). The combined organic layers were dried (sodium sulfate) and evaporated in vacuo. The crude product was purified by silica gel chromatography (ethyl acetate in hexane, 30% to 50%) to give the title compound as an amber oil (1.1 g, 60%).

Mass spectrum (API-): Found 226 ([M-H]$^-$). $C_{10}H_{13}NO_3S$ requires 227.

1H NMR (CDCl$_3$) δ (ppm): 2.80 (2H, m), 2.96 (2H, t, J=8 Hz), 3.01 (3H, s), 6.46 (1H, br. s), 7.00-7.10 (3H, m), 7.28 (1H, t, J=8 Hz), 9.82 (1H, s).

N-(3-{3-[4-(2-Methyl-quinolin-5-yl)-piperazin-1-yl]-propyl}-phenyl)-methanesulfonamide (E166)

The title compound was prepared from N-[3-(3-oxo-propyl)-phenyl]-methanesulfonamide and of 2-methyl-5-(1-piperazinyl)quinoline (D3) according to the methods in Description 4 and Description 5.

Mass spectrum (API-): Found 437 ([M-H]$^-$). $C_{24}H_{30}N_4O_2S$ requires 438.

1H NMR (CDCl$_3$) δ (ppm): 1.91 (2H, m), 2.50 (2H, m), 2.71 (6H, m), 2.73 (3H, s), 3.02 (3H, s), 3.12 (4H, m), 6.30 (1H, br. s), 7.00-7.10 (4H, m), 7.26 (2H, m), 7.58 (1H, t, J=8 Hz), 7.72 (1H, d, J=8 Hz), 8.28 (1H, d, J=8 Hz).

Example 167

4-(3-{2-[4-(2-Methyl-5-quinolinyl)-1-piperazinyl]ethyl}phenyl)-2,4-dihydro-3H-1,2,4-triazol-3-one (E167)

The title compound was obtained as a mixture (85:15) with the regioisomer 2-(3-{2-[4-(2-methyl-5-quinolinyl)-1-piperazinyl]ethyl}phenyl)-1,2-dihydro-3H-1,2,4-triazol-3-one following the general procedure for the preparation of amides, ureas and carbamates (Method A) starting from 5-{4-[2-(3-iodophenyl)ethyl]-1-piperazinyl}-2-methylquinoline and 1,2-dihydro-3H-1,2,4-triazol-3-one.

MS: (ES/+) m/z: 415 [MH$^+$]. $C_{24}H_{26}N_6O$ requires 414.

1H-NMR (300 MHz, CDCl$_3$) δ(ppm): 11.92 (bs, 1H), 8.32 (d, 1H), 8.30 (d, 1H), 7.55 (br s, 1H), 7.53 (m, 2H), 7.48 (dd, 1H), 7.37 (t, 1H), 7.34 (d, 1H), 7.22 (d, 1H), 7.05 (dd, 1H), 7.05 (dd, 1H), 2.99 (br s, 4 h), 2.85-2.6 (m, 10H), 2.58 (s, 4H).

Example 168

5-methyl-2-(3-{2-[4-(2-methyl-5-quinolinyl)-1-piperazinyl]ethyl}phenyl)-2,4-dihydro-3H-pyrazol-3-one (E168)

The title compound was prepared in 58% yield according to the general procedure for the preparation of amides, ureas and carbamates (Method A) starting from 5-{4-[2-(3-iodophenyl)ethyl]-1-piperazinyl}-2-methylquinoline and 5-methyl-2,4-dihydro-3H-pyrazol-3-one.

MS: (ES/+) m/z: 428 [MH$^+$]. $C_{26}H_{29}N_5O$ requires 427.

1H-NMR (300 MHz, CDCl$_3$) δ(ppm): 8.30 (d, 1H), 7.65 (m, 2H), 7.50 (t, 1H), 7.27-7.16 (m, 3H), 7.01-6.98 (m, 2H) 3.08 (m, 4H), 2.90-2.60 (m, 14H), 2.14 (s, 2H).

Example 169

2-(4-Fluoro-3-{2-[4-(2-methyl-5-quinolinyl)-1-piperazinyl]ethyl}phenyl)-5-methyl-2,4-dihydro-3H-pyrazol-3-one (E169)

The title compound was prepared in 92% yield according to the general procedure for the preparation of amides, ureas and carbamates (Method A) starting from 5-{4-[2-(3-iodophenyl)ethyl]-1-piperazinyl}-2-methylquinoline and 5-methyl-2,4-dihydro-3H-pyrazol-3-one.

MS: (ES/+) m/z: 446 [MH$^+$]. $C_{26}H_{28}FN_5O$ requires 445.

1H-NMR (300 MHz, CDCl$_3$) δ(ppm): 8.30 (d, 1H), 7.71-7.59 (m, 3H), 7.50 (t, 1H), 7.17 (d, 1H), 7.0-6.4 (m, 2H), 3.35 (s, 2H), 3.05 (m, 4H), 2.88-2.64 (m, 11H), 2.13 (s, 2H).

Example 170

5-(4-{2-[3-(5,6-dihydro-7H-imidazo[2,1-c][1,2,4]triazol-7-yl)phenyl]ethyl}-1-piperazinyl)-2-methylquinoline (E170)

5,6-Dihydro-1H-imidazo[2,1-c][1,2,4]triazole

2-Hydrazino-2-imidazoline hydrobromide (200 mg) was suspended in ethyl orthoformate (2 ml) and stirred at 150° C. under microwave irradiation for 10 min. The reaction mixture was cooled to room temperature then diluted with methanol and loaded onto an ion-exchange column (SCX-2), which was eluted with methanol followed by ammonia-methanol solution (1M). The combined basic fractions were concentrated under vacuum and purified using column chromatography [SiO$_2$; DCM-MeOH (90:10)] to afford the title compound as colourless solid (60 mg, 60% yield).

MS: (ES/+) m/z: 112 [MH$^+$]. C$_4$H$_6$N$_4$ requires 111.

1H-NMR (300 MHz, CDCl$_3$) δ(ppm): 7.95 (s, 1H), 6.25 (s, 1H), 3.95 (m, 4H).

5-(4-{2-[3-(5,6-Dihydro-7H-imidazo[2,1-c][1,2,4]triazol-7-yl)phenyl]ethyl}-1-piperazinyl)-2-methylquinoline (E170)

5-{4-[2-(3-Iodophenyl)ethyl]-1-piperazinyl}-2-methylquinoline (59 mg), 5,6-dihydro-1H-imidazo[2,1-c][1,2,4]triazole (50 mg, 3.5 equiv.), palladium(II) acetate (9 mg, 0.3 equiv.) 2-(dicyclohexylphosphino)-2'-methylbiphenyl (42 mg, 0.9 equiv.) and potassium phosphate (97 mg, 3.5 equiv.) were suspended in DME and stirred at 150 C under microwave irradiation for 2 h. The mixture was cooled to room temperature, diluted with methanol and loaded onto an ion-exchange cartridge (SCX-2), which was eluted with methanol followed by ammonia-methanol solution (1M). The combined basic fractions were concentrated under vacuum and purified using column chromatography [SiO$_2$; DCM-MeOH (90:10)] to afford the title compound as colourless solid (13 mg, 26% yield).

MS: (ES/+) m/z: 440 [MH$^+$]. C$_{26}$H$_{29}$N$_7$ requires 439.

1H-NMR (300 MHz, CDCl$_3$) δ(ppm): 8.40 (d, 1H), 7.90 (s, 1H), 7.70 (d, 1H), 7.6-7.5 (m, 2H), 7.35-7.20 (m, 3H), 7.1 (d, 1H), 6.9 (d, 1H), 4.55 (t, 2H), 4.28 (t, 2H), 3.15 (m, 4H), 3.0-2.7 (m, 11H).

What is claimed is:

1. A process for the preparation of a compound of formula (I) or a pharmaceutically acceptable salt thereof,

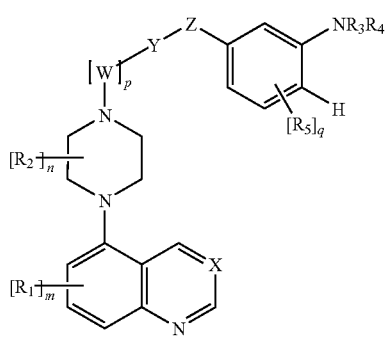

wherein:
n, p, and q are each 0, such that R$_2$, W, and R$_5$ are absent;
m is 1;
Y and Z are each —CH$_2$—;
R$_1$ is halogen, cyano, C$_{1-6}$alkyl, C$_{1-6}$alkoxy, haloC$_{1-6}$alkoxy or haloC$_{1-6}$alkyl;
X is N or CH; and
R$_3$ and R$_4$ are independently hydrogen, C$_{1-6}$alkyl, C$_{1-6}$alkylsulfonyl, a group having the formula (IIa):

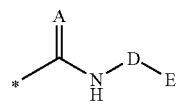

wherein A is oxygen or sulfur, D is —(CH$_2$)$_t$—, —(CH$_2$)$_t$O— or —O(CH$_2$)$_t$—, wherein t is 0, 1, 2, 3 or 4; and E is C$_{1-6}$alkyl; C$_{3-7}$cycloalkyl, optionally substituted by one or more substituents independently selected from halogen, hydroxy, oxo, C$_{1-6}$alkyl, cyano, CF$_3$, OCF$_3$, C$_{1-6}$alkoxy and C$_{1-6}$alkanoyl; or aryl, optionally substituted by one or more substituents independently selected from halogen, C$_{1-6}$alkyl, CF$_3$, cyano, hydroxy, C$_{1-6}$alkanoyl, and C$_{1-6}$alkoxy;

or a group having the formula (IIb)

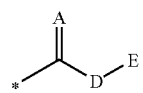

wherein A is oxygen or sulfur, D is —(CH$_2$)$_t$—, —(CH$_2$)$_t$O— or —O(CH$_2$)$_t$—, wherein t is 0, 1, 2, 3 or 4; and E is C$_{1-6}$alkyl; C$_{3-7}$cycloalkyl, optionally substituted by one or more substituents independently selected from halogen, hydroxy, oxo, C$_{1-6}$alkyl, cyano, CF$_3$, OCF$_3$, C$_{1-6}$alkoxy and C$_{1-6}$alkanoyl; or aryl optionally substituted by one or more substituents independently selected from halogen, C$_{1-6}$alkyl, CF$_3$, cyano, hydroxy, C$_{1-6}$alkanoyl, and C$_{1-6}$alkoxy;

or R$_3$ and R$_4$, together with the nitrogen atom to which R$_3$ and R$_4$ are attached, combine to form a 3-7 membered monocyclic heterocyclic group or a 8-11 membered bicyclic heterocyclic group, wherein each group is optionally substituted by one or more substituents selected from halogen, oxo, C$_{1-6}$alkyl, cyano, CF$_3$, C$_{1-6}$alkoxy, C$_{1-6}$alkanoyl, aryl and arylC$_{1-6}$alkyl, wherein the aryl and arylC$_{1-6}$alkyl are further optionally substituted by one or more halogen, oxo, C$_{1-6}$alkyl, cyano, CF$_3$, C$_{1-6}$alkoxy and C$_{1-6}$alkanoyl;

which process comprises reacting a compound of formula (VII):

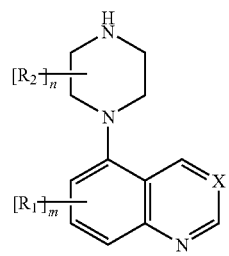

wherein $R_1$, m, X, $R_2$ and n are as defined for formula (I), with a compound of formula (VIII):

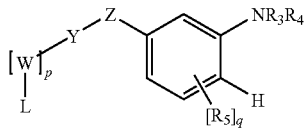

(VIII)

wherein W, p, Y, Z, $R_5$, q, $R_3$ and $R_4$ are as defined for formula (I), and L is selected from the group consisting of chloro, bromo, iodo, tosylate, brosylate, nosylate, mesylate, fluorosulfonate, triflate, nonaflate, and tresylate; in the presence of a base, and thereafter optionally:
   removing any protecting groups and/or
   forming a pharmaceutically acceptable salt.

2. The process according to claim 1 wherein the base is triethylamine or N'N-diisopropylethylamine.

3. The process according to claim 1 wherein:
   $R_1$ is methyl;
   X is CH; and
   $R_3$ and $R_4$, together with the nitrogen atom to which $R_3$ and $R_4$ are attached, combine to form a 3-7 membered monocyclic heterocyclic group selected from

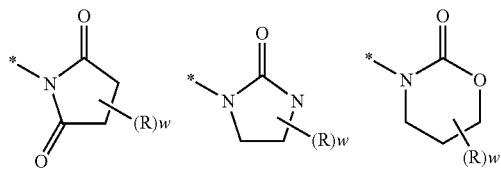

-continued

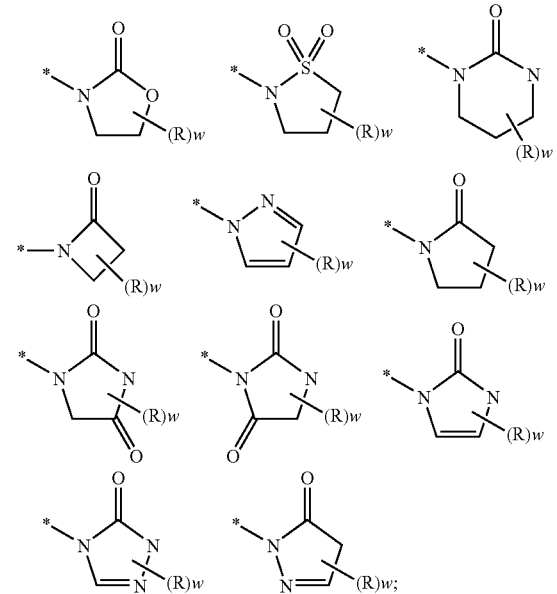

wherein w is 0, 1, 2, 3 or 4 and R is independently halogen, oxo, $C_{1-6}$alkyl, cyano, $CF_3$, $C_{1-6}$alkoxy, $C_{1-6}$alkanoyl, aryl and aryl$C_{1-6}$alkyl, wherein the aryl and aryl$C_{1-6}$alkyl are further optionally substituted by one or more halogen, oxo, $C_{1-6}$alkyl, cyano, $CF_3$, $C_{1-6}$alkoxy and $C_{1-6}$alkanoyl.

4. The process according to claim 1 wherein the compound of formula (I) is 1-(3-{2-[4-(2-methyl-5-quinolinyl)-1-piperazinyl]ethyl}phenyl)-2-imidazolidinone.

* * * * *